US009376400B2

(12) United States Patent  
Chen et al.

(10) Patent No.: US 9,376,400 B2  
(45) Date of Patent: Jun. 28, 2016

(54) PROCESS FOR THE SYNTHESIS OF TRIAZOLES

(71) Applicant: Melinta Therapeutics, Inc., New Haven, CT (US)

(72) Inventors: Shili Chen, Cheshire, CT (US); Rongliang Lou, Cheshire, CT (US); Yusheng Wu, New Haven, CT (US); Jiacheng Zhou, Newark, DE (US); Roger Hanselmann, Branford, CT (US)

(73) Assignee: MELINTA THERAPEUTICS, INC., New Haven, CT (US)

( * ) Notice: Subject to any disclaimer, the term of this patent is extended or adjusted under 35 U.S.C. 154(b) by 0 days.

(21) Appl. No.: 14/325,248

(22) Filed: Jul. 7, 2014

(65) Prior Publication Data

US 2015/0158827 A1    Jun. 11, 2015

Related U.S. Application Data

(63) Continuation of application No. 13/845,759, filed on Mar. 18, 2013, now Pat. No. 8,796,465, which is a continuation of application No. 11/921,838, filed as application No. PCT/US2006/022424 on Jun. 8, 2006, now Pat. No. 8,399,660.

(60) Provisional application No. 60/688,990, filed on Jun. 8, 2005.

(51) Int. Cl.  
*C07D 249/04* (2006.01)  
*C07D 413/14* (2006.01)  
*C07F 7/08* (2006.01)  
*C07D 413/06* (2006.01)  
*C07D 413/12* (2006.01)

(52) U.S. Cl.  
CPC ............ *C07D 249/04* (2013.01); *C07D 413/06* (2013.01); *C07D 413/12* (2013.01); *C07D 413/14* (2013.01); *C07F 7/0814* (2013.01)

(58) Field of Classification Search  
None  
See application file for complete search history.

(56) References Cited

U.S. PATENT DOCUMENTS

| | | |
|---|---|---|
| 4,348,393 A | 9/1982 | Bourgery et al. |
| 4,948,801 A | 8/1990 | Carlson et al. |
| 5,043,443 A | 8/1991 | Carlson et al. |
| 5,130,316 A | 7/1992 | Carlson et al. |
| 5,254,577 A | 10/1993 | Carlson et al. |
| 5,523,403 A | 6/1996 | Barbachyn |
| 5,565,571 A | 10/1996 | Barbachyn et al. |
| 5,627,181 A | 5/1997 | Riedl et al. |
| 5,654,428 A | 8/1997 | Barbachyn et al. |
| 5,654,435 A | 8/1997 | Barbachyn et al. |
| 5,684,023 A | 11/1997 | Riedl et al. |
| 5,756,732 A | 5/1998 | Barbachyn et al. |
| 5,801,246 A | 9/1998 | Barbachyn et al. |
| 5,843,967 A | 12/1998 | Riedl et al. |
| 5,922,708 A | 7/1999 | Riedl et al. |
| 5,929,248 A | 7/1999 | Barbachyn et al. |
| 5,981,528 A | 11/1999 | Gravestock |
| 6,239,152 B1 | 5/2001 | Gordeev et al. |
| 6,271,383 B1 | 8/2001 | Gravestock |
| 6,365,751 B1 | 4/2002 | Gravestock |
| 6,441,005 B1 | 8/2002 | Gordeev et al. |
| 6,495,551 B1 | 12/2002 | Betts et al. |
| 6,531,470 B1 | 3/2003 | Gordeev et al. |
| 6,562,844 B2 | 5/2003 | Gordeev et al. |
| 6,605,630 B1 | 8/2003 | Gravestock |
| 6,617,339 B1 | 9/2003 | Gravestock |
| 6,638,955 B2 | 10/2003 | Gravestock |
| 6,689,779 B2 | 2/2004 | Lee et al. |
| 6,821,980 B1 | 11/2004 | Guerry et al. |
| 6,969,726 B2 | 11/2005 | Lou et al. |
| 7,129,259 B2 * | 10/2006 | Chen ................... C07D 263/20 514/376 |
| 8,399,660 B2 | 3/2013 | Chen et al. |
| 8,796,465 B2 | 8/2014 | Chen et al. |
| 2002/0169191 A1 | 11/2002 | Gordeev et al. |
| 2002/0183371 A1 | 12/2002 | Gordeev et al. |
| 2003/0144263 A1 | 7/2003 | Gravestock |
| 2003/0166620 A1 | 9/2003 | Lee et al. |
| 2004/0132764 A1 | 7/2004 | Locher |
| 2005/0038092 A1 | 2/2005 | Fukuda |
| 2005/0043317 A1 | 2/2005 | Zhou et al. |
| 2006/0270637 A1 | 11/2006 | Gravestock et al. |
| 2007/0197541 A1 | 8/2007 | Oyelere et al. |

FOREIGN PATENT DOCUMENTS

| | | |
|---|---|---|
| DE | 10034627 A1 | 1/2002 |
| EP | 0352781 A2 | 1/1990 |
| EP | 0694543 A1 | 1/1996 |
| EP | 1286998 A1 | 3/2003 |
| JP | 8151577 A | 6/1996 |
| JP | 8151578 A | 6/1996 |
| WO | WO-9309103 A1 | 5/1993 |
| WO | WO-9413649 A1 | 6/1994 |
| WO | WO-9730995 A1 | 8/1997 |
| WO | WO-9854161 A1 | 12/1998 |
| WO | WO-9910342 A1 | 3/1999 |
| WO | WO-9928317 A1 | 6/1999 |
| WO | WO-9933839 A1 | 7/1999 |

(Continued)

OTHER PUBLICATIONS

Brickner, S. J., "Oxazolidinone Antibacterial Agents," Curr. Pharm. Des., 2(2):175-194 (1996).

(Continued)

*Primary Examiner* — Kamal Saeed  
(74) *Attorney, Agent, or Firm* — Wilmer Cutler Pickering Hale and Dorr LLP

(57) ABSTRACT

The present invention relates to processes for the preparation of triazoles. These compounds are useful as anti-infective, anti-proliferative, anti-inflammatory, and prokinetic agents.

2 Claims, No Drawings

(56) References Cited

FOREIGN PATENT DOCUMENTS

| WO | WO-9937630 A1 | 7/1999 |
|---|---|---|
| WO | WO-99/64417 A2 | 12/1999 |
| WO | WO-9964416 A2 | 12/1999 |
| WO | WO-0010566 A1 | 3/2000 |
| WO | WO-0021960 A1 | 4/2000 |
| WO | WO-0029396 A1 | 5/2000 |
| WO | WO-0109107 A1 | 2/2001 |
| WO | WO-0132633 A1 | 5/2001 |
| WO | WO-0140236 A2 | 6/2001 |
| WO | WO-0142229 A1 | 6/2001 |
| WO | WO-0181350 A1 | 11/2001 |
| WO | WO-0194342 A1 | 12/2001 |
| WO | WO-02053560 A1 | 7/2002 |
| WO | WO-02080841 A2 | 10/2002 |
| WO | WO-02081468 A1 | 10/2002 |
| WO | WO-02081469 A1 | 10/2002 |
| WO | WO-02081470 A1 | 10/2002 |
| WO | WO-02096890 A2 | 12/2002 |
| WO | WO-02096916 A1 | 12/2002 |
| WO | WO-03022824 A1 | 3/2003 |
| WO | WO-03035648 A1 | 5/2003 |
| WO | WO-03072553 A1 | 9/2003 |
| WO | WO-03072575 A1 | 9/2003 |
| WO | WO-03084534 A1 | 10/2003 |
| WO | WO-2004029066 A2 | 4/2004 |
| WO | WO-2004048392 A1 | 6/2004 |
| WO | WO-2004056817 A1 | 7/2004 |
| WO | WO-2004056818 A1 | 7/2004 |
| WO | WO-2004056819 A1 | 7/2004 |
| WO | WO-2004078753 A1 | 9/2004 |
| WO | WO-2004089943 A1 | 10/2004 |
| WO | WO-2005003087 A2 | 1/2005 |
| WO | WO-2005012270 A2 | 2/2005 |
| WO | WO-2005012271 A2 | 2/2005 |
| WO | WO-2005019211 A2 | 3/2005 |
| WO | WO-2005058886 A1 | 6/2005 |
| WO | WO-2005061468 A1 | 7/2005 |
| WO | WO-2005070904 A2 | 8/2005 |
| WO | WO-2006133397 A2 | 12/2006 |

OTHER PUBLICATIONS

Gleave, et al., "Synthesis and Antibacterial Activity of [6,6,5] and [6,6,5] Tricyclic Fused Oxazolidinones," Bioorg. Med. Chem. Lett., 8:1231-1236 (1998).

Gregory, et al. "Antibacterials. Synthesis and Structure-Activity Studies of 3-Aryl-2-Oxazolidinones. 1. The 'B' Group," J. Med. Chem. 32.8(1989):1673-1681.

Himo, et al., "Copper(I)-Catalyzed Synthesis of Azoles. DFT Study Predicts Unprecedented Reactivity and Intermediates," J. Am. Chem. Soc., 127(1):210-216 (2004).

International Search Report and Written Opinion for International Patent Application No. PCT/US2004/024339 mailed Jun. 7, 2005 (22 pages).

International Search Report and Written Opinion for International Patent Application No. PCT/US2004/17097 mailed Sep. 16, 2005 (21 pages).

Molander, et al., "Palladium-Catalyzed Suzuki-Miyaura Cross-Coupling Reactions of Potassium Aryl- and Heteroaryltrifluoroborates," J. Org. Chem., 68:4302-4314 (2003).

Orgueira, et al., "Regioselective synthesis of [1,2,3]-triazoles catalyzed by C(I) generated in situ from Cu(O) nanosize activated powder and amine hydrochloride salts," Tetra. Lett., 46(16):2911-2914 (2005).

Park, et al.,"Antibacterials. Synthesis and Structure-Activity Studies of 3-Aryl-2-Oxazolidinones. 4. Multiply-Substituted Aryl Derivatives," J. Med. Chem., 35(6):1156-1165 (1992).

Partial Search Report for International Patent Application No. PCT/2004/017101 mailed Aug. 19, 2005 (10 pages).

Partial Search Report for International Patent Application No. PCT/2004/024334 mailed Aug. 19, 2005 (11 pages).

Reck, et al., "Novel Substituted (Pyridin-3-yl)phenyloxazolidinones: Antibacterial Agents with Reduced Activity against Monoamine Oxidase A and Increased Solubility," J. Med. Chem., 50:4868-4881 (2007).

Rostovtsev, et al., "A Stepwise Huisgen Cycloaddition Process: Copper(I)-Catalyzed Regioselective Ligation of Azides and Terinal Alkynes," Angewandte Chemie International Ed., 41(14):2596-2599 (2002).

Verkhozina, et al., "Synthesis of Polynuclear Nonfused Azoles," Russian J. Org. Chem., 39(12):1863-1867 (2003).

Wu, et al., "Efficiency and Fidelity in a Click-Chemistry Route to Triazole Dendrimers by the Copper(I)-Catalyzed Ligation of Azides and Alkynes," Angewandte Chemie International Ed., 43(30):3928-3932 (2004).

Zurenko, et al., "Oxazolidinone Antibacterial Agents: Development of the Clinical Candidates Eperezolid and Linezolid," Exp. Opin. Invest. Drugs, 6(2):151-158 (1997).

Lowry, F. D., "Antimicrobial Resistance: The Example of Staphylococcus aureus," J. Clin. Invest., vol. 111, No. 9, pp. 1265-1273 (2003).

Gold, H.S. and Moellering, R.C., Jr., "Antimicrobial-Drug Resistance," N. Eng. J. Med., vol. 335, No. 19, pp. 1445-1453 (1996).

Moellering, R.C., Jr., "Linezolid: The First Oxazolidinone Antimicrobial," Annals of Internal Medicine, vol. 138, pp. 135-142 (2003).

Tsiodras, et al., "Linezolid resistance in a clinical isolate of Staphylococcus aureus," The Lancet, vol. 358, p. 207-208 (2001).

Gonzales, et al., "Infections due to vancomycin-resistant Enterococcus faecium resistant to linezolid," The Lancet, vol. 357, p. 1179 (2001).

Zurenko, et al., "Development of linezolid-resistant Enterococcus faecium in two compassionate use program patients treated with linezolid," Proceedings of the 39th Annual Interscience Conference on Antimicrobial Agents and Chemotherapy (ICAAC), San Francisco, CA, USA (Sep. 26-29, 1999) (2 pgs.).

Miyaura, et al., "A new stereospecific cross-coupling by the palladium-catalyzed reaction of 1-alkenylboranes with 1-alkenyl or 1-alkynyl halides," Tetrahedron Letters, pp. 3437-3440 (1979).

Miyaura, N. and Suzuki, A., "Stereoselective synthesis of arylated (E)-alkenes by the reaction of alk-1-enylboranes with aryl halides in the presence of palladium catalyst," J.C.S. Chem. Comm., pp. 866-867 (1979).

\* cited by examiner

PROCESS FOR THE SYNTHESIS OF TRIAZOLES

RELATED APPLICATIONS

This application is a continuation of U.S. patent application Ser. No. 13/845,759, filed Mar. 18, 2013, which is a continuation of U.S. patent application Ser. No. 11/921,838, filed Jun. 1, 2010, now U.S. Pat. No. 8,399,660, which is a national stage application filed under 35 U.S.C. §371 of International Application No. PCT/US2006/022424, filed Jun. 8, 2006, which claims the benefit of and priority to U.S. Patent Application Ser. No. 60/688,990, filed Jun. 8, 2005, the disclosure of which are incorporated by reference herein.

FIELD OF THE INVENTION

The present invention relates to processes for synthesizing anti-infective, anti-proliferative, anti-inflammatory, and prokinetic agents. More particularly, the invention relates to processes for synthesizing triazoles that are useful as such therapeutic agents.

BACKGROUND

Since the discovery of penicillin in the 1920s and streptomycin in the 1940s, many new compounds have been discovered or specifically designed for use as antibiotic agents. It was once believed that infectious diseases could be completely controlled or eradicated with the use of such therapeutic agents. However, such beliefs have been shaken by the fact that strains of cells or microorganisms resistant to currently effective therapeutic agents continue to evolve. In fact, virtually every antibiotic agent developed for clinical use has ultimately encountered problems with the emergence of resistant bacteria. For example, resistant strains of Gram-positive bacteria such as methicillin-resistant staphylocci, penicillin-resistant streptococci, and vancomycin-resistant enterococci have developed, which can cause serious and even fatal results for patients infected with such resistant bacteria. Bacteria that are resistant to macrolide antibiotics, i.e., antibiotics based on a 14- to 16-membered lactone ring, have developed. Also, resistant strains of Gram-negative bacteria such as *H. influenzae* and *M. catarrhalis* have been identified. See, e.g., F. D. Lowry, "Antimicrobial Resistance: The Example of *Staphylococcus aureus*," *J. Clin. Invest.*, vol. 1H, no. 9, pp. 1265-1273 (2003); and Gold, H. S. and Moellering, R. C., Jr., "Antimicrobial-Drug Resistance," *N Engl. J. Med.*, vol. 335, pp. 1445-53 (1996).

The problem of resistance is not limited to the area of anti-infective agents, because resistance has also been encountered with anti-proliferative agents used in cancer chemotherapy. Therefore, there exists a need for new anti-infective and anti-proliferative agents that are both effective against resistant bacteria and resistant strains of cancer cells.

In the antibiotic area, despite the problem of increasing antibiotic resistance, no new major classes of antibiotics have been developed for clinical use since the approval in the United States in 2000 of the oxazolidinone ring-containing antibiotic, N-[[(5S)-3-[3-fluoro-4-(4-morpholinyl)phenyl]-2-oxo-5-oxazolidinyl]methyl acetamide, which is known as linezolid and is sold under the trade name ZYVOX®. See, R. C. Moellering, Jr., "Linezolid: The First Oxazolidinone Antimicrobial," *Annals of Internal Medicine*, vol. 138, no. 2, pp. 135-142 (2003).

Linezolid was approved for use as an anti-bacterial agent active against Gram-positive organisms. Unfortunately, linezolid-resistant strains of organisms are already being reported. See, Tsiodras et al., *Lancet*, vol. 358, p. 207 (2001); Gonzales et al., *Lancet*, vol. 357, p. 1179 (2001); Zurenko et al., *Proceedings Of The 39th Annual Interscience Conference On Antibacterial Agents And Chemotherapy (ICAAC)*, San Francisco, Calif., USA (Sep. 26-29, 1999). Because linezolid is both a clinically effective and commercially significant anti-microbial agent, investigators have been working to develop other effective linezolid derivatives.

Notwithstanding the foregoing, there is an ongoing need for new anti-infective and anti-proliferative agents. Furthermore, because many anti-infective and anti-proliferative agents have utility as anti-inflammatory agents and prokinetic agents, there is also an ongoing need for new compounds useful as anti-inflammatory and prokinetic agents. Because of these needs for these therapeutic agents there is a corresponding need for processes for making these compounds and key intermediates in the synthesis thereof.

SUMMARY OF THE INVENTION

The present invention relates to processes for preparing triazole compounds, particularly 1,2,3-triazole compounds, i.e. compounds in which the three nitrogens of the triazole ring are in the adjacent "1", "2", and "3" positions.

The processes of the invention can tolerate a wide variety of functional groups, so various substituted starting materials can be used. The processes generally provide the desired final triazole compound at or near the end of the overall process, although it may be desirable in certain instances to further convert the compound to a pharmaceutically acceptable salt, ester, or prodrug thereof.

The foregoing and other aspects and embodiments of the invention can be more fully understood by reference to the following detailed description and claims.

DETAILED DESCRIPTION OF THE INVENTION

The present invention relates to processes for preparing triazole compounds, particularly 1,2,3-triazole compounds, i.e. compounds in which the three nitrogens of the triazole ring are in the adjacent "1", "2", and "3" positions. The present invention also relates to the intermediate compounds for preparing these triazole compounds.

The triazoles are connected to the remainder of the molecule, typically at the "4" position, i.e. at one of the remaining carbon atoms of the triazole ring. It should be noted that this numbering convention is used for convenience, and that the exact numbering will depend on the numbering convention used, and is not intended as a limitation. The important aspects of the triazoles of the present invention are that (a) the nitrogen atoms of the triazole ring are in an adjacent or "1", "2", and "3" orientation and (b) the triazole is attached to the remainder of the molecule via one of the remaining two carbon atoms of the triazole ring.

The following examples further illustrate this point and also provide an example of a numbering system for the triazole ring.

An exemplary numbering scheme for triazole, Compound A, is a follows:

Compound A

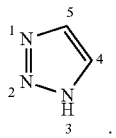

An nonlimiting example of a triazole compound, Compound B (also compound 1 of Table 1), of the present invention, showing a numbering convention in which the triazole ring is attached at the "4" position to the remainder of the compound, and where the remaining carbon atom at position "5" of the triazole ring is unsubstituted, i.e. where it has a hydrogen, is as follows:

Compound B

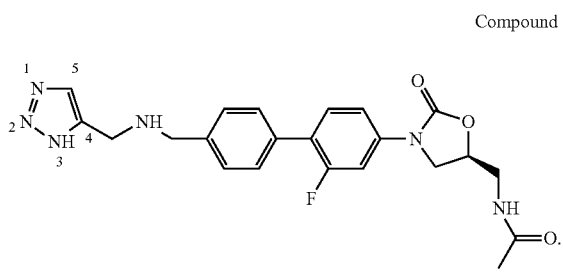

It should be recognized that the triazole ring is a 5-membered heteroaromatic ring and that the location of the two double bonds drawn in most representations is an arbitrary depiction of one of the multiple structures that can be drawn, and is used for convenience and not intended as a limitation. In fact, five different structures, sometimes called tautomeric structures, can be drawn to depict a 1,2,3-triazole. These tautomeric structures can be indicated with double-headed arrows between each structure, indicating that the molecules so represented are in equilibrium with each other. As a nonlimiting example, the following structures can be used to depict the compounds 1,2,3-triazole.

Tautormeric Structures for 1,2,3-triazole, Compound A

For example, for Compound B, the following tautomeric structures can be drawn:

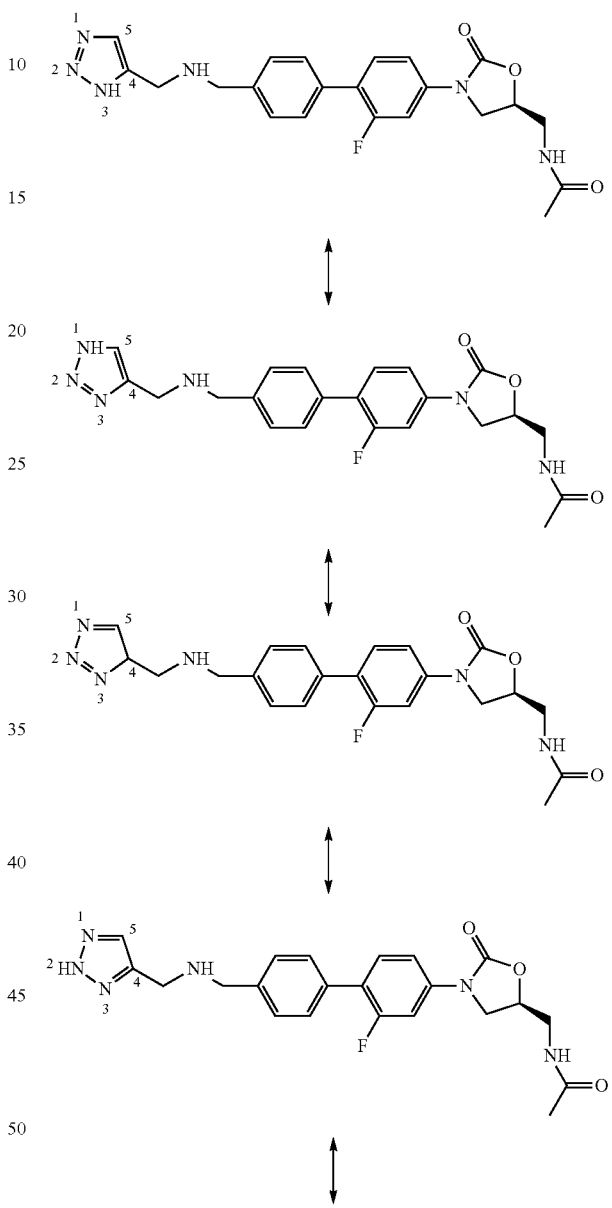

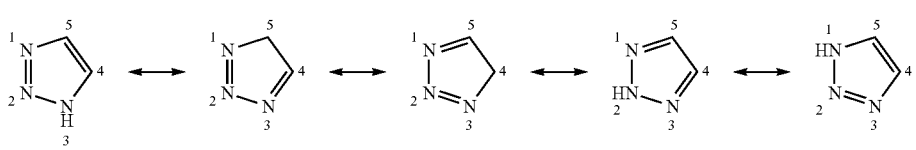

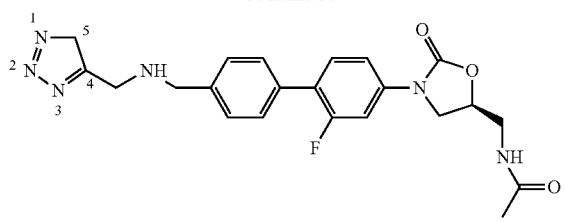

Tautomeric Structures for Compound B

The triazole compounds of the present invention are useful as pharmaceutical agents, particularly as anti-infective agents and/or as anti-proliferative agents, for treating humans and animals, particularly for treating humans and other mammals. The compounds may be used without limitation, for example, as anti-cancer, anti-microbial, anti-bacterial, anti-fungal, anti-parasitic and/or anti-viral agents. Further, the present invention provides a family of compounds that can be used without limitation as anti-inflammatory agents, for example, for use in treating chronic inflammatory airway diseases, and/or as prokinetic agents, for example, for use in treating gastrointestinal motility disorders such as gastroesophageal reflux disease, gastroparesis (diabetic and post surgical), irritable bowel syndrome, and constipation. Further, the compounds can be used to treat or prevent a disease state in a mammal caused or mediated by a nonsense or missense mutation.

Following synthesis, a therapeutically effective amount of one or more of the compounds can be formulated with a pharmaceutically acceptable carrier for administration to a human or an animal. Accordingly, the compounds or the formulations can be administered, for example, via oral, parenteral, or topical routes, to provide an effective amount of the compound. In alternative embodiments, the compounds prepared in accordance with the present invention can be used to coat or impregnate a medical device, e.g., a stent.

Compounds synthesized according to the methods of the invention may be used to treat a disorder in a mammal, particularly humans, by administering to the mammal an effective amount of one or more compounds of the invention thereby to ameliorate a symptom of a particular disorder. Such a disorder can be selected from a skin infection, nosocomial pneumonia, post-viral pneumonia, an abdominal infection, a urinary tract infection, bacteremia, septicemia, endocarditis, an atrio-ventricular shunt infection, a vascular access infection, meningitis, surgical prophylaxis, a peritoneal infection, a bone infection, a joint infection, a methicillin-resistant Staphylococcus aureus infection, a vancomycin-resistant Enterococci infection, a linezolid-resistant organism infection, and tuberculosis.

1. DEFINITIONS

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Keto substituents are not present on aromatic moieties. Ring double bonds, as used herein, are double bonds that are formed between two adjacent ring atoms (e.g., C=C, C=N, or N=N).

The present invention is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

The compounds described herein may have asymmetric centers, Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic, and geometric isomeric forms of a structure are intended, unless the specific stereochemistry or isomeric form is specifically indicated. All tautomers of shown or described compounds are also considered to be part of the present invention.

When any variable (e.g., R') occurs more than one time in any constituent or formula for a compound, its definition at each occurrence is independent of its definition at every other occurrence. Thus, for example, if a group is shown to be substituted with 0-2 $R^1$ moieties, then the group may optionally be substituted with up to two $R^1$ moieties and $R^1$ at each occurrence is selected independently from the definition of $R^1$. Also, combinations of substituents and/or variables are permissible, but only if such combinations result in stable compounds.

When a bond to a substituent is shown to cross a bond connecting two atoms in a ring, then such substituent may be bonded to any atom in the ring. When a substituent is listed without indicating the atom via which such substituent is bonded to the rest of the compound of a given formula, then such substituent may be bonded via any atom in such substituent. Combinations of substituents and/or variables are permissible, but only if such combinations result in stable compounds.

When an atom or chemical moiety is followed by a subscripted numeric range (e.g., $C_{1-6}$), the invention is meant to encompass each number within the range as well as all intermediate ranges. For example, "$C_{1-6}$ alkyl" is meant to include alkyl groups with 1, 2, 3, 4, 5, 6, 1-6, 1-5, 1-4, 1-3, 1-2, 2-6, 2-5, 2-4, 2-3, 3-6, 3-5, 3-4, 4-6, 4-5, and 5-6 carbons.

As used herein, "alkyl" is intended to include both branched and straight-chain saturated aliphatic hydrocarbon groups having the specified number of carbon atoms. For example, $C_{1-6}$ alkyl is intended to include $C_1$, $C_2$, $C_3$, $C_4$, $C_5$, and $C_6$ alkyl groups. Examples of alkyl include, but are not limited to, methyl, ethyl, n-propyl, i-propyl, n-butyl, s-butyl, t-butyl, n-pentyl, s-pentyl, and n-hexyl.

As used herein, "alkenyl" is intended to include hydrocarbon chains of either straight or branched configuration having one or more carbon-carbon double bonds occurring at any stable point along the chain. For example, $C_{2-6}$ alkenyl is intended to include $C_2$, $C_3$, $C_4$, $C_5$, and $C_6$ alkenyl groups. Examples of alkenyl include, but are not limited to, ethenyl and propenyl.

As used herein, "alkynyl" is intended to include hydrocarbon chains of either straight or branched configuration having one or more carbon-carbon triple bonds occurring at any stable point along the chain. For example, $C_{2-6}$ alkynyl is intended to include $C_2$, $C_3$, $C_4$, $C_5$, and $C_6$ alkynyl groups. Examples of alkynyl include, but are not limited to, ethynyl and propynyl.

As used herein, "halo" or "halogen" refers to fluoro, chloro, bromo, and iodo.

"Counterion" is used to represent a small, negatively charged species such as chloride, bromide, hydroxide, acetate, and sulfate.

As used herein, "carbocycle" or "carbocyclic ring" is intended to mean any stable monocyclic, bicyclic, or tricyclic ring having the specified number of carbons, any of which may be saturated, unsaturated, or aromatic. For example a $C_{3-14}$ carbocycle is intended to mean a mono-, bi-, or tricyclic ring having 3, 4, 5, 6, 7, 8, 9, 10, 11, 12, 13, or 14 carbon atoms. Examples of carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, fluorenyl, phenyl, naphthyl, indanyl, adamantyl, and tetrahydronaphthyl. Bridged rings are also included in the definition of carbocycle, including, for example, [3.3.0]bicyclooctane, [4.3.0]bicyclononane, [4.4.0]bicyclodecane, and [2.2.2]bicyclooctane. A bridged ring occurs when one or more carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge. Fused (e.g., naphthyl and tetrahydronaphthyl) and Spiro rings are also included.

As used herein, the term "heterocycle" or "heterocyclic" is intended to mean any stable monocyclic, bicyclic, or tricyclic ring which is saturated, unsaturated, or aromatic and comprises carbon atoms and one or more ring heteroatoms, e.g., 1 or 1-2 or 1-3 or 1-4 or 1-5 or 1-6 heteroatoms, independently selected from nitrogen, oxygen, and sulfur. A bicyclic or tricyclic heterocycle may have one or more heteroatoms located in one ring, or the heteroatoms may be located in more than one ring. The nitrogen and sulfur heteroatoms may optionally be oxidized (i.e., N→O and $S(O)_p$, where p=1 or 2). When a nitrogen atom is included in the ring it is either N or NH, depending on whether or not it is attached to a double bond in the ring (i.e., a hydrogen is present if needed to maintain the tri-valency of the nitrogen atom). The nitrogen atom may be substituted or unsubstituted (i.e., N or NR wherein R is H or another substituent, as defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. Bridged rings are also included in the definition of heterocycle. A bridged ring occurs when one or more atoms (i.e., C, O, N, or S) link two non-adjacent carbon or nitrogen atoms. Bridges include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge. Spiro and fused rings are also included.

As used herein, the term "aromatic heterocycle" or "heteroaryl" is intended to mean a stable 5, 6, or 7-membered monocyclic or bicyclic aromatic heterocyclic ring or 7, 8, 9, 10, 11, or 12-membered bicyclic aromatic heterocyclic ring which consists of carbon atoms and one or more heteroatoms, e.g., 1 or 1-2 or 1-3 or 1-4 or 1-5 or 1-6 heteroatoms, independently selected from nitrogen, oxygen, and sulfur. In the case of bicyclic heterocyclic aromatic rings, only one of the two rings needs to be aromatic (e.g., 2,3-dihydroindole), though both may be (e.g., quinoline). The second ring can also be fused or bridged as defined above for heterocycles. The nitrogen atom may be substituted or unsubstituted (i.e., N or NR wherein R is H or another substituent, as defined). The nitrogen and sulfur heteroatoms may optionally be oxidized (i.e., N→O and $S(O)_p$, where p=1 or 2). It is to be noted that total number of S and O atoms in the aromatic heterocycle is not more than 1.

Examples of heterocycles include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

As used herein, the term "amine protecting group" is intended to mean a functional group that converts an amine, amide, or other nitrogen-containing moiety into a different chemical group that is substantially inert to the conditions of a particular chemical reaction. Amine protecting groups are preferably removed easily and selectively in good yield under conditions that do not affect other functional groups of the molecule. Examples of amine protecting groups include, but are not limited to, benzyl, t-butyldimethylsilyl, t-butdyldiphenylsilyl, t-butyloxycarbonyl, p-methoxybenzyl, methoxymethyl, tosyl, trifluoroacetyl, trimethylsilyl, fluorenylmethyloxycarbonyl, trimethylsilyl-ethyoxycarbonyl, 1-methyl-1-(4-biphenylyl)ethoxycarbonyl, allyloxycarbonyl, and benzyloxycarbonyl. Other suitable amine protecting groups are straightforwardly identified by those of skill in the art, e.g., by reference to Green & Wuts, *Protective Groups in Organic Synthesis,* 3d Ed. (1999, John Wiley & Sons, Inc.).

"Stable compound" and "stable structure" are meant to indicate a compound that is sufficiently robust to survive isolation to a useful degree of purity from a reaction mixture, and formulation into an efficacious therapeutic agent.

As used herein, the phrase "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, 2,3,4,5-tetrahydroxyhexane-1,6-dicarboxylic, 2,5-dihydroxybenzoic, acetic, adipic, ascorbic, benzene sulfonic, benzoic, bicarbonic, carbonic, citric, edetic, ethane disulfonic, ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, hyppuric, isethionic, lactic, lactobionic, lauryl sulfonic, maleic, malic, malonic, mandelic, methane sulfonic, napsylic, naphthalenedisulfonic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, and toluene sulfonic (e.g. p-toluene sulfonic) acid.

The pharmaceutically acceptable salts of the present invention can be synthesized from a parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 18th ed. (Mack Publishing Company, 1990). For example, salts can include, but are not limited to, the hydrochloride and acetate salts of the aliphatic amine-containing, hydroxyl amine-containing, and imine-containing compounds of the present invention.

Additionally, the compounds of the present invention, and particularly the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

Pharmaceutically acceptable ester means an esterified carboxylic acid moiety (i.e. esterified or reacted with a pharmaceutically acceptable alcohol) or esterified hydroxyl moiety (i.e. esterified or reacted with a pharmaceutically acceptable carboxylic acid) of the compounds and intermediates of the present invention.

Since prodrugs are known to enhance numerous desirable qualities of pharmaceuticals (e.g., solubility, bioavailability, manufacturing, etc.) the compounds of the present invention can be delivered in prodrug form. Thus, the present invention is intended to cover prodrugs of the presently claimed compounds, methods of delivering the same and compositions containing the same. "Prodrugs" are intended to include any covalently bonded carriers that release an active parent drug of the present invention in vivo when such prodrug is administered to a mammalian subject. Prodrugs the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, cleaves to form a free hydroxyl, free amino, or free sulfhydryl group, respectively. Examples of prodrugs include, but are not limited to, acetate, formate, and benzoate derivatives of alcohol and amine functional groups in the compounds of the present invention.

All pharmaceutically acceptable salts, esters, and prodrugs of the compounds of the present invention, and of their intermediates are contemplated as within the scope of the present invention.

All percentages and ratios used herein, unless otherwise indicated, are by weight.

Throughout the description, where compositions are described as having, including, or comprising specific components, it is contemplated that compositions also consist essentially of, or consist of, the recited components. Similarly, where processes are described as having, including, or comprising specific process steps, the processes also consist essentially of, or consist of, the recited processing steps. Further, the process steps are numbered for convenience in a claim or group of dependent claims. Moreover, two or more steps or actions may be conducted simultaneously. Additionally, single steps, or less than all the steps, or various permutations of the steps of the present invention can also be conducted and are contemplated within the present invention. It should be recognized that the steps and compound numbers as labeled in the processes of the present invention are provided for convenience and not intended to limit the scope of the invention.

2. PROCESSES OF THE INVENTION

The processes of the present invention involve a cycloaddition reaction of an azide and an alkyne to form a triazole moiety (e.g., step 1). Generally, the cycloaddition reaction is conducted at an elevated temperature, i.e. with the addition of heat, because when the reaction is run at normal room temperature or at a slightly elevated temperature, i.e. slightly above normal room temperature, the reaction tends not to go to completion, or sometimes not at all.

Alternatively, the cycloaddition reaction (e.g., step 1) can be run in the presence of a copper catalyst, in such instances the addition of heat not being necessary. The copper catalyst is preferably a copper (I) catalyst, examples of preferred copper catalysts being CuCl, CuBr, CuI, $CuNO_3$, and $Cu_2SO_4$, with CuI being most preferred. However, the copper catalyzed reaction has some potential safety concerns because of the danger of having an azide in the presence of copper, which can potentially trigger an explosive decomposition of the azide. Therefore, it is preferred that the cycloaddition reaction to form the triazole be carried out without a copper catalyst. When the reaction is carried out without a catalyst, the reaction has the advantage that it can be facilitated by heating, i.e. run under thermal conditions.

Because the triazole moiety can be relatively reactive, it is preferable to protect or mask the triazole so that further chemical transformations can be carried out on other parts of the molecule. In other words, even though an unsubstituted organic triazole can be made by the cycloaddition of an inorganic azide, e.g. sodium azide, and an alkyne, it is preferable to make a masked or protected azide, which is subsequently unmasked or deprotected.

Therefore, the processes of the present invention involve the synthesis of a masked triazole, i.e. a protected triazole, which is further reacted on another part of the molecule to make a biaryl moiety. Specifically, in the processes of the present invention, the biaryl moiety is preferably made by a Suzuki type coupling reaction (e.g., step 3). The biaryl adduct made from the Suzuki type coupling can then either be deprotected to release or unmask the triazole, or it can first be subjected to further chemical transformations.

Generally the invention relates to a process for preparing a compound having the formula:

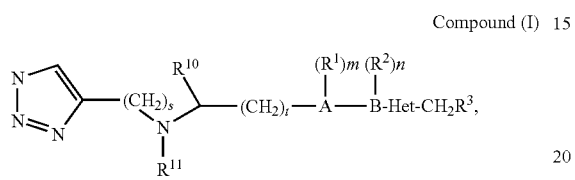

Compound (I)

wherein the process includes the steps of:

(Step 1) combining a compound (II) having the formula:

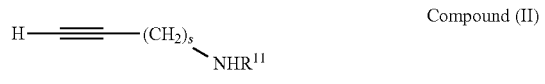

Compound (II)

with a compound (III) having the formula:

X—N$_3$    Compound (III)

in a solvent, optionally in the presence of a copper catalyst, to form a compound (IV) having the formula:

Compound (IV)

(Step 2) combining a compound (IV) with a compound (V) having the formula:

Compound (V)

in a solvent in the presence of a reducing agent to form a compound (VI) having the formula:

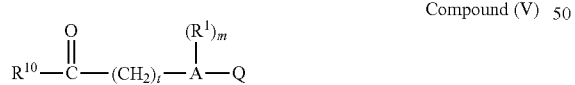

Compound (VI)

(Step 3) combining compound (VI) with a compound (VII) having the formula:

Compound (VII)

in a solvent in the presence of a base and a palladium catalyst to form a compound (VIII) having the formula:

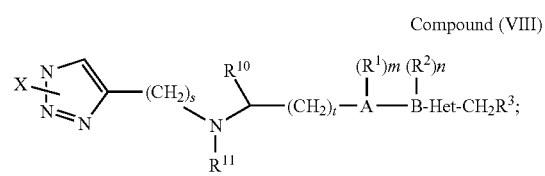

Compound (VIII)

and (Step 4) heating a compound (VIII), in a solvent in the presence of an acid, followed by the addition of a neutralizing agent to form a compound (I);

wherein:
A is selected from phenyl, pyridyl, pyrazinyl, pyrimidinyl, and pyridazinyl;
B is selected from phenyl, pyridyl, pyrazinyl, pyrimidinyl, and pyridazinyl;
Het-CH$_2$—R$^3$ is selected from

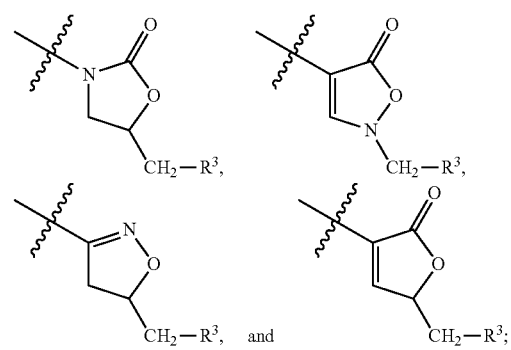

Q is a borane having the formula —BY$_2$, wherein
Y, at each occurrence, independently is selected from:
a) —OH, b) —OC$_{1-6}$ alkyl, c) —OC$_{2-6}$ alkenyl, d) —OC$_{2-6}$ alkynyl, e) —OC$_{1-14}$ saturated, unsaturated, or aromatic carbocycle, f) C$_{1-6}$ alkyl, g) C$_{2-6}$alkenyl, h) C$_{2-6}$ alkynyl, and i) C$_{1-14}$ saturated, unsaturated, or aromatic carbocycle,
wherein any of b)-i) optionally is substituted with one or more halogens;
alternatively, two Y groups taken together comprise a chemical moiety selected from: a) —OC(R$^4$)(R$^4$)C(R$^4$)(R$^4$)O—, and b) —OC(R$^4$)(R$^4$)CH$_2$C(R$^4$)(R$^4$)O—;
alternatively, Q is a BF$_3$ alkali metal salt, a BF$_3$ ammonium salt, a BF$_3$ tetralkyl ammonium salt, a BF$_3$ phosphate salt, or 9-borabicyclo[3.3.1]nonane;
X is selected from:
a) —CH$_2$-phenyl, b) —SO-phenyl, c) —SO$_2$-phenyl, d) —CH$_2$—O-phenyl, e) —CH$_2$—O—CH$_2$-phenyl, f) —CH$_2$—O—R$^{21}$, g) —Si—(R$^{21}$)$_3$, and h) —P(O)—(W)$_2$, wherein each W is independently $C_{1-6}$ alkyl or phenyl; each $R^{21}$ is independently $C_{1-6}$ alkyl; each phenyl in a), b), c), d), e), or h) is optionally substituted with one or more $R^{12}$, wherein $R^{12}$ is selected from:
a) F, b) Cl, c) Br, d) I, e) —$CF_3$, f) —$OR^{22}$, g) —CN, h) —$NO_2$, i) —$NR^{22}R^{22}$, j) —$C(O)R^{22}$, k) —C(O)$OR^{22}$, l) —$OC(O)R^{22}$, m) —$C(O)NR^{22}R^{22}$, n) —$NR^{22}C(O)R^{22}$, o) —$OC(O)NR^{22}R^{22}$, p) —$NR^{22}C(O)OR^{22}$, q) —$NR^{22}C(O)NR^{22}R^{22}$, r) —$C(S)R^{22}$, s) —$C(S)OR^{22}$, t) —$OC(S)R^{22}$, u) —$C(S)NR^{22}R^{22}$, v) —$NR^{22}C(S)R^{22}$, w) —$OC(S)NR^{22}R^{22}$, x) —$NR^{22}C(S)OR^{22}$, y) —$NR^{22}C(S)NR^{22}R^{22}$, z) —$C(NR^{22})R^{22}$, aa) —$C(NR^{22})OR^{22}$, bb) —$OC(NR^{22})R^{22}$, cc) —$C(NR^{22})NR^{22}R^{22}$, dd) —$NR^{22}C(NR^{22})R^{22}$, ee) —$OC(NR^{22})NR^{22}R^{22}$, ff) —$NR^{22}C(NR^{22})OR^{22}$, gg) —$NR^{22}C(NR^{22})NR^{22}R^{22}$, hh) —$S(O)_pR^{22}$, ii) —$SO_2NR^{22}R^{22}$ and jj) $R^{22}$, wherein each $R^{22}$ is independently, H or $C_{1-6}$ alkyl;

Z is selected from: a) I, b) Br, c) Cl, d) $R^9OSO_3$—, and e) $N_2BF_4$;

$R^1$, at each occurrence, independently is selected from:
a) F, b) Cl, c) Br, d) I, e) —$CF_3$, f) —$OR^4$, g) —CN, h) —$NO_2$, i) —$NR^4R^4$, j) —$C(O)R^4$, k) —$C(O)OR^4$, l) —$OC(O)R^4$, m) —$C(O)NR^4R^4$, n) —$NR^4C(O)R^4$, o) —$OC(O)NR^4R^4$, p) —$NR^4C(O)OR^4$, q) —$NR^4C(O)NR^4R^4$, r) —$C(S)R^4$, s) —$C(S)OR^4$, t) —$OC(S)R^4$, u) —$C(S)NR^4R^4$, v) —$NR^4C(S)R^4$, w) —$OC(S)NR^4R^4$, x) —$NR^4C(S)OR^4$, y) —$NR^4C(S)NR^4R^4$, z) —$C(NR^4)R^4$, aa) —$C(NR^4)OR^4$, bb) —$OC(NR^4)R^4$, cc) —$C(NR^4)NR^4R^4$, dd) —$NR^4C(NR^4)R^4$, ee) —$OC(NR^4)NR^4R^4$, ff) —$NR^4C(NR^4)OR^4$, gg) —$NR^4C(NR^4)NR^4R^4$, hh) —$S(O)_pR^4$, ii) —$SO_2NR^4R^4$, and jj) $R^4$;

$R^2$, at each occurrence, independently is selected from:
a) F, b) Cl, c) Br, d) I, e) —$CF_3$, f) —$OR^4$, g) —CN, h) —$NO_2$, i) —$NR^4R^4$, j) —$C(O)R^4$, k) —$C(O)OR^4$, l) —$OC(O)R^4$, m) —$C(O)NR^4R^4$, n) —$NR^4C(O)R^4$, o) —$OC(O)NR^4R^4$, p) —$NR^4C(O)OR^4$, q) —$NR^4C(O)NR^4R^4$, r) —$C(S)R^4$, s) —$C(S)OR^4$, t) —$OC(S)R^4$, u) —$C(S)NR^4, R^4$, v) —$NR^4C(S)R^4$, w) —$OC(S)NR^4R^4$, x) —$NR^4C(S)OR^4$, y) —$NR^4C(S)NR^4R^4$, —$C(NR^4)R^4$, aa) —$C(NR^4)OR^4$, bb) —$OC(NR^4)R^4$, cc) —$C(NR^4)NR^4R^4$, dd) —$NR^4C(NR^4)R^4$, ee) —$OC(NR^4)NR^4R^4$, ff) —$NR^4C(NR^4)OR^4$, gg) —$NR^4C(NR^4)NR^4R^4$, hh) —$S(O)_pR^4$, ii) —$SO_2NR^4R^4$, and jj) $R^4$;

$R^3$ is selected from:
a) —$OR^4$, b) —$NR^4R^4$, c) —$C(O)R^4$, d) —$C(O)OR^4$, e) —$OC(O)R^4$, f) —$C(O)NR^4R^4$, g) —$NR^4C(O)R^4$, —$OC(O)NR^4R^4$, i) —$NR^4C(O)OR^4$, j) —$NR^4C(O)NR^4R^4$, k) —$C(S)R^4$, l) —$C(S)OR^4$, m) —$OC(S)R^4$, n) —$C(S)NR^4R^4$, o) —$NR^4C(S)R^4$, p) —$OC(S)NR^4R^4$, q) —$NR^4C(S)OR^4$, r) —$NR^4C(S)NR^4R^4$, s) —$C(NR^4)R^4$, t) —$C(NR^4)OR^4$, u) —$OC(NR^4)R^4$, v) —$C(NR^4)NR^4R^4$, w) —$NR^4C(NR^4)R^4$, x) —$OC(NR^4)NR^4R^4$, y) —$NR^4C(NR^4)OR^4$, z) —$NR^4C(NR^4)NR^4R^4$, aa) —$S(O)_pR^4$, bb) —$SO_2NR^4R^4$, and cc) $R^4$;

$R^4$, at each occurrence, independently is selected from:
a) H, b) —$OR^6$, c) $C_{1-6}$ alkyl, d) $C_{2-6}$ alkenyl, e) $C_{2-6}$ alkynyl, f) $C_{3-14}$ saturated, unsaturated, or aromatic carbocycle, g) 3-14 membered saturated, unsaturated, or aromatic heterocycle comprising one or more heteroatoms selected from nitrogen, oxygen, and sulfur, b) —C(O)—$C_{1-6}$ alkyl, i) —C(O)—$C_{2-6}$ alkenyl, j) —C(O)—$C_{2-6}$ alkynyl, k) —C(O)—[$C_{3-14}$ saturated, unsaturated, or aromatic carbocycle], l) —C(O)-[3-14 membered saturated, unsaturated, or aromatic heterocycle comprising one or more heteroatoms selected from nitrogen, oxygen, and sulfur], m) —C(O)O—$C_{1-6}$ alkyl, n) —C(O)O—$C_{2-6}$ alkenyl, o) —C(O)O—$C_{2-6}$ alkynyl, p) —C(O)O—$C_{3-14}$ saturated, unsaturated, or aromatic carbocycle, and q) —C(O)O-3-14 membered saturated, unsaturated, or aromatic heterocycle comprising one or more heteroatoms selected from nitrogen, oxygen, and sulfur,
wherein any of c) q) optionally is substituted with one or more $R^5$ groups;

$R^5$, at each occurrence, is independently selected from:
a) F, b) Cl, c) Br, d) I, e) =O, f) =S, g) =$NR^6$, h) =$NOR^6$, i) =N—$NR^6R^6$, j) —$CF_3$, k) —$OR^6$, l) —CN, m) —$NO_2$, n) —$NR^6R^6$, o) —$C(O)R^6$, p) —$C(O)OR^6$, q) —$OC(O)R^6$, r) —$C(O)NR^6R^6$, s) —$NR^6C(O)R^6$, t) —$OC(O)NR^6R^6$, u) —$NR^6C(O)OR^6$, v) —$NR^6C(O)NR^6R^6$, w) —$C(S)R^6$, x) —$C(S)OR^6$, y) —$OC(S)R^6$, z) —$C(S)NR^6R^6$, aa) —$NR^6C(S)R^6$, bb) —$OC(S)NR^6R^6$, cc) —$NR^6C(S)OR^6$, dd) —$NR^6C(S)NR^6R^6$, ee) —$C(NR^6)R^6$, ff) —$C(NR^6)OR^6$, —$OC(NR^6)R^6$, hh) —$C(NR^6)NR^6R^6$, ii) —$NR^6C(NR^6)R^6$, jj) —$OC(NR^6)NR^6R^6$, kk) —$NR^6C(NR^6)OR^6$, ll) —$NR^6C(NR^6)NR^6R^6$, mm) —$S(O)_pR^6$, nn) —$SO_2NR^6R^6$, oo) —$N_3$, pp) —$Si(CH_3)_3$, qq) —O—$Si(CH_3)_3$, rr) —$Si(C_2H_5)_2CH_3$, ss) —O—$Si(C_2H_5)_2CH_3$, and tt) $R^6$;

$R^6$, at each occurrence, independently is selected from:
a) H, b) —$OR^8$, c) $C_{1-6}$ alkyl, d) $C_{2-6}$ alkenyl, e) $C_{2-6}$ alkynyl, f) $C_{3-14}$ saturated, unsaturated, or aromatic carbocycle, g) 3-14 membered saturated, unsaturated, or aromatic heterocycle comprising one or more heteroatoms selected from nitrogen, oxygen, and sulfur, h) —C(O)—$C_{1-6}$ alkyl, i) —C(O)—$C_{2-6}$ alkenyl, j) —C(O)—$C_{2-6}$ alkynyl, k) —C(O)—$C_{3-14}$ saturated, unsaturated, or aromatic carbocycle, l) —C(O)-3-14 membered saturated, unsaturated, or aromatic heterocycle comprising one or more heteroatoms selected from nitrogen, oxygen, and sulfur, m) —C(O)O—$C_{1-6}$ alkyl, n) —C(O)O—$C_{2-6}$ alkenyl, o) —C(O)O—$C_{2-6}$ alkynyl, p) —C(O)O—$C_{3-14}$ saturated, unsaturated, or aromatic carbocycle, and q) —C(O)O-3-14 membered saturated, unsaturated, or aromatic heterocycle comprising one or more heteroatoms selected from nitrogen, oxygen, and sulfur,
wherein any of c)-q) optionally is substituted with one or more $R^7$ groups;

$R^7$, at each occurrence, independently is selected from:
a) F, b) Cl, c) Br, d) I, e) =O, f) =S, g) =$NR^8$, h) =$NOR^8$, i) =N—$NR^8R^8$, j) —$CF_3$, k) —$OR^8$, l) —CN, m) —$NO_2$, n) —$NR^8R^8$, o) —$C(O)R^8$, p) —$C(O)OR^8$, q) —$OC(O)R^8$, r) —$C(O)NR^8R^8$, s) —$NR^8C(O)R^8$, t) —$OC(O)NR^8R^8$, u) —$NR^8C(O)OR^8$, v) —$NR^8C(O)NR^8R^8$, w) —$C(S)R^8$, x) —$C(S)OR^8$, y) —$OC(S)R^8$, z) —$C(S)NR^8R^8$, aa) —$NR^8C(S)R^8$, bb) —$OC(S)NR^8R^8$, cc) —$NR^8C(S)OR^8$, dd) —$NR^8C(S)NR^8R^8$, ee) —$C(NR^8)R^8$, ff) —$C(NR^8)OR^8$, gg) —$OC(NR^8)R^8$, hh) —$C(NR^8)NR^8R^8$, ii) —$NR^8C(NR^8)R^8$, jj) —$OC(NR^8)NR^8R^8$, kk) —$NR^8C(NR^8)OR^8$, ll) —$NR^8C(NR^8)NR^8R^8$, mm) —$S(O)_pR^8$, nn) —$SO_2NR^8R^8$, oo) $C_{1-6}$ alkyl, pp) $C_{2-6}$ alkenyl, qq) $C_{2-6}$ alkynyl, rr) $C_{3-14}$ saturated, unsaturated, or aromatic carbocycle, and ss) 3-14 membered saturated, unsaturated, or aromatic heterocycle comprising one or more heteroatoms selected from nitrogen, oxygen, and sulfur, wherein any of oo)-ss) optionally is substituted with one or more moieties selected from $R^8$, F, Cl, Br, I, $-CF_3$, $-OR^8$, $-SR^8$, $-CN$, $-NO_2$, $-NR^8R^8$, $-C(O)R^8$, $-C(O)OR^8$, $-OC(O)R^8$, $-C(O)NR^8R^8$, $-NR^8C(O)R^8$, $-OC(O)NR^8R^8$, $-NR^8C(O)OR^8$, $-NR^8C(O)NR^8R^8$, $-C(S)R^8$, $-C(S)OR^8$, $-OC(S)R^8$, $-C(S)NR^8R^8$, $-NR^8C(S)R^8$, $-OC(S)NR^8R^8$, $-NR^8C(S)OR^8$, $-NR^8C(S)NR^8R^8$, $-C(NR^8)R^8$, $-C(NR^8)OR^8$, $-OC(NR^8)R^8$, $-C(NR^8)NR^8R^8$, $-NR^8C(NR^8)R^8$, $-OC(NR^8)NR^8R^8$, $-NR^8C(NR^8)OR^8$, $-NR^8C(NR^8)NR^8R^8$, $-SO_2NR^8R^8$, and $-S(O)_pR^8$;

$R^8$, at each occurrence, independently is selected from:
a) H, b) an amine protecting group, c) $C_{1-6}$ alkyl, d) $C_{2-6}$ alkenyl, e) $C_{2-6}$ alkynyl, f) $C_{3-14}$ saturated, unsaturated, or aromatic carbocycle, g) 3-14 membered saturated, unsaturated, or aromatic heterocycle comprising one or more heteroatoms selected from nitrogen, oxygen, and sulfur, h) $-C(O)-C_{1-6}$ alkyl, i) $-C(O)-C_{2-6}$ alkenyl, j) $-C(O)-C_{2-6}$ alkynyl, k) $-C(O)-C_{3-14}$ saturated, unsaturated, or aromatic carbocycle, l) $-C(O)$-3-14 membered saturated, unsaturated, or aromatic heterocycle comprising one or more heteroatoms selected from nitrogen, oxygen, and sulfur, m) $-C(O)O-C_{1-6}$ alkyl, n) $-C(O)O-C_{2-6}$ alkenyl, o) $-C(O)O-C_{2-6}$ alkynyl, p) $-C(O)O-C_{3-14}$ saturated, unsaturated, or aromatic carbocycle, and q) $-C(O)O$-3-14 membered saturated, unsaturated, or aromatic heterocycle comprising one or more heteroatoms selected from nitrogen, oxygen, and sulfur, wherein any of c)-q) optionally is substituted with one or more moieties selected from F, Cl, Br, I, $-CF_3$, $-OH$, $-OC_{1-6}$ alkyl, $-SH$, $-SC_{1-6}$ alkyl, $-CN$, $-NO_2$, $-NH_2$, $-NHC_{1-6}$ alkyl, $-N(C_{1-6}alkyl)_2$, $-C(O)C_{1-6}$ alkyl, $-C(O)OC_{1-6}$ alkyl, $-C(O)NH_2$, $-C(O)NHC_{1-6}$ alkyl, $-C(O)N(C_{1-6}$ alkyl$)_2$, $-NHC(O)C_{1-6}$ alkyl, $-SO_2NH_2-$, $-SO_2NHC_{1-6}$ alkyl, $-SO_2N(C_{1-6}$ alkyl$)_2$, and $-S(O)_pC_{1-6}$ alkyl;

$R^9$ is selected from: a) $C_{1-4}$ alkyl, b) phenyl, and c) toluyl, wherein any of a)-c) optionally is substituted with one or more moieties selected from F, Cl, Br, and I;

$R^{10}$ is selected from H and $C_{1-8}$ alkyl;
$R^{11}$ is selected from H and $C_{1-8}$ alkyl;
m is 0, 1, 2, 3, or 4;
n is 0, 1, 2, 3, or 4;
p, at each occurrence, independently is 0, 1, or 2;
s is 1, 2, 3, 4, 5, or 6; and
t is 0, 1, 2, 3, 4, 5, or 6,
wherein $-(CH_2)_s-$ and $-(CH_2)_t$, other than when t is 0, are optionally substituted on any carbon atom thereof by one or more moieties selected from a) $C_{1-6}$ alkyl, b) $C_{1-6}$ alkenyl, c) phenyl, d) hydroxyl, e) $C_{1-6}$ alkoxy, f) F, g) Cl, h) Br, i) I, j) =O, and k) benzyl.

As used in compound (I), (VIII), (VIII-b-P), (VIII-b), (I-b), B indicates the variable B, as defined above. However, as used in the borane compound Q, $(-BY_2)$, B indicates the element boron.

The azide compounds (e.g., Compound (III) utilized in step 1) useful in the present invention are designated as X—N3. A wide array of azide compounds is useful here. Specifically, X is selected from a) —CH2-phenyl, b) —SO-phenyl, c) —SO2-phenyl, d) —CH2-O-phenyl, e) —CH2-O—CH2-phenyl, f) —CH2-O—R21, g) —Si—(R21)3, and h) —P(O)—(W)2 (see definitions of variables above). In further embodiments, X is para-methoxybenzyl, para-toluenesulfo-nyl, trimethylsilyl, and diphenylphosphoryl. In yet further embodiments, X is para-methoxybenzyl.

In some embodiments, the process of the invention further comprises (Step 5): combining compound (I) with an acid to form a salt thereof.

In some embodiments, groups Q and Z can be reversed (e.g., Q is present in compound VII and Z is present in compound V) for the Suzuki coupling step of the present invention.

The invention further relates to a process for preparing a compound (I) having the formula Compound (I)

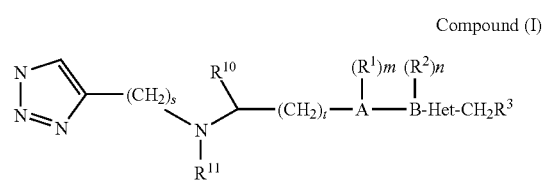

comprising the steps of:

(Step 1) combining a compound (II) having the formula:

Compound (II)

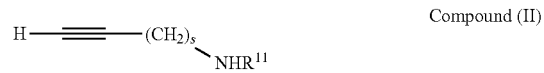

with a compound (III) having the formula:

X—N₃         Compound (III)

in a solvent, optionally in the presence of a copper catalyst, to form a compound (IV) having the formula:

Compound (IV)

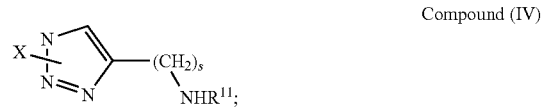

(Step 2) combining a compound (IV) with a compound (V-a) having the formula

Compound (V-a)

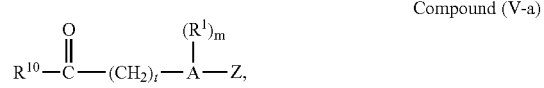

in a solvent in the presence of a reducing agent to form a compound (VI-a) having the formula:

Compound (VI-a)

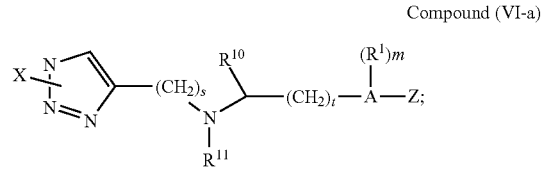

(Step 3) combining compound (VI-a) with a compound (VII-a) having the formula:

Compound (VII-a)

$$Q-B(R^2)_n-Het-CH_2-R^3$$

in a solvent in the presence of a base and a palladium catalyst to form a compound (VIII) having the formula, Compound (VIII)

[structure: X-triazole-(CH$_2$)$_s$-N(R$^{10}$)(R$^{11}$)-(CH$_2$)$_t$-A(R$^1$)$_m$-B(R$^2$)$_n$-Het-CH$_2$R$^3$]

(Step 4) heating a compound (VIII), in a solvent in the presence of an acid, followed by the addition of a neutralizing agent to form a compound (I);
wherein A, B, Het-CH$_2$—R$^3$, Q, Z, R$^1$, R$^2$, R$^3$, R$^{10}$, R$^{11}$, m, n, p, s, and t are as defined above.

In some embodiments, this process further comprises (Step 5): combining compound (I) with an acid to form a salt thereof.

Further, the invention relates to a process for preparing a compound (I) having the formula Compound (I)

[structure: triazole-(CH$_2$)$_s$-N(R$^{10}$)(R$^{11}$)-(CH$_2$)$_t$-A(R$^1$)$_m$-B(R$^2$)$_n$-Het-CH$_2$R$^3$]

comprising the step of (Step 4) heating a compound (VIII) having the formula:

Compound (VIII)

[structure: X-triazole-(CH$_2$)$_s$-N(R$^{10}$)(R$^{11}$)-(CH$_2$)$_t$-A(R$^1$)$_m$-B(R$^2$)$_n$-Het-CH$_2$R$^3$]

in a solvent in the presence of an acid, followed by the addition of a neutralizing agent to form a compound (I); wherein A, B, Het-CH$_2$—R$^3$, Q, Z, R$^1$, R$^2$, R$^3$, R$^{10}$, R$^{11}$, m, n, p, s, and t are as defined above. This process can further include (Step 5): combining a compound (I) with an acid to form a salt thereof.

Further, the invention relates to a process for preparing a compound (I-b) having the formula Compound (I-b)

[structure: triazole-(CH$_2$)$_s$-CH(R$^{10}$)-NH-(CH$_2$)$_t$-A(R$^1$)$_m$-B(R$^2$)$_n$-Het-CH$_2$R$^3$]

comprising the steps of:
(Step 1) combining a compound (II-b) having the formula:

Compound (II-b)

$$H-\equiv-(CH_2)_s-NH_2$$

with a compound (III) having the formula:

$$X-N_3 \quad \text{Compound (III)}$$

in a solvent, optionally in the presence of a copper catalyst, to form a compound (IV-b) having the formula:

Compound (IV-b)

[structure: X-triazole-(CH$_2$)$_s$-NH$_2$]

(Step 2) combining a compound (IV-b) with a compound (V) having the formula:

Compound (V)

$$R^{10}-\overset{O}{\underset{}{C}}-(CH_2)_t-A(R^1)_m-Q$$

in a solvent in the presence of a reducing agent to form compound (VI-b) having the formula Compound (VI-b)

[structure: X-triazole-(CH$_2$)$_s$-CH(R$^{10}$)-NH-(CH$_2$)$_t$-A(R$^1$)$_m$-Q]

(Step 2-1) combining a compound (VI-b) with a protecting group reagent in a solvent in the presence of a base to form protected compound (VI-b-P) having the formula Compound (VI-b-P)

[structure: X-triazole-(CH$_2$)$_s$-CH(R$^{10}$)-N(Protecting Group)-(CH$_2$)$_t$-A(R$^1$)$_m$-Q]

(Step 3) combining a compound (VI-b-P) with a compound (VII) having the formula:

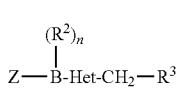

Compound (VII)

in a solvent in the presence of a base and a palladium catalyst to form compound (VIII-b-P) having the formula:

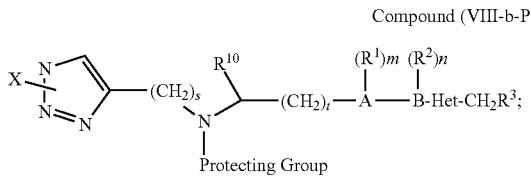

Compound (VIII-b-P)

(Step 3-1) deprotecting a compound (VIII-b-P) in a solvent to form compound (VIII-b) or a salt thereof having the formula:

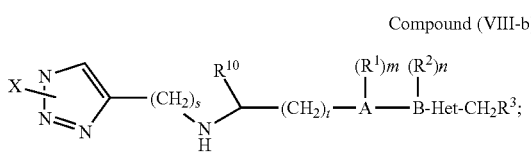

Compound (VIII-b)

(Step 4) heating compound (VIII-b) in a solvent in the presence of an acid, followed by the addition of a neutralizing agent to form compound (I-b);

wherein A, B, Het-CH$_2$—R$^3$, Q, Z, R$^1$, R$^2$, R$^3$, R$^{10}$, R$^{11}$, m, n, p, s, and t are as defined above. In some embodiments, this process further comprises (Step 5): combining compound (I-b) with an acid to form a salt thereof.

Further, the invention relates to a process for preparing a compound (I-b) having the formula

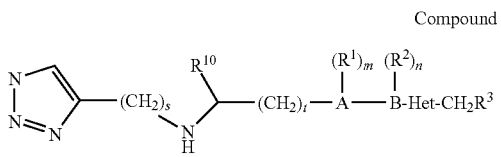

Compound (I-b)

comprising the steps of:
(Step 1) combining a compound (II-b) having the formula:

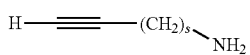

Compound (II-b)

with a compound (III) having the formula:

X—N$_3$

Compound (III)

in a solvent, optionally in the presence of a copper catalyst, to form a compound (IV-b) having the formula:

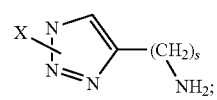

Compound (IV-b)

(Step 2) combining a compound (IV-b) with a compound (V) having the formula:

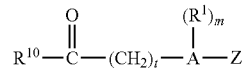

Compound (V)

in a solvent in the presence of a reducing agent to form compound (VI-b) having the formula

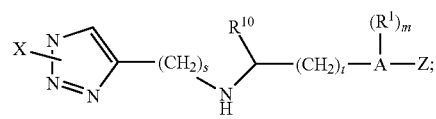

Compound (VI-b)

(Step 2-1) combining a compound (VI-a) with a protecting group reagent in a solvent in the presence of a base to form protected compound (VI-b-P) having the formula:

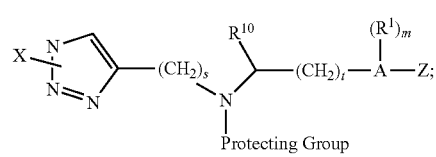

Compound (VI-b-P)

(Step 3) combining a compound (VI-b-P) with a compound (VII-a) having the formula:

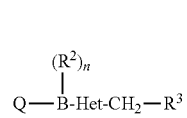

Compound (VII-a)

in a solvent in the presence of a base and a palladium catalyst to form compound (VIII-b-P) having the formula:

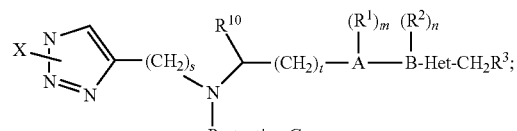

Compound (VIII-b-P)

(Step 3-1) deprotecting a compound (VIII-b-P) in a solvent in the presence of an acid to form compound (VIII-b) having the formula:

Compound (VIII-b)

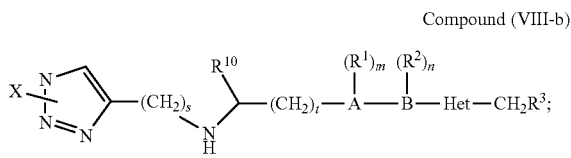

(Step 4) heating compound (VIII-b) in a solvent in the presence of an acid, followed by the addition of a neutralizing agent to form compound (I-b);
wherein A, B, Het-CH$_2$—R$^3$, Q, Z, R$^1$, R$^2$, R$^3$, R$^{10}$, R$^{11}$, m, n, p, s, and t are as defined above. This process can further include (Step 5) combining compound (I-b) with an acid to form a salt thereof.

Further, the invention relates to a process for preparing a compound having the formula:

Compound (IV)

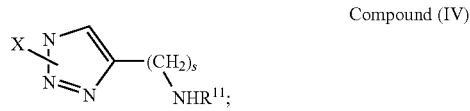

wherein the process includes the steps of:
(Step 1) combining a compound (II) having the formula:

Compound (II)

with a compound (III) having the formula:

X—N$_3$    Compound (III)

in a solvent, optionally in the presence of a copper catalyst, to form a compound (IV), wherein X, R$^{11}$, and s, are as defined above.

In some embodiments, the step 4 reaction is maintained at a temperature selected from about 40° C. to about 100° C. In some embodiments, the temperature of the step 4 reaction is between 60 and 70° C. For example, the reaction can be between 60 and 65° C. (inclusive) or between 65 and 70° C. (inclusive).

In some embodiments, the step 4 reaction is maintained at a temperature between 60 and 70° C. (inclusive) for 12 to 20 hours (inclusive) prior to the addition of a neutralizing agent. In some embodiments the reaction can be between 60 and 65° C. (inclusive) for about 20 hours and in some other embodiments the reaction can be between 65 and 70° C. (inclusive) for about 12 hours.

Note that in the foregoing that the substituent "X", when present, is shown as being on a variable position of the triazole ring, and is meant to represent that in the resulting intermediate triazole formed in Step 1 and carried through other steps, two different isomeric compounds can be produced. The "X" substituent in the intermediate triazole is subsequently removed in Step 4 to generally form a single compound.

Furthermore, because the compounds of the present invention not only have a triazole moiety, but also a biaryl moiety, the processes of the present invention involve a Suzuki-type coupling reaction, i.e. Step 3, between an aryl borane compound (e.g., an aryl boronic acid, aryl boronic ester, aryl boronic halide, or organoborane) and an aryl compound having an electronegative substituent (e.g., an aryl halide or aryl sulfonate) in a solvent in the presence of a base and a palladium catalyst. See, e.g., Miyaura et al., *Tetrahedron Letters*, 3437 (1979), and Miyaura & Suzuki, *Chem. Comm.*, 866 (1979). See for example PCT application No. WO 2005/012271, to Rib-X Pharmaceuticals, Inc., published Feb. 10, 2005; and Suzuki & Brown, *Organic Synthesis Via Boranes Volume 3: Suzuki Coupling*, (Aldrich, 2003).

In some embodiments, R$^{11}$ is H, i.e. the amine starting material is a primary amine. In these embodiments, the processes of the present invention involve additional optional steps of protecting the resulting secondary amine that is obtained after step (2) before carrying out the Suzuki type coupling on the compound to form the biaryl system. When the processes of the present invention include protecting the secondary amine, the protecting group is then generally removed, usually after the Suzuki type coupling is completed, and the remaining steps of the reaction can be carried out. Examples of suitable amine protecting groups include benzyl, t-butyldimethylsilyl, t-butdyldiphenylsilyl, t-butyloxycarbonyl, p-methoxybenzyl, methoxymethyl, tosyl, trifluoroacetyl, trimethylsilyl, fluorenyl-methyloxycarbonyl, 2-trimethylsilyl-ethyoxycarbonyl, 1-methyl-1-(4-biphenylypethoxycarbonyl, allyloxycarbonyl, and benzyloxycarbonyl. The addition and subsequent removal of the protecting groups is generally effected using well-known protecting group precursors, reagents, and reaction conditions. See T. W. Greene and P. G. M. Wuts, Protective Groups in Organic Synthesis, 3$^{rd}$ ed., John Wiley & Sons, New York, N.Y. (1999); and P. J. Kocienski and Georg Thieme, Protecting Groups, Verlag, New York, N.Y. (1994).

In some examples of the compounds of the invention, the Z group can be a halogen or a sulfonate. Examples of suitable sulfonates include, but are not limited to, methanesulfonate ("mesylate"), trifluoromethanesulfonate ("triflate"), and p-toluenesulfonate ("tosylate"). In preferred embodiments, the Z group is I. Q groups include, for example, —B(OH)$_2$, —BF$_2$.KF, and

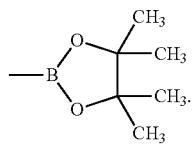

In any of the above processes, the base can be selected from alkali metal hydroxides, alkali metal carbonates, alkali metal fluorides, trialkyl amines, and mixtures thereof. Examples of suitable bases include potassium carbonate, sodium carbonate, sodium methoxide, sodium ethoxide, potassium fluoride, triethylamine, diisopropylethylamine, and mixtures thereof. In certain embodiments, the ratio of equivalents of base to equivalents of compound (I), (IV), (V), (V-a), (VIII), (VII-a), (IX), or (XII) is about 3:1.

The catalyst used in (Step 3) can be a palladium catalyst, for example, a ligand coordinated palladium(0) catalyst (e.g., a tetrakis(trialkylphosphine)palladium(0) or a tetrakis(triarylphosphine) palladium(0) catalyst) or a ligand coordinated palladium(II) catalyst. Suitable catalysts include, for example, tetrakis(triphenylphosphine)palladium(0), dichloro[1,1'-bis(diphenylphosphino)ferrocene]palladium(II), dichlorobis(triphenylphosphine)palladium(II), palladium(II)

acetate, and palladium(II) chloride. In particular embodiments, the catalyst is tetrakis(triphenylphosphine) palladium (0), and the ratio of the equivalents of the catalyst to the equivalents of the compound is about 1:20.

The solvent can be an aqueous solvent, or a mixture of water and an organic solvent, wherein the organic solvent is selected from methanol, ethanol, propanol, isopropanol, butanol, isobutanol, secondary butanol, tertiary butanol, benzene, toluene, tetrahydrofuran, dimethylformamide, 1,2-diethyl ether, dimethoxyethane, diisopropyl ether, methyltertiarybutyl ether, methoxymethyl ether, 2-methoxyethyl ether, 1,4-dioxane, 1,3-dioxolane, and mixtures thereof. In particular embodiments, the solvent is a mixture of water, toluene, and ethanol, for example, in a ratio of about 1:3:1 by volume.

The process can be carried out at a temperature of about 20° C. to about 100° C. In some embodiments, the process is carried out at the reflux temperature of the solvent.

Other reaction conditions for the Suzuki-type coupling reactions of the invention are identified by those of skill in the art, e.g., by reference to Suzuki & Brown, *Organic Synthesis Via Boranes Volume* 3: *Suzuki Coupling*, (Aldrich, 2003).

In some embodiments, Het-CH$_2$—R$^3$ is:

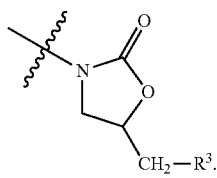

For example, Het-CH$_2$—R$^3$ can be:

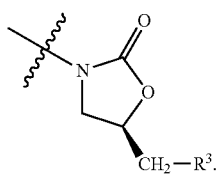

In some embodiments, the process of the invention involves compounds where: A is selected from phenyl and pyridyl; B is selected from phenyl and pyridyl; m is 0, 1, or 2; and n is 0, 1, or 2.

For example, the process of the invention involves compounds where: A is selected from phenyl and pyridyl; B is phenyl; m is 0; and n is 0, 1, or 2.

In certain embodiments, R$^3$ is —NHC(O)R$^4$.

In certain embodiments, wherein R$^4$ is selected from —CH$_3$, —CHCl$_2$, —CF$_2$H, —CH$_2$Cl, —CFH$_2$, —CFHCl, —CCl$_3$, and —CF$_3$. For example, R$^4$ can be —CH$_3$, —CF$_2$H, or —CCl$_2$H.

The process of the invention relates to compounds where R$^3$ is selected from triazole, tetrazole, oxazole, and isoxazole. For example, R$^3$ can be triazole. R$^3$ can be [1,2,3]triazol-1-yl.

In certain embodiments, R$^{10}$ is H and t is 0.

In certain embodiments, s can be 1.

In certain embodiments, R$^{11}$ can be H.

In certain embodiments, Z is selected from I, trifluoromethanesulfonate, and p-toluenesulfonate. For example, Z can be I.

In certain embodiments, Q is —B(OH)$_2$. In other embodiments, Q is:

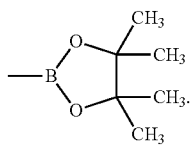

In further embodiments, Q is —BF$_2$.KF.

In some embodiments of the invention, X is selected from para-methoxybenzyl, para-toluenesulfonyl, trimethylsilyl, and diphenylphosphoryl. For example, X can be para-methoxybenzyl.

The solvent of (Step 1) can be, for example, toluene, dimethylformamide, dioxane, or tetrahydrofuran. For example, the solvent of (Step 1) is toluene.

(Step 1) can be carried out, for example, at a temperature between about 60° C. and about 130° C. For example, (Step 1) is carried out at a temperature between about 80° C. and about 120° C. (Step 1) can be carried out at a temperature of about 100° C.

In some embodiments, (Step 1) is carried out in the presence of a copper catalyst at a temperature of about 25° C. For example, the copper catalyst can be a copper (I) catalyst. The copper (I) catalyst can be selected from CuCl, CuBr, CuI, CuOAc, and Cu$_2$SO4 and mixtures thereof. In some embodiments, the (Step 1) copper catalyst is CuI.

The reducing agent of (Step 2) can be a boron reducing agent or a combination of a palladium catalyst and hydrogen. In one embodiment, the reducing agent of (Step 2) is a boron reducing agent, and can be sodium borohydride, sodium cyanoborohydride, sodium acetate borohydride, or mixtures thereof. For example, the boron reducing agent of (Step 2) is sodium acetate borohydride. In another embodiment, the reducing agent of (Step 2) is a combination of a palladium catalyst and hydrogen. For example, the palladium catalyst of (Step 2) is a palladium (0) catalyst. The palladium (0) catalyst of (Step 2) can be a palladium (0) on carbon catalyst.

The solvent of (Step 2) or (Step 2-1) can be, for example, methanol, ethanol, propanol, isopropanol, butanol, isobutanol, secondary butanol, tertiary butanol, dichloromethane, 1,1,-dichloroethane, tetrahydrofuran, dimethylformamide or mixtures thereof. For example, the solvent of (Step 2) or (Step 2-1) can be tetrahydrofuran.

The base of (Step 2-1) can be, for example, potassium carbonate, sodium carbonate, sodium methoxide, sodium ethoxide, potassium fluoride, triethylamine, diisopropylethylamine, or mixtures thereof. For example, the base of (Step 2-1) can be potassium carbonate.

The base of (Step 3) can be, for example, selected from alkali metal hydroxides, alkali metal carbonates, alkali metal fluorides, trialkyl amines, and mixtures thereof. For example, the base of (Step 3) can be selected from potassium carbonate, sodium carbonate, sodium, methoxide, sodium ethoxide, potassium fluoride, triethylamine, diisopropylethylamine, and mixtures thereof. For example, the base of (Step 3) can be potassium carbonate. In one embodiment, the ratio of equivalents of base of (Step 3) to equivalents of compound (VI) or compound (VI-a) is about 3:1.

The palladium catalyst of (Step 3) can be a ligand coordinated palladium (0) catalyst. For example, the palladium catalyst of (Step 3) can be a tetrakis (trialkylphosphine) palladium (0) or a tetrakis(triarylphosphine) palladium (0) catalyst. For example, the palladium catalyst of (Step 3) can be tetrakis (triphenylphosphine) palladium (0). In one embodiment, in (Step 3) the ratio of the equivalents of coordinated palladium (0) catalyst (e.g., tetrakis(triphenylphosphine) palladium (0)) to the equivalents of compound (VI) or compound (VI-a) is about 1:20.

The solvent of (Step 3) can include an aqueous solvent. For example, the solvent of (Step 3) can include a mixture of water and an organic solvent, wherein the organic solvent is selected from methanol, ethanol, propanol, isopropanol, butanol, isobutanol, secondary butanol, tertiary butanol, benzene, toluene, tetrahydrofuran, dimethylformamide, 1,2-diethyl ether, dimethoxyethane, diisopropyl ether, methyltertiarybutyl ether, methoxymethyl ether, 2-methoxyethyl ether, 1,4-dioxane, and 1,3-dioxolane, or mixtures thereof. The solvent of (Step. 3) can include a mixture of water, toluene, and ethanol. For example, the solvent of (Step 3) can include a mixture of water, toluene, and ethanol in a ratio of about 1:3:1 by volume.

(Step 3) can be carried out at a temperature between about 20° C. and about 100° C. For example, (Step 3) is carried out at the reflux temperature of the solvent.

The acid of (Step 3-1) can be, for example, acetic acid, adipic acid, ascorbic acid, citric acid, 2,5-dihydroxybenzoic acid, 2,3,4,5-tetrahydroxyhexane-1,6-dicarboxylic acid, glutamic acid, glycolic acid, benzenesulfonic acid, 1,2-ethanedisulfonic acid, ethanesulfonic acid, acid, glutamic acid, hippuric acid, hydrochloric acid, gluconic acid, maleic acid, malic acid, malonic acid, naphthalene-1-sulfonic acid, naphthalene-2-sulfonic acid, naphthalene-1,2-disulfonic acid, oxalic acid, phosphoric acid, citric acid, sulfuric acid, tartaric acid, p-toluenesulfonic acid, trifluoroacetic acid, or mixtures thereof. For example, the acid of (Step 3-1) can be hydrochloric acid.

The solvent of (Step 3-1) can be methanol, ethanol, propanol, isopropanol, butanol, isobutanol, secondary butanol, tertiary butanol, benzene, toluene, tetrahydrofuran, dimethylformamide, 1,2-diethyl ether, dimethoxyethane, diisopropyl ether, methyltertiarybutyl ether, methoxymethyl ether, 2-methoxyethyl ether, 1,4-dioxane, 1,3-dioxolane, ethyl acetate, dichloromethane, 1,1-dichloroethane, or mixtures thereof. For example, the solvent of (Step 3-1) can be a mixture of ethyl acetate and methanol.

The acid of (Step 4) can be, for example, trifluoroacetic acid.

The acid of (Step 5) can be, for example, acetic acid, adipic acid, ascorbic acid, citric acid, 2,5-dihydroxybenzoic acid, 2,3,4,5-tetrahydroxyhexane-1,6-dicarboxylic acid, glutamic acid, glycolic acid, benzenesulfonic acid, 1,2-ethanedisulfonic acid, ethanesulfonic acid, gluconic acid, glutamic acid, hippuric acid, hydrochloric acid, gluconic acid, maleic acid, malic acid, malonic acid, naphthalene-1-sulfonic acid, naphthalene-2-sulfonic acid, naphthalene-1,2-disulfonic acid, oxalic acid, phosphoric acid, citric acid, sulfuric acid, tartaric acid, p-toluenesulfonic acid, trifluoroacetic acid, or mixtures thereof. For example, the acid of (Step 5) can be hydrochloric acid.

The protecting group reagent of (Step 2-1) is selected such that the N-Protecting Group of Compound (VI-a-P) is selected from a) N-benzyl, b) N-t-butyldimethylsilyl, c) N-t-butdyldiphenylsilyl, d) N-t-butyloxycarbonyl, e) N-p-methoxybenzyl, f) N-methoxymethyl, g) N-tosyl, h) N-trifluoroacetyl, i) N-trimethylsilyl, j) N-fluorenylmethyloxycarbonyl, k) N-2-trimethylsilyl-ethyoxycarbonyl, l) N-1-methyl-1-(4-biphenylyl)ethoxycarbonyl, m) N-allyloxycarbonyl, and n) N-benzyloxycarbonyl. For example, the protecting group reagent of (Step 2-1) can be di-tert-butyl carbonate.

In some embodiments of the invention, Compound (VII) is selected from:

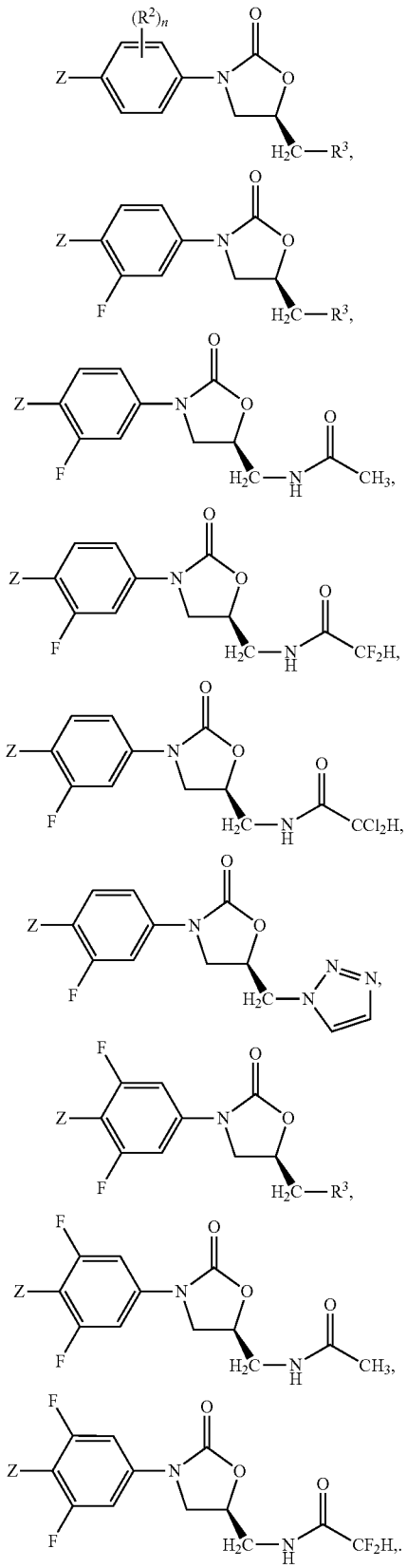

-continued
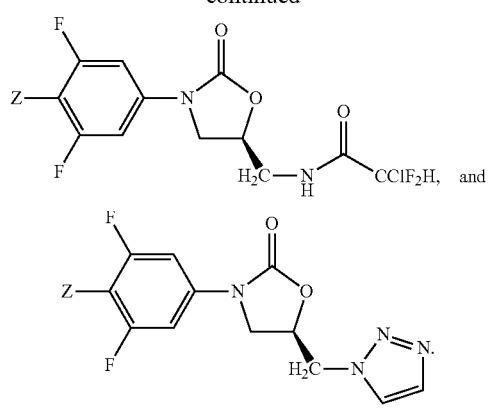
In some embodiments of the invention, Compound (VII-a) is selected from:
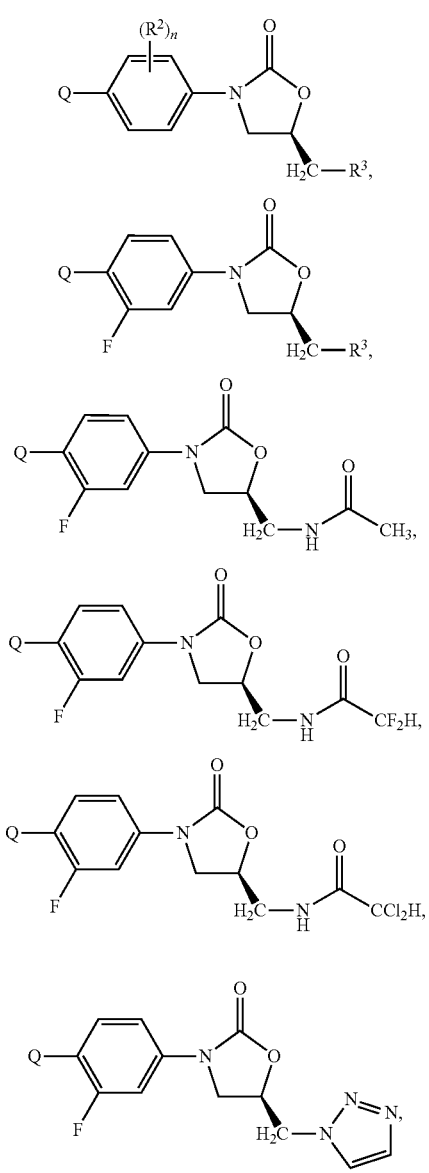
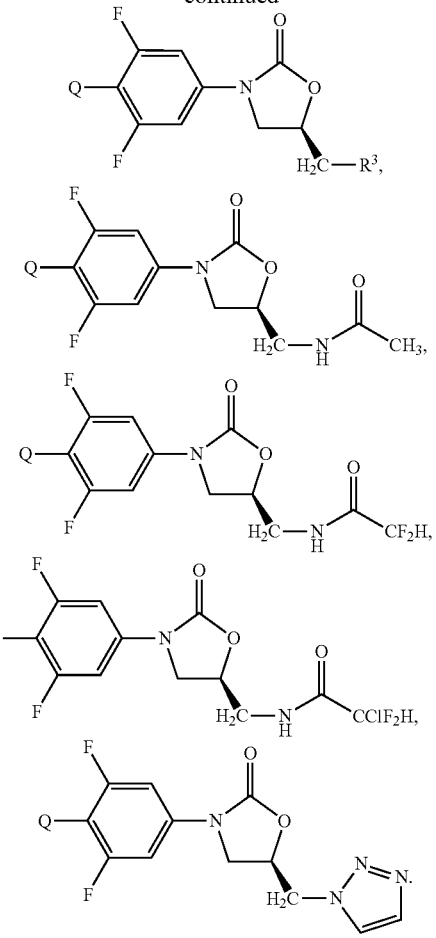
In some embodiments, Compound (V) has the formula:
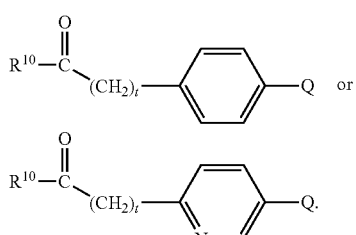
In some embodiments, Compound (V-a) has the formula:
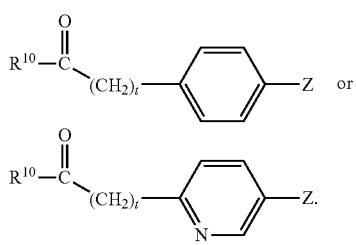
In yet further embodiments, the present invention also relates to and is intended to include the intermediate compounds useful in the processes of the present invention.

The invention relates to a compound corresponding to the structure

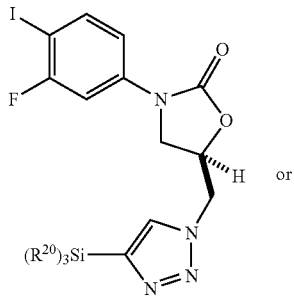

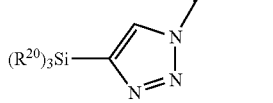

or

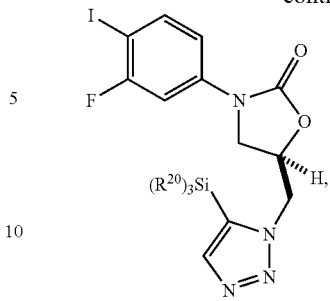

or a pharmaceutically acceptable salt thereof, wherein each $R^{20}$ is independently $C_1$-$C_6$ alkyl or —O—($C_1$-$C_6$ alkyl).

In one embodiment, $R^{20}$ is methyl.

Table 1 includes exemplary compounds that can be synthesized according to the processes of the invention.

TABLE 1

| Compound Number | Structure |
|---|---|
| 1 | N-[3-(2-Fluoro-4'-{[(3H-[1,2,3]triazol-4-ylmethyl)-amino]-methyl}-biphenyl-4-yl)-2-oxo-oxazolidin-5-(S)-ylmethyl]-acetamide |
| 2 | 3-(2-Fluoro-4'-{[(3H-[1,2,3]triazol-4-ylmethyl)-amino]-methyl}-biphenyl-4-yl)-5-(R)-[1,2,3]triazol-1-ylmethyl-oxazolidin-2-one |
| 3 | N-[3-(2-Fluoro-4'-{[(3H-[1,2,3]triazol-4-ylmethyl)-amino]-methyl}-biphenyl-4-yl)-2-oxo-oxazolidin-5-(S)-ylmethyl]-difluoroacetamide |

TABLE 1-continued

| Compound Number | Structure |
|---|---|
| 4 | N-[3-(2-Fluoro-4'-{[(3H-[1,2,3]triazol-4-ylmethyl)-amino]-methyl}-biphenyl-4-yl)-2-oxo-oxazolidin-5-(S)-ylmethyl]-dichloroacetamide |
| 5 | N-[3-(2-Fluoro-4'-{[3-(3H-[1,2,3]triazol-4-yl)-propylamino]-methyl}-biphenyl-4-yl)-2-oxo-oxazolidin-5-(S)-ylmethyl]-acetamide |
| 6 | N-[3-(2-Fluoro-4'-{[2-(3H-[1,2,3]triazol-4-yl)-ethylamino]-methyl}-biphenyl-4-yl)-2-oxo-oxazolidin-5-(S)-ylmethyl]-acetamide |
| 7 | N-[3-(2-Fluoro-4'-{[methyl-(3H-[1,2,3]triazol-4-ylmethyl)-amino]-methyl}-biphenyl-4-yl)-2-oxo-oxazolidin-5-(S)-ylmethyl]-acetamide |
| 8 | N-[3-(2-Fluoro-4'-{[1-(R/S)-(3H-[1,2,3]triazol-4-yl)-ethylamino]-methyl}-biphenyl-4-yl)-2-oxo-oxazolidin-5-(S)-ylmethyl]-acetamide |

TABLE 1-continued

| Compound Number | Structure |
|---|---|
| 9 | N-[3-(2-Fluoro-4'-{2[(3H-[1,2,3]triazol-4-ylmethyl)-amino]-ethyl}-biphenyl-4-yl)-2-oxo-oxazolidin-5-ylmethyl]-acetamide |
| 10 | N-[3-(2-Fluoro-4'-{2-[2-(3H-[1,2,3]triazol-4-ylmethyl)-ethylamino]-ethyl}-biphenyl-4-yl)-2-oxo-oxazolidin-5-ylmethyl]-acetamide |
| 11 | N-[3-(2,6-Difluoro-4'-{[(3H-[1,2,3]triazol-4-ylmethyl)-amino]-methyl}-biphenyl-4-yl)-2-oxo-oxazolidin-5-(S)-ylmethyl]-acetamide |
| 12 | 3-(2,6-Difluoro-4'-{[(3H-[1,2,3]triazol-4-ylmethyl)-amino]-methyl}-biphenyl-4-yl)-5-(R)-[1,2,3]triazol-1-ylmethyl-oxazolidin-2-one |
| 13 | N-[3-(2,6-Difluoro-4'-{[(3H-[1,2,3]triazol-4-ylmethyl)-amino]-methyl}-biphenyl-4-yl)-2-oxo-oxazolidin-5-(S)-ylmethyl]-difluoroacetamide |

TABLE 1-continued

| Compound Number | Structure |
|---|---|
| 14 | N-[3-(2,6-Difluoro-4'-{[(3H-[1,2,3]triazol-4-ylmethyl)-amino]-methyl}-biphenyl-4-yl)-2-oxo-oxazolidin-5-(S)-ylmethyl]-dichloroacetamide |
| 15 | N-[3-(2,6-Difluoro-4'-{[3-(3H-[1,2,3]triazol-4-yl)-propylamino]-methyl}-biphenyl-4-yl)-2-oxo-oxazolidin-5-(S)-ylmethyl]-acetamide |
| 16 | N-[3-(2,6-Difluoro-4'-{[2-(3H-[1,2,3]triazol-4-yl)-ethylamino]-methyl}-biphenyl-4-yl)-2-oxo-oxazolidin-5-(S)-ylmethyl]-acetamide |
| 17 | N-[3-(2,6-Difluoro-4'-{[methyl-(3H-[1,2,3]triazol-4-ylmethyl)-amino]-methyl}-biphenyl-4-yl)-2-oxo-oxazolidin-5-(S)-ylmethyl]-acetamide |
| 18 | N-[3-(2,6-Difluoro-4'-{[1-(R/S)-(3H-[1,2,3]triazol-4-yl)-ethylamino]-methyl}-biphenyl-4-yl)-2-oxo-oxazolidin-5-(S)-ylmethyl]-acetamide |

TABLE 1-continued

| Compound Number | Structure |
|---|---|
| 19 | N-[3-(2,6-Difluoro-4'-{2-[(3H-[1,2,3]triazol-4-ylmethyl)-amino]-ethyl}-biphenyl-4-yl)-2-oxo-oxazolidin-5-(S)-ylmethyl]-acetamide |
| 20 | N-[3-(2,6-Diluoro-4'-{2-[2-(3H-[1,2,3]triazol-4-yl)-ethylamino]-ethyl}-biphenyl-4-yl)-2-oxo-oxazolidin-5-(S)-ylmethyl]-acetamide |
| 21 | N-{3-[3-Fluoro-4-(6-{[(3H-[1,2,3]triazol-4-ylmethyl)-amino]-methyl}-pyridin-3-yl)-phenyl]-2-oxo-oxazolidin-5-(S)-ylmethyl}-acetamide |
| 22 | 3-[3-Fluoro-4-(6-{[(3H-[1,2,3]triazol-4-ylmethyl)-amino]-methyl}-pyridin-3-yl)-phenyl]-5-(R)-[1,2,3]triazol-1-ylmethyl-oxazolidin-2-one |
| 23 | 2,2-Difluoro-N-{3-{3-fluoro-4-(6-{[3H-[1,2,3]triazol-4-yl)-propylamino]-methyl}-pyridin-3-yl)-phenyl]-2-oxo-oxazolidin-5-(S)-methyl}-acetamide |

TABLE 1-continued

| Compound Number | Structure |
|---|---|
| 24 | 2,2-Dichloro-N-{3-{3-fluoro-4-(6-{[3H-[1,2,3]triazol-4-yl)-amino]-methyl}-pyridin-3-yl)-phenyl]-2-oxo-oxazolidin-5-(S)-methyl}-acetamide |
| 25 | N-{3-[3-Fluro-4-(6-{[3-(3H-[1,2,3]triazol-4-yl)-propylamino]-methyl}-pyridin-3-yl)-phenyl]-2-oxo-oxazolidin-5-(S)-methyl}-acetamide |
| 26 | N-{4-[3-Fluro-4-(6-{[2-(3H-[1,2,3]triazol-4-yl)-ethylamino]-methyl}-pyridin-3-yl)-phenyl]-5-oxo-tetrahydro-furan-2-(S)-ylmethyl}-acetamide |
| 27 | N-{3-[3-Fluro-4-(6-{[3-(3H-[1,2,3]triazol-4-ylmethyl)-amino]-methyl}-pyridin-3-yl)-pheny]-2-oxo-oxazolidin-5-(S)-methyl}-acetamide |
| 28 | N-{3-[3-Fluro-4-(6-{[1-(3H-[1,2,3]triazol-4-yl)-ethylamino]-(R/S)-methyl}-pyridin-3-yl)-phenyl]-2-oxo-oxazolidin-5-(S)-ylmethyl}-acetamide |

TABLE 1-continued

| Compound Number | Structure |
|---|---|
| 29 | N-{3-[3-Fluro-4-(6-{2-(3H-[1,2,3]triazol-4-ylmethyl)-amino]-ethyl}-pyridin-3-yl)-phenyl]-2-oxo-oxazolidin-5-(S)-ylmethyl}-acetamide |
| 30 | N-{3-[3-Fluro-4-(6-{2-[2-(3H-[1,2,3]triazol-4-yl)-ethylamino]-ethyl}-pyridin-3-yl)-phenyl]-2-oxo-oxazolidin-5-(S)-ylmethyl}-acetamide |

In the foregoing table, a bolded bond is shown to indicate a particular stereochemistry at a chiral center. An unbolded bond from a chiral center indicates that the substituent can be either an enantiomer, i.e., R or S, or a mixture of both. Furthermore, the chemical names are provided below each compound for convenience and are not intended to limit the indicated chemical structures. To the extent that there is a discrepancy between the chemical name and the structure of a compound, the structure of the compound shall govern. Also, depending on the conventions and choices available, more than one chemical name can be given to a particular chemical structure. As a nonlimiting example, Compound 8 is drawn with stereochemistry indicated for the methyl acetamide substituent on the oxazolidinone ring, but with no stereochemistry indicated for the methyl substituent on the chiral center of the methylene group connecting the triazole ring and the N of the remainder of the molecule. Compound 8 is named indicating the "5S" stereochemistry at the chiral carbon center at which the acetamide substituent is attached. However, Compound 8 is also named with a "(R/S)" designation, indicating that the stereochemistry is undefined or the compound is racemic with respect to the methyl substituent, where no stereochemistry is indicated.

Table 2 illustrates the various chemical components, i.e. the aminoalkyne compound, oxazolidinone compound, and aldehyde compound used in the synthesis of the compounds of Table 1.

TABLE 2

| Compound No. | Aminoalkyne Compound | Oxazolidinone Compound | Aldehyde Compound |
|---|---|---|---|
| 1 | H—≡—CH$_2$NH$_2$<br>1002 | 1010 | 1005 |

TABLE 2-continued

| Compound No. | Aminoalkyne Compound | Oxazolidinone Compound | Aldehyde Compound |
|---|---|---|---|
| 2 | H—≡—CH$_2$NH$_2$ <br> 1002 | 1025 | HCO—⟨⟩—B(OH)$_2$ <br> 1005 |
| 2 | H—≡—CH$_2$NH$_2$ <br> 1002 | 1024i <br> and <br> 1024ii | HCO—⟨⟩—B(OH)$_2$ <br> 1005 |
| 3 | H—≡—CH$_2$NH$_2$ <br> 1002 | 1026 | HCO—⟨⟩—B(OH)$_2$ <br> 1005 |

TABLE 2-continued

| Compound No. | Aminoalkyne Compound | Oxazolidinone Compound | Aldehyde Compound |
|---|---|---|---|
| 4 | H—≡—CH$_2$NH$_2$ 1002 | 1027 (3-fluoro-4-iodophenyl oxazolidinone with CH$_2$NHC(O)CHCl$_2$ substituent) | HCO—C$_6$H$_4$—B(OH)$_2$ 1005 |
| 5 | H—≡—(CH$_2$)$_3$NH$_2$ 1028 | 1010 (3-fluoro-4-iodophenyl oxazolidinone with CH$_2$NHAc substituent) | HCO—C$_6$H$_4$—B(OH)$_2$ 1005 |
| 6 | H—≡—(CH$_2$)$_2$NH$_2$ 1029 | 1010 | HCO—C$_6$H$_4$—B(OH)$_2$ 1005 |
| 7 | H—≡—CH$_2$NHCH$_3$ 1030 | 1010 | HCO—C$_6$H$_4$—B(OH)$_2$ 1005 |
| 8 | H—≡—CHCH$_3$NH$_2$ 1031 | 1010 | HCO—C$_6$H$_4$—B(OH)$_2$ 1005 |

TABLE 2-continued
| Compound No. | Aminoalkyne Compound | Oxazolidinone Compound | Aldehyde Compound |
|---|---|---|---|
| 9 | H—≡—CH$_2$NH$_2$ <br> 1002 | 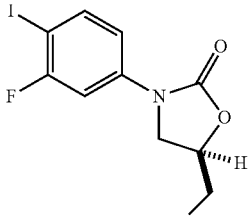 <br> 1010 | 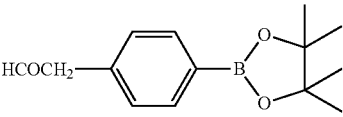 <br> 1032 |
| 10 | H—≡—(CH$_2$)$_2$NH$_2$ <br> 1029 | 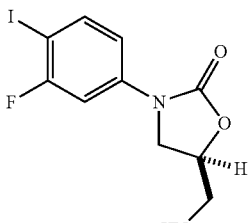 <br> 1010 | 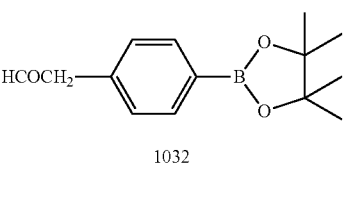 <br> 1032 |
| 11 | H—≡—CH$_2$NH$_2$ <br> 1002 | 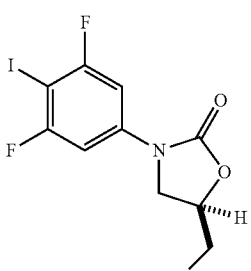 <br> 1033 |  <br> 1005 |
| 12 | H—≡—CH$_2$NH$_2$ <br> 1002 | 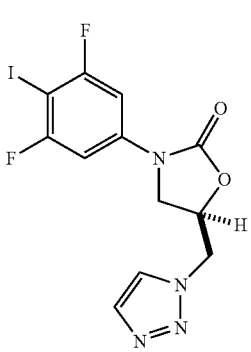 <br> 1034 | 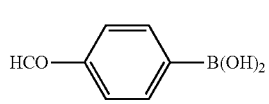 <br> 1005 |

TABLE 2-continued

| Compound No. | Aminoalkyne Compound | Oxazolidinone Compound | Aldehyde Compound |
|---|---|---|---|
| 13 | H≡≡—CH₂NH₂  1002 | 1035 | HCO—C₆H₄—B(OH)₂  1005 |
| 14 | H≡≡—CH₂NH₂  1002 | 1036 | HCO—C₆H₄—B(OH)₂  1005 |
| 15 | H≡≡—(CH₂)₃NH₂  1028 | 1033 | HCO—C₆H₄—B(OH)₂  1005 |
| 16 | H≡≡—(CH₂)₂NH₂  1029 | 1033 | HCO—C₆H₄—B(OH)₂  1005 |

TABLE 2-continued

| Compound No. | Aminoalkyne Compound | Oxazolidinone Compound | Aldehyde Compound |
|---|---|---|---|
| 17 | H—≡—CH₂NHCH₃<br>1030 | 1033 | HCO—C₆H₄—B(OH)₂<br>1005 |
| 18 | H—≡—CHCH₃NH₂<br>1031 | 1033 | HCO—C₆H₄—B(OH)₂<br>1005 |
| 19 | H—≡—CH₂NH₂<br>1002 | 1033 | HCOCH₂—C₆H₄—Bpin<br>1032 |
| 20 | H—≡—(CH₂)₂NH₂<br>1029 | 1033 | HCOCH₂—C₆H₄—Bpin<br>1032 |

TABLE 2-continued

| Compound No. | Aminoalkyne Compound | Oxazolidinone Compound | Aldehyde Compound |
|---|---|---|---|
| 21 | H—≡—CH$_2$NH$_2$  1002 | 1037 | 1038 |
| 22 | H—≡—CH$_2$NH$_2$  1002 | 1039 | 1038 |
| 23 | H—≡—CH$_2$NH$_2$  1002 | 1040 | 1038 |
| 24 | H—≡—CH$_2$NH$_2$  1002 | 1041 | 1038 |

TABLE 2-continued

| Compound No. | Aminoalkyne Compound | Oxazolidinone Compound | Aldehyde Compound |
|---|---|---|---|
| 25 | H—≡—(CH₂)₃NH₂  1028 | 1037 | 5-bromo-2-formylpyridine  1038 |
| 26 | H—≡—(CH₂)₂NH₂  1029 | 1037 | 5-bromo-2-formylpyridine  1038 |
| 27 | H—≡—CH₂NHCH₃  1030 | 1037 | 5-bromo-2-formylpyridine  1038 |
| 28 | H—≡—CHCH₃NH₂  1031 | 1037 | 5-bromo-2-formylpyridine  1038 |

TABLE 2-continued

| Compound No. | Aminoalkyne Compound | Oxazolidinone Compound | Aldehyde Compound |
|---|---|---|---|
| 29 | H—≡—CH$_2$NH$_2$ 1002 | 1037 | HCOCH$_2$—[pyridine]—Br 1042 |
| 30 | H—≡—(CH$_2$)$_2$NH$_2$ 1029 | 1037 | HCOCH$_2$—[pyridine]—Br 1042 |

3. EXAMPLES

Embodiments of the present invention are described in the following examples, which are meant to illustrate, not to limit, the scope and nature of the invention.

Nuclear magnetic resonance (NMR) spectra were obtained on a Bruker Avance 300 or Avance 500 spectrometer, or in some cases a GE-Nicolet 300 spectrometer. Common reaction solvents were either high performance liquid chromatography (HPLC) grade or American Chemical Society (ACS) grade, and anhydrous as obtained from the manufacturer unless otherwise noted. "Chromatography" or "purified by silica gel" refers to flash column chromatography using silica gel (EM Merck, Silica Gel 60, 230-400 mesh) unless otherwise noted.

Some of the abbreviations used in the following experimental details of the synthesis of the examples are defined below:
hr=hour(s)
min=minute(s)
mol=mole(s)
mmol=millimole(s)
M=molar
μM=micromolar
g=gram(s)
μg=microgram(s)
rt=room temperature
L=liter(s)
mL=milliliter(s)
Et$_2$O=diethyl ether
THF=tetrahydrofuran
DMSO=dimethyl sulfoxide
EtOAc=ethyl acetate
Et$_3$N=triethylamine
i-Pr$_2$NEt=diisopropylethylamine
CH$_2$Cl$_2$=methylene chloride
CHCl$_3$=chloroform
CDCl$_3$=deuterated chloroform
CCl$_4$=carbon tetrachloride
MeOH=methanol
CD$_3$OD=deuterated methanol
EtOH=ethanol
DMF=dimethylformamide
BOC=t-butoxycarbonyl
CBZ=benzyloxycarbonyl
LCMS=liquid chromatography mass spectroscopy
TBS=t-butyldimethylsilyl
TBSCl=t-butyldimethylsilyl chloride
TFA=trifluoroacetic acid
TMS=trimethylsilyl (when a substituent in a chemical structure) or tetramethylsilane
DBU=diazabicycloundecene
TBDPSCl=t-butyldiphenylchlorosilane
Hunig's Base=NN-diisopropylethylamine
DMAP=4-dimethylaminopyridine
CuI=copper (I) iodide
MsCl=methanesulfonyl chloride
NaN$_3$=sodium azide
Na$_2$SO$_4$=sodium sulfate
NaHCO$_3$=sodium bicarbonate
NaOH=sodium hydroxide
MgSO$_4$=magnesium sulfate
K$_2$CO$_3$=potassium carbonate
KOH=potassium hydroxide
NH$_4$OH=ammonium hydroxide
NH$_4$Cl=ammonium chloride
SiO$_2$=silica
Pd—C=palladium on carbon
Pd(dppf)Cl$_2$=dichloro[1,1'-bis(diphenylphosphino)ferrocene]palladium (II)

Example 1
Synthesis of Compound 1
Compound 1 and its hydrochloride salt are synthesized according to the following Scheme:
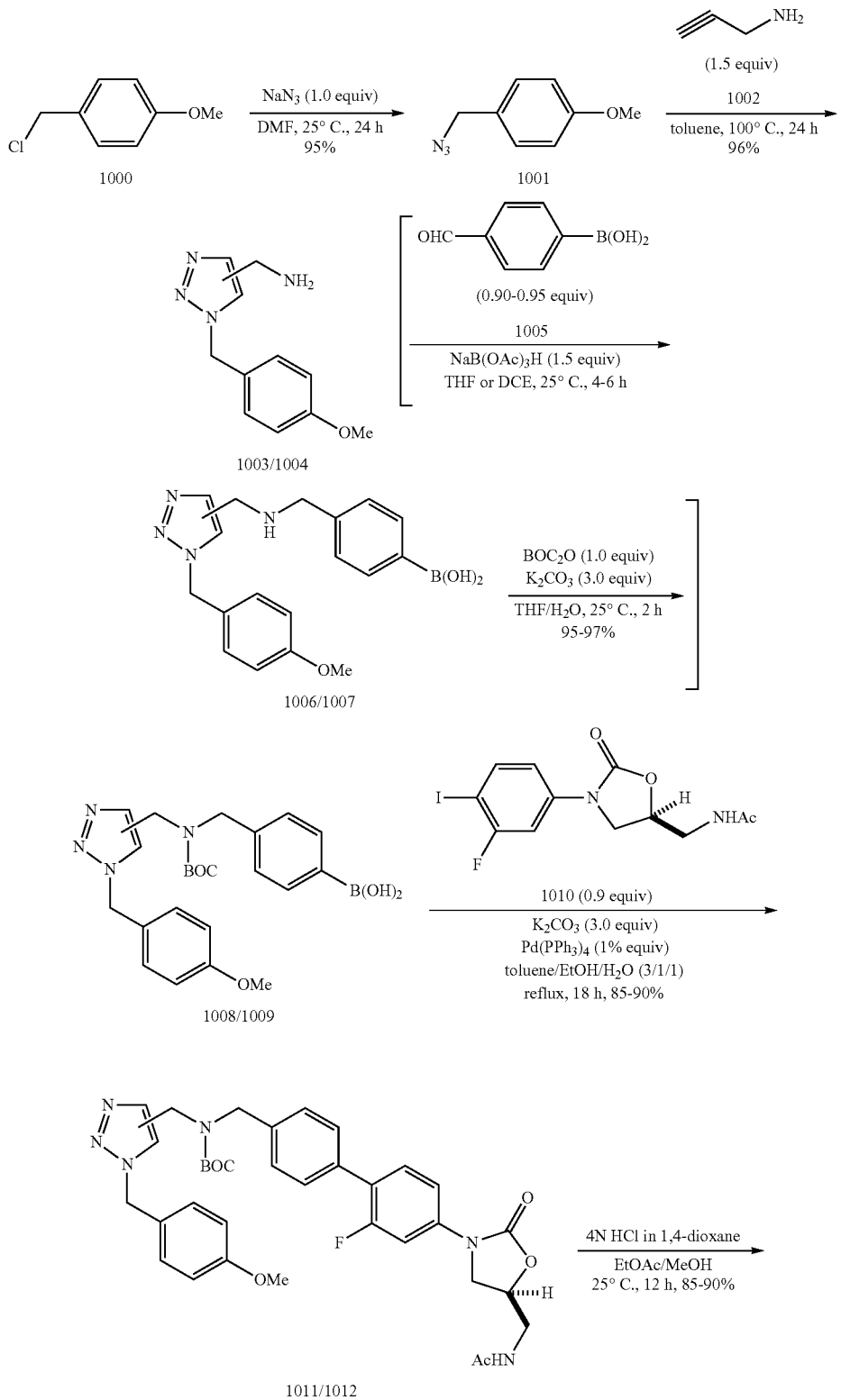

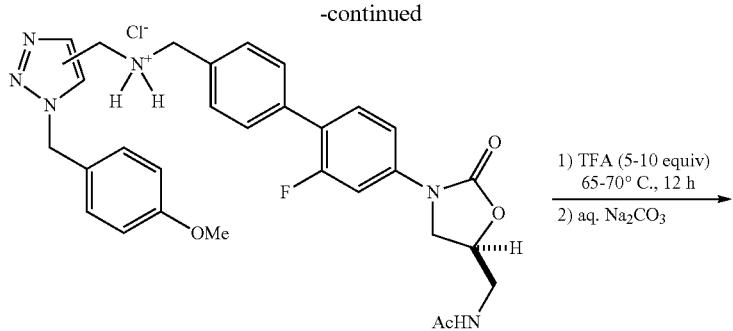

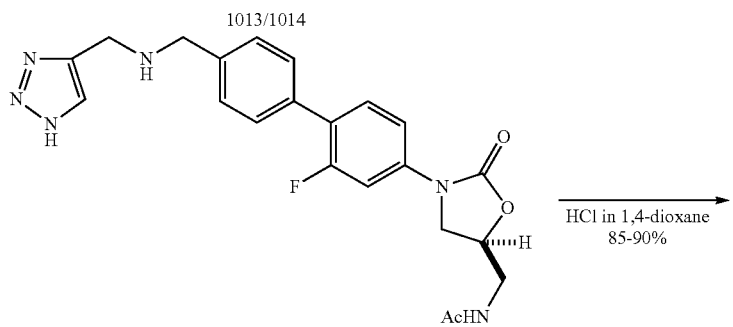

Compound 1

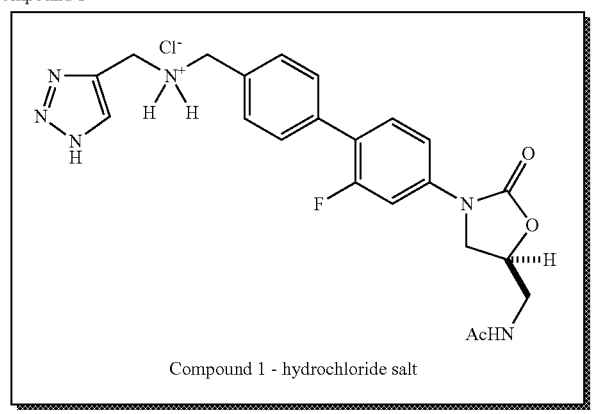

Compound 1 - hydrochloride salt

4-Methoxybenzyl Azide 1001

A solution of 4-methoxybenzyl chloride 1000 (51.8 g, 331.0 mmol) in anhydrous DMF (200 mL) was treated with solid sodium azide (21.5 g, 331.0 mmol, 1.0 equiv) at 25° C., and the resulting mixture was stirred at 25° C. for 24 h. When TLC and HPLC/MS showed that the reaction was complete, the reaction mixture was quenched with $H_2O$ (400 mL) and ethyl acetate (EtOAc, 400 mL) at room temperature. The two layers were separated, and the aqueous layer was extracted with EtOAc (200 mL). The combined organic extracts were washed with $H_2Od$ (2×200 mL) and saturated NaCl aqueous solution (100 mL), dried over $MgSO_4$, and concentrated in vacuo. The crude 4-methoxybenzyl azide (51.2 g, 53.95 g theoretical, 94.9% yield) was obtained as colorless oil, which by HPLC and $^1H$ NMR was found to be essentially pure and was directly used in the subsequent reaction without further purifications. For 4-methoxybenzyl azide 1001: $^1H$ NMR (300 MHz, $CDCl_3$) δ 3.84 (s, 3H, $ArOCH_3$), 4.29 (s, 2H, Ar—$CH_2$), 6.96 (d, 2H, J=8.7 Hz), 7.28 (d, 2H, J=7.8 Hz).

C-[1-(4-Methoxy-benzyl)-1H-[1,2,3]triazol-4-yl]-methylamine and C-[3-(4-Methoxy-benzyl)-3H-[1,2,3]triazol-4-yl]-methylamine (1003 and 1004)

A solution of 4-methoxybenzyl azide 1001 (61.2 g, 375.5 mmol) in toluene (188 mL) was treated with propargylamine 1002 (commercially available, 30.97 g, 38.6 mL, 563.0 mmol, 1.5 equiv) at 25° C., and the resulting reaction mixture was warmed up to gentle reflux at 100-110° C. for 21 h. When TLC and HPLC/MS showed that the reaction was complete, the reaction mixture was cooled down to room temperature before being concentrated in vacuo to remove the excess amount of propargylamine and solvent. The oily residue was then treated with 30% ethyl acetate-hexane (v/v, 260 mL), and the resulting mixture was warmed up to reflux and stirred at reflux for 30 min before being cooled down to room temperature for 1 h. The pale-yellow solids were then collected by filtration, washed with 30% ethyl acetate-hexane (v/v, 2×100 mL), and dried in vacuo at 40° C. for overnight to afford the crude, cycloaddition product (78.8 g, 81.75 g theoretical, 96.4%) as a mixture of two regioisomers, C-[1-(4-methoxy-benzyl)-1H-[1,2,3]triazol-4-yl]-methylamine and C-[3-(4-methoxy-benzyl)-3H-[1,2,3]triazol-4-yl]-methylamine (1003 and 1004), in a ratio of 1.2 to 1 by $^1$H NMR. The crude cycloaddition product was found to be essentially pure and the two regioisomers were not separated before being used directly in the subsequent reaction without further purification. For 1003 and 1004: $^1$H NMR (300 MHz, DMSO-d$_6$) δ 1.82 (br. s, 2H, NH$_2$), 3.72 and 3.73 (two s, 3H, Ar—OCH$_3$), 5.47 and 5.53 (two s, 2H, ArCH$_2$), 6.89 and 6.94 (two d, 2H, J=8.7 Hz, Ar—H), 7.17 and 7.29 (two d, 2H, J=8.7 Hz, Ar—H), 7.58 and 7.87 (two br. s, 1H, triazole-CH); C$_{11}$H$_{14}$N$_4$O, LCMS (EI) m/e 219 (M$^+$+H) and 241 (M$^+$+Na).

4-({tert-Butoxycarbonyl-[1-(4-methoxy-benzyl)-1H-[1,2,3]triazol-4-ylmethyl]-amino}-methyl)-phenylboronic acid and 4-({tert-Butoxycarbonyl-[3-(4-methoxy-benzyl)-3H-[1,2,3]triazol-4-ylmethyl]-amino}-methyl)-phenylboronic acid (1008 and 1009)

Method A. A solution of the regioisomeric C-[1-(4-methoxy-benzyl)-1H-[1,2,3]triazol-4-yl]-methylamine and C-[3-(4-methoxy-benzyl)-3H-[1,2,3]triazol-4-yl]-methylamine (1003 and 1004, 20.0 g, 91.74 mmol) in 1,2-dichloroethane (DCE, 280 mL) was treated with 4-formylphenylboronic acid 1005 (commercially available, 12.39 g, 82.57 mmol, 0.9 equiv) at room temperature, and the resulting reaction mixture was stirred at room temperature for 10 min. Sodium triacetoxyborohydride (NaB(OAc)$_3$H, 29.2 g, 137.6 mmol, 1.5 equiv) was then added to the reaction mixture in three portions over the period of 1.5 h at room temperature, and the resulting reaction mixture was stirred at room temperature for an additional 3.5 h. When TLC and HPLC/MS showed that the reductive amination reaction was complete, the reaction mixture was concentrated in vacuo. The residue, which contained a regioisomeric mixture of 4-({[1-(4-methoxy-benzyl)-1H-[1,2,3]triazol-4-ylmethyl]-amino}-methyl)-phenylboronic acid and 4-({[3-(4-methoxy-benzyl)-3H-[1,2,3]triazol-4-ylmethyl]-amino}-methyl)-phenylboronic acid as the reductive amination products (1006 and 1007), was then treated with tetrahydrofuran (THF, 100 mL) and water (H$_2$O, 100 mL). The resulting solution was subsequently treated with solid potassium carbonate (K$_2$CO$_3$, 37.98 g, 275.2 mmol, 3.0 equiv) and di-ter-butyl dicarbonate (BOC$_2$O, 20.02 g, 91.74 mmol, 1.0 equiv) at room temperature and the reaction mixture was stirred at room temperature for 2 h. When TLC and HPLC/MS showed that the N-BOC protection reaction was complete, the reaction mixture was treated with ethyl acetate (EtOAc, 150 mL) and water (H$_2$O, 100 mL). The two layers were separated, and the aqueous layer was extracted with ethyl acetate (50 mL). The combined organic extracts were washed with H$_2$O (50 mL), 1.5 N aqueous HCl solution (2×100 mL), H$_2$O (100 mL), and saturated aqueous NaCl solution (100 mL), dried over MgSO$_4$, and concentrated in vacuo. The crude, regioisomeric 4-({tert-butoxycarbonyl-[1-(4-methoxy-benzyl)-1H-[1,2,3]triazol-4-ylmethyl]-amino}-methyl)-phenylboronic acid and 4-({tert-butoxycarbonyl-[3-(4-methoxy-benzyl)-3H-[1,2,3]triazol-4-ylmethyl]-amino}-methyl)-phenylboronic acid (1008 and 1009, 35.98 g, 37.32 g, 96.4%) was obtained as a pale-yellow oil, which solidified upon standing at room temperature in vacuo. This crude material was directly used in the subsequent reaction without further purification. For 1008 and 1009: $^1$H NMR (300 MHz, DMSO-d$_6$) δ 1.32 and 1.37 (two br. s, 9H, COOC(CH$_3$)$_3$), 3.70, 3.73 and 3.74 (three s, 3H, Ar—OCH$_3$), 4.07-4.39 (m, 4H), 5.49 and 5.52 (two s, 2H), 6.70-8.04 (m, 9H, Ar—H and triazole-CH); C$_{23}$H$_{29}$BN$_4$O$_5$, LCMS (EI) m/e 453 (M$^+$+H) and 475 (M$^+$+Na).

Method B. A solution of the regioisomeric C-[1-(4-methoxy-benzyl)-1H-[1,2,3]triazol-4-yl]-methylamine and C-[3-(4-methoxy-benzyl)-3H-[1,2,3]triazol-4-yl]-methylamine (1003 and 1004, 20.06 g, 92.0 mmol) in tetrahydrofuran (THF, 300 mL) was treated with 4-formylphenylboronic acid (13.11 g, 87.4 mmol, 0.95 equiv) at room temperature, and the resulting reaction mixture was stirred at room temperature for 10 min. Sodium triacetoxyborohydride (NaB(OAc)$_3$H, 29.25 g, 138.0 mmol, 1.5 equiv) was then added to the reaction mixture in three portions over the period of 1.5 h at room temperature, and the resulting reaction mixture was stirred at room temperature for an additional 3.5 h. When TLC and HPLC/MS showed that the reductive amination reaction was complete, the reaction mixture, which contained a regioisomeric mixture of 4-({[1-(4-methoxy-benzyl)-1H-[1,2,3]triazol-4-ylmethyl]-amino}-methyl)-phenylboronic acid and 4-({[3-(4-methoxy-benzyl)-3H-[1,2,3]triazol-4-ylmethyl]-amino}-methyl)-phenylboronic acid as the reductive amination products (1006 and 1007), was then treated with water (H$_2$O, 200 mL). The resulting aqueous solution was subsequently treated with solid potassium carbonate (K$_2$CO$_3$, 38.0 g, 276 mmol, 3.0 equiv) and di-tert-butyl dicarbonate (BOC$_2$O, 20.08 g, 92 mmol, 1.0 equiv) at room temperature and the reaction mixture was stirred at room temperature for 2 h. When TLC and HPLC/MS showed that the N-BOC protection reaction was complete, the reaction mixture was treated with ethyl acetate (EtOAc, 150 mL) and water (H$_2$O, 100 mL). The two layers were separated, and the aqueous layer was extracted with ethyl acetate (50 mL). The combined organic extracts were washed with H$_2$O (50 mL), 1.5 N aqueous HCl solution (2×100 mL), H$_2$O (100 mL), and saturated aqueous NaCl solution (100 mL), dried over MgSO$_4$, and concentrated in vacuo. The crude, 4-({tert-butoxycarbonyl-[1-(4-methoxy-benzyl)-1H-[1,2,3]triazol-4-ylmethyl]-amino}-methyl)-phenylboronic acid and 4-({tert-butoxycarbonyl-[3-(4-methoxy-benzyl)-3H-[1,2,3]triazol-4-ylmethyl]-amino}-methyl)-phenylboronic acid (1008 and 1009, 38.45 g, 39.50 g, 97.3%) was obtained as a pale-yellow oil, which solidified upon standing at room temperature in vacuo. This crude material was found to be essentially identical in every comparable aspect as the material obtained from Method A and was directly used in the subsequent reaction without further purification.

(5S)-{4'-[5-(Acetylamino-methyl)-2-oxo-oxazolidin-3-yl]-2'-fluoro-biphenyl-4-ylmethyl}-[1-(4-methoxy-benzyl)-1H-[1,2,3]triazol-4-ylmethyl]-carbamic acid tert-butyl ester and (5S)-{4'-[5-(Acetylamino-methyl)-2-oxo-oxazolidin-3-yl]-2'-fluoro-biphenyl-4-ylmethyl}-[1-(4-methoxy-benzyl)-1-[1,2,3]triazol-5-ylmethyl]-carbamic acid tert-butyl ester (1011 and 1012)

A suspension of the crude regioisomeric mixture of 4-({tert-butoxycarbonyl-[1-(4-methoxy-benzyl)-1H-[1,2,3]triazol-4-ylmethyl]-amino}-methyl)-phenylboronic acid and 4-({tert-butoxycarbonyl-[3-(4-methoxy-benzyl)-3H-[1,2,3]triazol-4-ylmethyl]amino}-methyl)-phenylboronic acid (1008 and 1009, 37.62 g, 83.23 mmol) and N-[3-(3-fluoro-4-iodo-phenyl)-2-oxo-oxazolidin-5-ylmethyl]-acetamide (1010, 28.32 g, 74.9 mmol, 0.90 equiv) in toluene (150 mL) was treated with powder K$_2$CO$_3$ (34.45 g, 249.7 mol, 3.0 equiv), EtOH (50 mL), and H$_2$O (50 mL) at 25° C., and the resulting mixture was degassed three times under a steady stream of Argon at 25° C. Pd(PPh$_3$)$_4$ (866 mg, 0.749 mmol, 0.01 equiv) was subsequently added to the reaction mixture, and the resulting reaction mixture was degassed three times again under a stead stream of Argon at 25° C. before being warmed up to gentle reflux for 18 h. When TLC and HPLC/MS showed the coupling reaction was complete, the reaction mixture was cooled down to room temperature before being treated with H$_2$O (100 mL) and ethyl acetate (100 mL). The two layers were then separated, and the aqueous layer was extracted with EtOAc (100 mL). The combined organic extracts were washed with H$_2$O (50 mL), 1.5 N aqueous HCl solution (2×150 mL), H$_2$O (100 mL), and the saturated aqueous NaCl solution (100 mL), dried over MgSO$_4$, and concentrated in vacuo. The residual oil was solidified upon standing at room temperature in vacuo to afford the crude, (5S)-{4'-[5-(acetylamino-methyl)-2-oxo-oxazolidin-3-yl]-2'-fluoro-biphenyl-4-ylmethyl}-[1-(4-methoxy-benzyl)-1H-[1,2,3]triazol-4-ylmethyl]-carbamic acid tert-butyl ester (1011) and (5S)-{4'-[5-(acetylamino-methyl)-2-oxo-oxazolidin-3-yl]-2'-fluoro-biphenyl-4-ylmethyl}-[1-(4-methoxy-benzyl)-1H-[1,2,3]triazol-5-ylmethyl]-carbamic acid tert-butyl ester (1012) as a regioisomeric mixture. This crude product (43.36 g, 49.28 g theoretical, 88%) was used directly in the subsequent reaction without further purification. For the mixture of 1011 and 1012: $^1$H NMR (300 MHz, DMSO-d$_6$) δ 1.35 and 1.38 (two br. s, 9H, COO(CH$_3$)$_3$), 1.85 (s, 3H, COCH$_3$), 3.45 (t, 2H, J=5.4 Hz), 3.73 and 3.76 (two s, 3H, Ar—OCH$_3$), 3.79 (dd, 1H, J=6.6, 9.1 Hz), 4.18 (t, 1H, J=9.1 Hz), 4.35-4.43 (m, 41.1), 4.73-4.81 (m, 1H), 5.50 (br, s, 2H), 6.90 and 6.98 (two d, 2H, J=8.7 Hz), 7.28 and 7.32 (two d, 2H, J=8.7 Hz), 7.35 (dd, 2H, J=2.2, 8.6 Hz), 7.42 (dd, 1H, J=2.2, 8.6 Hz), 7.49-7.63 (m, 4H, aromatic-H), 7.90 and 7.99 (two br. s, 1H, triazole-CH), 8.29 (t, 1H, J=5.8 Hz, NHCOCH$_3$); C$_{35}$H$_{39}$FN$_6$O$_6$, LCMS (EI) m/e 659 (M$^+$+H) and 681 (M$^+$+Na).

(5S)—N-{3-[2-Fluoro-4'-({[1-(4-methoxy-benzyl)-1H-[1,2,3]triazol-4-ylmethyl]-amino}-methyl)-biphenyl-4-yl]-2-oxo-oxazolidin-5-ylmethyl}-acetamide Hydrochloride (1013) and (5S)—N-{3-[2-Fluoro-4'-({[1-(4-methoxy-benzyl)-1H-[1,2,3]triazol-5-ylmethyl]-amino}-methyl)-biphenyl-4-yl]-2-oxo-oxazolidin-5-ylmethyl}-acetamide Hydrochloride (1014)

A solution of a regioisomeric mixture of (5S)-{4'-[5-(acetylamino-methyl)-2-oxo-oxazolidin-3-yl]-2'-fluoro-biphenyl-4-ylmethyl}-[1-(4-methoxy-benzyl)-1H-[1,2,3]triazol-4-ylmethyl}-carbamic acid tert-butyl ester and (5S)-{4'-[5-(acetylamino-methyl)-2-oxo-oxazolidin-3-yl]-2'-fluoro-biphenyl-4-ylmethyl}-[1-(4-methoxy-benzyl)-1H-[1,2,3]triazol-5-ylmethyl]-carbamic acid tert-butyl ester (1011 and 1012, 37.28 g, 56.65 mmol) in ethyl acetate (EtOAc, 150 mL) and methanol (MeOH, 30 mL) was treated with a solution of 4 N hydrogen chloride in 1,4-dioxane (113.3 mL, 453.2 mmol, 8.0 equiv) at room temperature, and the resulting reaction mixture was stirred at room temperature for 12 h. When TLC and HPLC/MS showed that the N-BOC deprotection reaction was complete, the solvents were removed in vacuo. The residue was then suspended in 250 mL of 5% methanol (MeOH) in acetonitrile (CH$_3$CN), and the resulting slurry was stirred at room temperature for 1 h. The solids were then collected by filtration, washed with toluene (2×100 mL) and 5% methanol in acetonitrile (2×50 mL), and dried in vacuo to afford a regioisomeric mixture of the crude, (5S)—N-{3-[2-fluoro-4'-({[1-(4-methoxy-benzyl)-1H-[1,2,3]triazol-4-ylmethyl]-amino}-methyl)-biphenyl-4-yl]-2-oxo-oxazolidin-5-ylmethyl}-acetamide hydrochloride and (5S)—N-{3-[2-fluoro-4'-({[1-(4-methoxy-benzyl)-1H-[1,2,3]triazol-5-ylmethyl]-amino}-methyl)-biphenyl-4-yl]-2-oxo-oxazolidin-5-ylmethyl}-acetamide hydrochloride (1013 and 1014, 30.0 g, 33.68 g theoretical, 89.1% yield) as off-white crystals in a ratio of 1.2 to 1. This material was found by $^1$H NMR and HPLC/MS to be essentially pure and was directly used in the subsequent reactions without further purification. For the regioisomeric mixture of 1013 and 1014: $^1$H NMR (300 MHz, DMSO-d$_6$) δ 1.84 (s, 3H, COCH$_3$), 3.44 (t, 2H, J=5.4 Hz), 3.71 and 3.74 (two s, 3H, Ar—OCH$_3$), 3.80 (dd, 1H, J=6.6, 9.1 Hz), 4.17 (t, 1H, J=9.1 Hz), 4.23-4.30 (m, 4H), 4.73-4.80 (m, 1H), 5.58 and 5.70 (two s, 2H), 6.88 and 6.93 (two d, 2H, J=8.7 Hz), 7.15 and 7.32 (two d, 2H, J=8.7 Hz), 7.43 (dd, 2H, J=2.2, 8.6 Hz), 7.52-7.62 (m, 6H, aromatic-H), 8.28 (s, 1H, triazole-CH), 8.32 (t, 1H, J=5.8 Hz, NHCOCH$_3$), 9.91 and 10.32 (two br. s, 2H, ArCH$_2$N$^+$H$_2$); C$_{30}$H$_{31}$FN$_6$O$_4$, LCMS (EI) m/e 559 (M$^+$+H) and 581 (M$^+$+Na).

(5S)—N-[3-(2-Fluoro-4'-{[(1H-[1,2,3]triazol-4-ylmethyl)-amino]-methyl}-biphenyl-4-yl)-2-oxo-oxazolidin-5-ylmethyl]-acetamide hydrochloride (1 hydrochloride salt)

A solution of the crude regioisomeric mixture of (5S)—N-{3-[2-fluoro-4'-({[1-(4-methoxy-benzyl)-1H-[1,2,3]triazol-4-ylmethyl]-amino}-methyl)-biphenyl-4-yl]-2-oxo-oxazolidin-5-ylmethyl}-acetamide hydrochloride and (5S)—N-{3-[2-fluoro-4-({[1-(4-methoxy-benzyl)-1H-[1,2,3]triazol-5-ylmethyl]-amino}-methyl)-biphenyl-4-yl]-2-oxo-oxazolidin-5-ylmethyl}-acetamide hydrochloride (1013 and 1014, 29.17 g, 49.07 mmol) in trifluoroacetic acid (TFA, 150 mL) was warmed up to 65-70° C., and the resulting reaction mixture was stirred at 65-70° C. for 12 h. When TLC and HPLC/MS showed that the deprotection reaction was complete, the solvents were removed in vacuo. The residual solids were then treated with ethyl acetate (EtOAc, 100 mL) and H$_2$O (150 mL) before being treated with a saturated aqueous solution of sodium carbonate (30 mL) at room temperature. The resulting mixture was then stirred at room temperature for 1 h before the solids were collected by filtration, washed with EtOAc (2×50 mL) and H$_2$O (2×50 mL), and dried in vacuo at 40-45° C. to afford the crude, (5S)—N-[3-(2-fluoro-4'-{[(1H-[1,2,3]triazol-4-ylmethyl)-amino]-methyl}-biphenyl-4-yl)-2-oxo-oxazolidin-5-ylmethyl]-acetamide (1 as the free base, 18.9 g, 21.49 g theoretical, 87.9%) as off-white powders, which by HPLC/MS and $^1$H NMR was found to be one pure regioisomer and this regioisomer was found to be identical as the material obtained from deprotection of 1013 alone by the same method. For 1 as the free base: $^1$H NMR (300 MHz, DMSO-d$_6$) δ 1.85 (s, 3H, COCH$_3$), 3.44 (t, 2H, J=5.4 Hz), 3.74 (s, 2H), 3.77 (s, 2H), 3.79 (dd, 1H, J=6.4, 9.2 Hz), 4.17 (t, 1H, J=9.1 Hz), 4.72-4.81 (m, 1H), 7.39-7.62 (m, 7H, aromatic-H), 7.73 (s, 1H, triazole-CH), 8.29 (t, 1H, J=5.8 Hz, NHCOCH$_3$), 9.72 (br. s, 2H, ArCH$_2$N$^+$H$_2$), 15.20 (br. s, 1H, triazole-NH); C$_{22}$H$_{23}$FN$_6$O$_3$, LCMS (EI); m/e 439 (M$^+$+H) and 461 (M$^+$+Na).

A suspension of 1 free base (18.0 g, 41.1 mmol) in ethyl acetate (EtOAc, 80 mL), and methanol (MeOH, 20 mL) was treated with a solution of 4.0 N hydrogen chloride in 1,4-dioxane (41.1 mL, 164.4 mmol, 4.0 equiv) at room temperature, and the resulting mixture was stirred at room temperature for 8 h. The solvents were then removed in vacuo, and the residue was further dried in vacuo before being treated with a mixture of 10% methanol in acetonitrile (80 mL). The solids were collected by filtration, washed with 10% MeOH/acetonitrile (2×40 mL), and dried in vacuo to afford 1 hydrochloride salt (18.13 g, 19.50 g theoretical, 93% yield) as off-white crystals.

The crude 1 hydrochloride salt can be recrystallized from acetonitrile and water, if necessary, according to the following procedure: A suspension of the crude 1 hydrochloride salt (50.0 g) in acetonitrile (1250 mL) was warmed up to reflux before the distilled water (H$_2$O, 280 mL) was gradually introduced to the mixture. The resulting clear yellow to light brown solution was then stirred at reflux for 10 min before being cooled down to 45-55° C. The solution was then filtered through a Celite bed at 45-55° C., and the filtrates were gradually cooled down to room temperature before being further cooled down to 0-5° C. in an ice bath for 1 h. The solids were then collected by filtration, washed with acetonitrile (2×50 mL), and dried in vacuo at 40° C. for 24 h to afford the recrystallized 1 hydrochloride salt (42.5 g, 50.0 g theoretical, 85% recovery) as off-white crystals. For 1: $^1$H NMR (300 MHz, DMSO-d$_6$) δ 1.86 (s, 3H, COCH$_3$), 3.45 (t, 2H, J=5.4 Hz), 3.84 (dd, 1H, J=6.4, 9.2 Hz), 4.19 (t, 1H, J=9.1 Hz), 4.24 (br, s, 2H), 4.31 (br. s, 2H), 4.74-4.79 (m, 1H), 7.44 (dd, 1H, J=2.2, 8.6 Hz), 7.57-7.66 (m, 6H, aromatic-H), 8.17 (s, 1H, triazole-CH), 8.30 (t, 1H, J=5.8 Hz, NHCOCH$_3$), 9.72 (br. s, 2H, ArCH$_2$N$^+$H$_2$), 15.20 (br. s, 1H, triazole-NH); $^{13}$C NMR (75 MHz, DMSO-d$_6$) δ 22.57, 40.69, 41.50, 47.36, 49.23, 71.85, 105.70 (d, J=28.5 Hz), 114.14 (d, J=2.9 Hz), 122.29 (d, J=13.3 Hz), 128.82 (d, J=3.0 Hz), 130.70, 130.94, 131.0, 131.22, 135.30, 137.92 (br. s), 139.66 (d, J=11.2 Hz), 154.11, 159.13 (d, J=243.5 Hz), 170.19; C$_{22}$H$_{23}$FN$_6$O$_3$—HCl, LCMS (EI) m/e 439 (M$^+$+H) and 461 (M$^+$+Na).

Synthesis of Oxazolidinone Compound 1010

Oxazolidinone compound 1010 is prepared according to the following synthetic scheme.

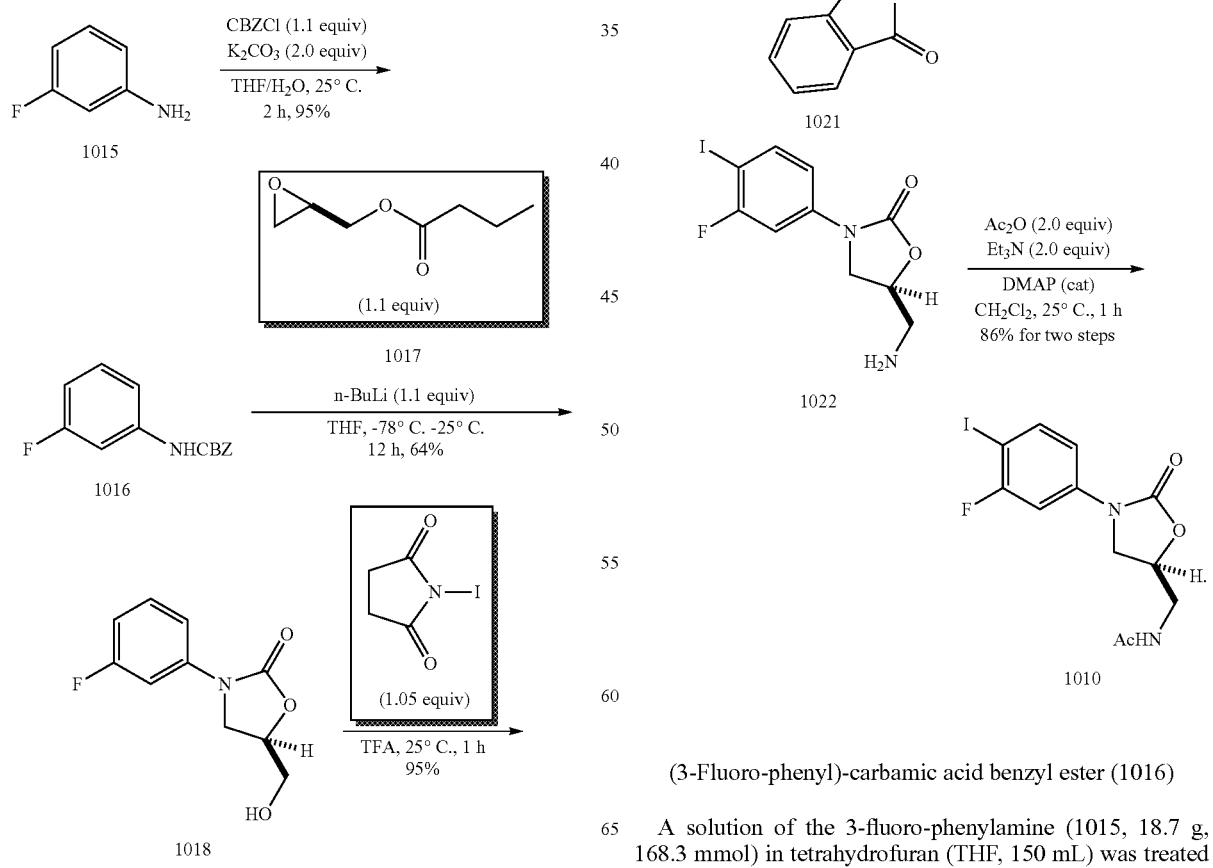

(3-Fluoro-phenyl)-carbamic acid benzyl ester (1016)

A solution of the 3-fluoro-phenylamine (1015, 18.7 g, 168.3 mmol) in tetrahydrofuran (THF, 150 mL) was treated with potassium carbonate (K$_2$CO$_3$, 46.45 g, 336.6 mmol, 2.0 equiv) and H₂O (150 mL) before a solution of benzyl chloroformate (CBZCl, 31.58 g, 185.1 mmol, 26.1 mL, 1.1 equiv) in THF (50 mL) was dropwise added into the reaction mixture at room temperature under $N_2$. The resulting reaction mixture was stirred at room temperature for 2 h. When TLC showed that the reaction was complete, the reaction mixture was treated with H₂O (100 mL) and ethyl acetate (EtOAc, 100 mL). The two layers were separated, and the aqueous layer was extracted with EtOAc (2×100 mL). The combined organic extracts were washed with H₂O (2×100 mL) and saturated NaCl aqueous solution (100 mL), dried over MgSO₄, and concentrated in vacuo. The residue was further dried in vacuo to afford the crude, (3-fluoro-phenyl)-carbamic acid benzyl ester (2, 39.2 g, 41.23 g theoretical, 95%) as pale-yellow oil, which was found to be essentially pure and was directly used in the subsequent reactions without further purifications. For 1016: ¹H NMR (300 MHz, CDCl₃) δ 5.23 (s, 2H, OCH₂Ph), 6.75-6.82 (m, 2H), 7.05 (dd, 1H, J=1.4, 8.2 Hz), 7.22-7.45 (m, 6H); $C_{14}H_{12}FNO_2$, LCMS (EI) m/e 246 (M⁺+H).

(5R)-3-(3-Fluoro-phenyl)-5-hydroxymethyl-oxazolidin-2-one (1018)

A solution of (3-fluoro-phenyl)-carbamic acid benzyl ester (1016, 39.2 g, 160.0 mmol) in anhydrous tetrahydrofuran (THF, 300 mL) was cooled down to −78° C. in a dry-ice-acetone bath before a solution of n-butyl lithium (n-BuLi, 2.5 M solution in hexane, 70.4 mL, 176 mmol, 1.1 equiv) in hexane was dropwise added at −78° C. under $N_2$. The resulting reaction mixture was subsequently stirred at −78° C. for 1 h before a solution of (R)-(−)-glycidyl butyrate 1017 (25.37 g, 24.6 mL, 176 mmol, 1.1 equiv) in anhydrous THF (100 mL) was dropwise added into the reaction mixture at −78° C. under $N_2$. The resulting reaction mixture was stirred at −78° C. for 30 min before being gradually warmed up to room temperature for 12 h under $N_2$. When TLC and HPLC/MS showed that the reaction was complete, the reaction mixture was quenched with H₂O (200 mL), and the resulting mixture was stirred at room temperature for 1 h before ethyl acetate (EtOAc, 200 mL) was added. The two layers were separated, and the aqueous layer was extracted with EtOAc (2×100 mL). The combined organic extracts were washed with H₂O (2×100 mL) and saturated NaCl aqueous solution (100 mL), dried over MgSO₄, and concentrated in vacuo. The white crystals were precipitated out from the concentrated solution when most of the solvents were evaporated. The residue was then treated with 20% EtOAc-hexane (100 mL) and the resulting slurry was further stirred at room temperature for 30 min. The solids were then collected by filtration and washed with 20% EtOAc-hexane (2×50 mL) to afford the crude, (5R)-(3-(3-fluoro-phenyl)-5-hydroxymethyl-oxazolidin-2-one (1018, 24.4 g, 33.76 g theoretical, 72.3%) as white crystals, which were found to be essentially pure and was directly used in the subsequent reactions without further purifications. For 1018: ¹H NMR (300 MHz, DMSO-d₆) δ 3.34-3.72 (m, 2H), 3.83 (dd, 1H, J=6.2, 9.0 Hz), 4.09 (t, 1H, J=12.0 Hz), 4.68-4.75 (m, 1H), 5.23 (t, 1H, J=5.6 Hz, OH), 6.96 (m, 1H), 7.32-7.56 (m, 3H); $C_{10}H_{10}FNO_3$, LCMS (EI) m/e 212 (M⁺+H).

(5R)-3-(3-Fluoro-4-iodo-phenyl)-5-hydroxymethyl-oxazolidin-2-one (1019)

A solution of (5R)-(3-(3-fluoro-phenyl)-5-hydroxymethyl-oxazolidin-2-one (1018, 10.74 g, 50.9 mmol) in trifluoroacetic acid (TFA, 50 mL) was treated with N-iodosuccinimide (NIS, 12.03 g, 53.45 mmol, 1.05 equiv) at 25° C., and the resulting reaction mixture was stirred at 25° C. for 2 h. When TLC and HPLC/MS showed that the reaction was complete, the reaction mixture was concentrated in vacuo. The residue was then treated with H₂O (100 mL) and 20% EtOAc-hexane (100 mL) at 25° C., and the resulting mixture was stirred at 25° C. for 30 min before being cooled down to 0-5° C. for 2 h. The white solids were collected by filtration, washed with H₂O (2×25 mL) and 20% EtOAc-hexane (2×25 mL), and dried in vacuo to afford the crude, (5R)-3-(3-fluoro-4-iodo-phenyl)-5-hydroxymethyl-oxazolidin-2-one (1019, 15.1 g, 17.15 g theoretical, 88%) as off-white powders, which were found to be essentially pure and was directly used in the subsequent reactions without further purifications. For 1019: ¹H NMR (300 MHz, DMSO-d₆) δ 3.58 (dd, 1H, J=4.2, 12.6 Hz), 3.67 (dd, 1H, J=3.0, 12.6 Hz), 3.67 (dd, 1H, J=6.3, 9.0 Hz), 4.07 (t, 1H, J=9.0 Hz), 4.72 (m, 1H), 5.21 (br. s, 1H, OH), 7.22 (dd, 1H, J=2.4, 8.4 Hz), 7.58 (dd, 1H, J=2.4, 11.1 Hz), 7.81 (dd, 1H, J=7.8, 8.7 Hz); $C_{10}H_9FINO_3$, LCMS (EI) m/e 338 (M⁺+H).

(5R)-Methanesulfonic acid 3-(3-fluoro-4-iodo-phenyl)-2-oxo-oxazolidin-5-ylmethyl ester (1020)

A solution of (5R)-3-(3-fluoro-4-iodo-phenyl)-5-hydroxymethyl-oxazolidin-2-one (1019, 25.2 g, 74.8 mmol) in methylene chloride (CH₂Cl₂, 150 mL) was treated with triethylamine (TEA, 15.15 g, 20.9 mL, 150 mmol, 2.0 equiv) at 25° C., and the resulting mixture was cooled down to 0-5° C. before methanesulfonyl chloride (MsCl, 10.28 g, 6.95 mL, 89.7 mmol, 1.2 equiv) was dropwise introduced into the reaction mixture at 0-5° C. under $N_2$. The resulting reaction mixture was subsequently stirred at 0-5° C. for 1 h under $N_2$. When TLC and HPLC/MS showed that the reaction was complete, the reaction mixture was quenched with H₂O (100 mL) and CH₂Cl₂ (100 mL). The two layers were separated, and the aqueous layer was extracted with CH2Cl₂ (100 mL). The combined organic extracts were washed with H₂O (2×100 mL) and saturated NaCl aqueous solution (100 mL), dried over MgSO₄, and concentrated in vacuo. The residue was further dried in vacuo to afford the crude, (5R)-methanesulfonic acid 3-(3-fluoro-4-iodo-phenyl)-2-oxo-oxazolidin-5-ylmethyl ester (1020, 30.71 g, 31.04 g theoretical, 98.9%) as off-white powders, which was found to be essentially pure and was directly used in the subsequent reactions without further purifications. For 1020: $C_{11}H_{11}FINO_5S$, LCMS (EI) m/e 416 (M⁺+H).

(5R)-2-[3-(3-Fluoro-4-iodo-phenyl)-2-oxo-oxazolidin-5-ylmethyl]-isoindole-1,3-dione (1021)

A solution of (5R)-methanesulfonic acid 3-(3-fluoro-4-iodo-phenyl)-2-oxo-oxazolidin-5-ylmethyl ester (1020, 26.38 g, 63.57 mmol) in anhydrous N,N-dimethylformamide (DMF, 120 mL) was treated with solid potassium pathilimide (12.95 g, 70.0 mmol, 1.1 equiv) at 25° C., and the resulting reaction mixture was warmed up to 70° C. for 2 h. When TLC and HPLC showed that the reaction was complete, the reaction mixture was cooled down to room temperature before being quenched with H₂O (400 mL), and the resulting mixture was stirred at room temperature for 10 min before being cooled down to 0-5° C. for 1 h. The white precipitates were then collected by filtration, washed with water (3×100 mL), and dried in vacuo to afford the crude, (5R)-2-[3-(3-fluoro-4-iodo-phenyl)-2-oxo-oxazolidin-5-ylmethyl]-isoindole-1,3-dione (1021, 27.85 g, 29.64 g theoretical, 94%) as off-white powders, which were found to be essentially pure and was directly used in the subsequent reactions without further purifications. For 1021: $C_{18}H_{12}FIN_2O_4$, LCMS (EI) m/e 467 ($M^++H$).

(5S)-5-Aminomethyl-3-(3-fluoro-4-iodo-phenyl)-oxazolidin-2-one (1022)

A solution of (5R)-2-[3-(3-fluoro-4-iodo-phenyl)-2-oxo-oxazolidin-5-ylmethyl]-isoindole-1,3-dione (1021, 23.3 g, 50.0 mmol) in ethanol (EtOH, 150 mL) was treated with hydrazine monohydrate (12.52 g, 12.1 mL, 250 mmol, 5.0 equiv) at 25° C., and the resulting reaction mixture was warmed up to reflux for 2 h. White precipitates were formed while the reaction mixture was refluxed. When TLC and HPLC showed that the reaction was complete, the reaction mixture was cooled down to room temperature before being quenched with $H_2O$ (100 mL). The white precipitates were totally dissolved when water was introduced into the reaction mixture and a homogeneous solution was generated. The aqueous solution was then extracted with $CH_2Cl_2$ (3×200 mL), and the combined organic extracts were washed with $H_2O$ (2×100 mL) and saturated NaCl aqueous solution (100 mL), dried over $MgSO_4$, and concentrated in vacuo. The residue was further dried in vacuo to afford the crude (5S)-5-aminomethyl-3-(3-fluoro-4-iodo-phenyl)-oxazolidin-2-one (1022, 16.0 g, 16.8 g theoretical, 95.2%) as white powders, which were found to be essentially pure and was directly used in the subsequent reactions without further purifications. For 1022: $C_{10}H_{10}FIN_2O_2$, LCMS (EI) m/e 337 ($M^++H$).

(5S)—N-[3-(3-Fluoro-4-iodo-phenyl)-2-oxo-oxazolidin-5-ylmethyl]-acetamide (1010)

A suspension of (5S)-5-aminomethyl-3-(3-fluoro-4-iodo-phenyl)-oxazolidin-2-one (1022, 16.0 g, 47.6 mmol) in $CH_2Cl_2$ (150 mL) was treated with triethylamine (TEA, 9.62 g, 13.2 mL, 95.2 mmol, 2.0 equiv) at 25° C., and the resulting reaction mixture was cooled down to 0-5° C. before being treated with acetic anhydride ($Ac_2O$, 7.29 g, 6.75 mL, 71.4 mmol, 1.5 equiv) and 4-N,N-dimethylaminopyridine (DMAP, 58 mg, 0.5 mmol, 0.01 equiv) at 0-5° C. under $N_2$. The resulting reaction mixture was subsequently stirred at 0-5° C. for 2 h. When TLC and HPLC showed that the reaction was complete, the reaction mixture was quenched with $H_2O$ (100 mL). The two layers were separated, and the aqueous layer was then extracted with $CH_2Cl_2$ (2×50 mL), and the combined organic extracts were washed with $H_2O$ (2×100 mL) and saturated NaCl aqueous solution (100 mL), dried over $MgSO_4$, and concentrated in vacuo. The residue was further dried in vacuo to afford the crude, (5S)—N-[3-(3-fluoro-4-iodo-phenyl)-2-oxo-oxazolidin-5-ylmethyl]-acetamide (1010, 17.36 g, 17.99 g theoretical, 96.5%) as white powders, which were found to be essentially pure and was directly used in the subsequent reactions without further purifications. For 1010: $^1$H NMR (300 MHz, DMSO-$d_6$) δ 1.63 (s, 3H, $NHCOCH_3$), 3.25 (t, 2H, J=5.4 Hz), 3.56 (dd, 1H, J=6.4, 9.2 Hz), 3.95 (t, 1H, J=9.1 Hz), 4.58 (m, 1H), 5.16 (t, 1H, J=5.7 Hz, OH), 7.02 (dd, 1H, J=2.4, 8.2 Hz), 7.38 (dd, 1H, J=2.4, 10.8 Hz), 7.66 (t, 1H, J=7.5, 8.4 Hz), 8.08 (t, 1H, J=5.8 Hz, $NHCOCH_3$); $C_{12}H_{12}FIN_2O_3$, LCMS (EI) m/e 379 ($M^++H$).

Example 2

Synthesis of Compound 2

Compound 2 is prepared using a reaction scheme analogous to that for compound 1, using oxazolidinone compound 1025 in place of iodide 1010.

Synthesis of Oxazolidinone Compound 1025

Oxazolidinone compound 1025 is prepared according to the following reaction scheme which is analogous to that used for the synthesis of oxazolidinone compound 1010.

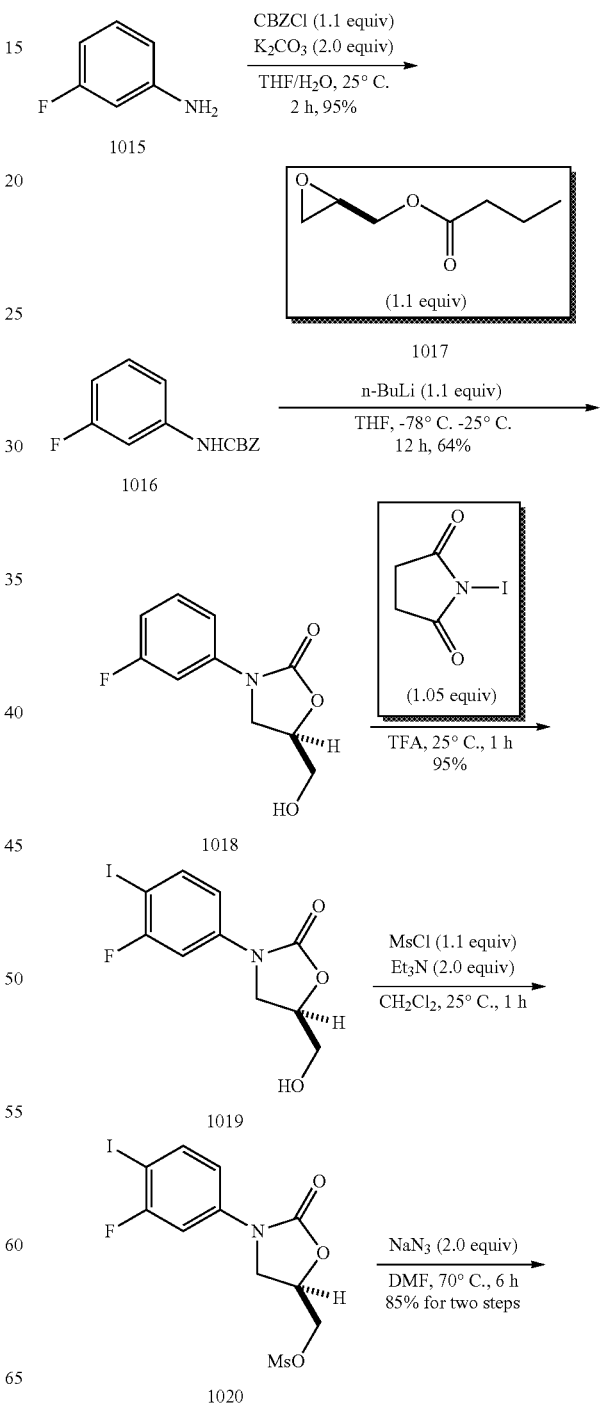

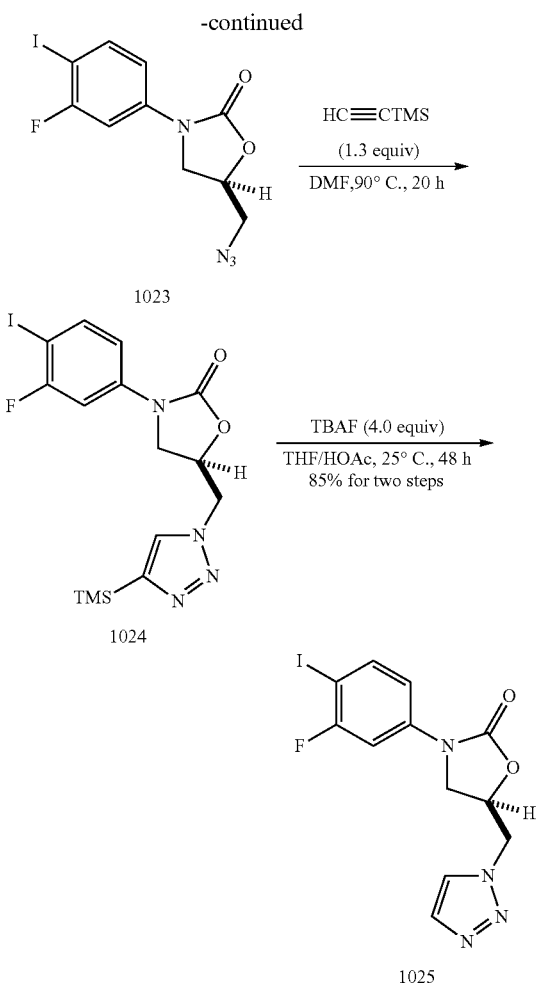

1H), 7.22 (dd, 1H, J=2.4, 8.7 Hz), 7.56 (dd, 1H, J=2.4, 8.7 Hz), 7.84 (dd, 1H, J=7.5, 8.7 Hz); $C_{11}H_{11}FINO_5S$, LCMS (EI) m/e 416 (M$^+$+H).

(5R)-5-Azidomethyl-3-(3-fluoro-4-iodophenyl)-oxazolidin-2-one (1023)

A solution of (5R)-methanesulfonic acid 3-(3-fluoro-4-iodophenyl)-2-oxo-oxazolidin-5-ylmethyl ester (1020, 14.0 g, 33.7 mmol) in anhydrous DMF (50 mL) was treated with sodium azide (NaN$_3$, 4.4 g, 67.5 mmol, 2.0 equiv) at 25° C., and the resulting mixture was subsequently warmed up to 70-75° C. for 4 h. When TLC and HPLC/MS showed that the reaction was complete, the reaction mixture was cooled down to room temperature before being treated with H$_2$O (100 mL) and EtOAc (100 mL). The two layers were then separated, and the aqueous layer was extracted with EtOAc (2×50 mL). The combined organic extracts were then washed with water (2×50 mL) and saturated aqueous NaCl solution (50 mL), dried over MgSO$_4$, and concentrated in vacuo. The residue was further dried in vacuo to afford the crude, (5R)-5-azidomethyl-3-(3-fluoro-4-iodophenyl)-oxazolidin-2-one (1023, 12.08 g, 12.2 g theoretical, 99%) as white powders. For 1023: $^1$H NMR (300 MHz, DMSO-d$_6$) δ 3.67-3.81 (m, 3H), 4.14 (t, 1H, J=5.4 Hz), 4.88-4.94 (m, 1H), 7.22 (dd, 1H, J=2.4, 8.7 Hz), 7.56 (dd, 1H, J=2.4, 8.7 Hz), 7.84 (dd, 1H, J=7.5, 8.7 Hz); LCMS $C_{10}H_5FIN_4O_2$, LCMS (EI) m/e 363 (M$^+$+H).

(5R)-3-(3-Fluoro-4-iodo-phenyl)-5-(4-trimethylsilanyl-[1,2,3]triazol-1-ylmethyl)-oxazolidin-2-one (1024)

A solution of (5R)-5-azidomethyl-3-(3-fluoro-4-iodophenyl)-oxazolidin-2-one (1023, 11.60 g, 32.0 mmol) in anhydrous DMF (50 mL) was treated with trimethylsilylacetylene (4.70 g, 6.77 mL, 48.0 mmol, 1.5 equiv) at room temperature, and the resulting reaction mixture was warmed up to 90-100° C. for 20 h. When TLC and HPLC/MS showed that the cycloaddition reaction was complete, the reaction mixture was cooled down to room temperature before being concentrated in vacuo. The residue was further dried in vacuo to afford the crude, (5R)-3-(3-fluoro-4-iodo-phenyl)-5-(4-trimethylsilanyl-[1,2,3]triazol-1-ylmethyl)-oxazolidin-2-one (1024, 14.72 g, 14.72 g theoretical, 100%) as brown oil, which was directly used in the subsequent reaction without further purification. For 1024: $^1$H NMR (300 MHz, DMSO-d$_6$) δ 0.01. (s, 9H, SiCH$_3$), 3.67 (dd, 1H, J=6.4, 9.2 Hz), 4.01 (t, 1H, J=5.4 Hz), 4.59 (d, 2H, J=4.9 Hz), 4.91-4.94 (m, 1H), 6.88 (dd, 1H, J=2.4, 8.7 Hz), 7.22 (dd, 1H, J=2.4, 8.7 Hz), 7.58 (dd, 1H, J=7.5, 8.7 Hz), 7.73 (s, 1H, triazole-H); $C_{15}H_{18}FIN_4O_2Si$, LCMS (EI); m/e 461 (M$^+$+H).

(5R)-3-(3-Fluoro-4-iodo-phenyl)-5-[1,2,3]triazol-1-ylmethyl-oxazolidin-2-one (1025)

A solution of the crude (5R)-3-(3-fluoro-4-iodo-phenyl)-5-(4-trimethylsilanyl-[1,2,3]triazol-1-ylmethyl)-oxazolidin-2-one (1024, 14.72 g, 32.0 mmol) in an 1 M solution of tetrabutylammonium fluoride in THF (TBAF, 128 mL, 128 mmol, 4.0 equiv) was treated with acetic acid (HOAc, 5 mL) at room temperature, and the resulting reaction mixture was stirred at room temperature for 24 h. When TLC and HPLC/MS showed that the reaction was complete, the solvents were removed in vacuo. The residue was treated with H$_2$O (300 mL) at room temperature and the resulting mixture was stirred at room temperature for 1 h. The solids were collected by filtration, washed with H$_2$O (2×100 mL) and 20% EtOAc/

(5R)-Methanesulfonic acid 3-(3-fluoro-4-iodophenyl)-2-oxo-oxazolidin-5-ylmethyl ester (1020)

A solution of (5R)-3-(3-fluoro-4-iodophenyl)-5-hydroxymethyl-oxazolidin-2-one (1019, 11.66 g, 34.6 mmol) in methylene chloride (CH$_2$Cl$_2$, 80 mL) was treated with N,N-diisopropylethylamine (Hunig's base, DIEA, 8.95 g, 12.1 mL, 69.2 mmol, 2.0 equiv) at 25° C., and the resulting mixture was cooled down to 0-5° C. before methanesulfonyl chloride (MsCl, 4.36 g, 2.95 mL, 38.1 mmol, 1.1 equiv) was dropwise introduced into the reaction mixture at 0-5° C. under N$_2$. The resulting reaction mixture was subsequently stirred at 0-5° C. for 1 h under N$_2$, When TLC and HPLC/MS showed that the reaction was complete, the reaction mixture was quenched with H$_2$O (60 mL) and CH$_2$Cl$_2$ (60 mL). The two layers were separated, and the aqueous layer was extracted with CH$_2$Cl$_2$ (60 mL). The combined organic extracts were washed with H$_2$O (2×60 mL) and saturated NaCl aqueous solution (40 mL), dried over MgSO$_4$, and concentrated in vacuo. The residue was further dried in vacuo to afford the crude, (5R)-methanesulfonic acid 3-(3-fluoro-4-iodophenyl)-2-oxo-oxazolidin-5-ylmethyl ester (1020, 14.0 g, 14.36 g theoretical, 97.5%) as off-white powders, which was found to be essentially pure and was directly used in the subsequent reactions without further purifications. For 1020: $^1$H NMR (300 MHz, DMSO-d$_6$) δ 3.26 (s, 3H, OSO$_2$CH$_3$), 3.83 (dd, 1H, J=6.4, 9.2 Hz), 4.19 (t, 1H, J=5.4 Hz), 4.44-4.54 (m, 2H), 5.01-5.06 (m, hexane (2×100 mL), dried in vacuo. The crude, (5R)-3-(3-fluoro-4-iodo-phenyl)-5-[1,2,3]triazol-1-ylmethyl-oxazolidin-2-one (1025, 11.65 g, 12.416 g theoretical, 93.8%) was obtained as off-white powders, which by HPLC/MS and $^1$H NMR was found to be essentially pure and was directly used in the subsequent reactions without further purification. For 1025: $^1$H NMR (300 MHz, DMSO-d$_6$) 3.89 (dd, 1H, J=6.4, 9.2 Hz), 4.23 (t, 1H, J=5.4 Hz), 4.84 (d, 2H, J=4.9 Hz), 5.12-5.18 (m, 1H), 7.14 (dd, 1H, J=2.4, 8.7 Hz), 7.49 (dd, 1H, J=2.4, 8.7 Hz), 7.76 (d, 1H, J=1.0 Hz, triazole-H), 7.82 (dd, 1H, J=7.5, 8.7 Hz), 8.17 (d, 1H, J=1.0 Hz, triazole-H); $C_{12}H_{10}FIN_4O_2$, LCMS (EI) m/e 389 (M$^+$+H).

Alternate Synthesis for Compound 2

Compound 2 is alternatively prepared using a reaction scheme analogous to that described above, using the TMS-substituted iodide compound 1024 in place of iodide 1025. The TMS group is removed in a later step to yield compound 2. It should be noted that compound 1024 can exist as two isomeric compounds, 1024i and 1024ii, and that the resulting intermediates would correspondingly be produced as isomeric compounds.

The general reaction schemes and syntheses are as follows:

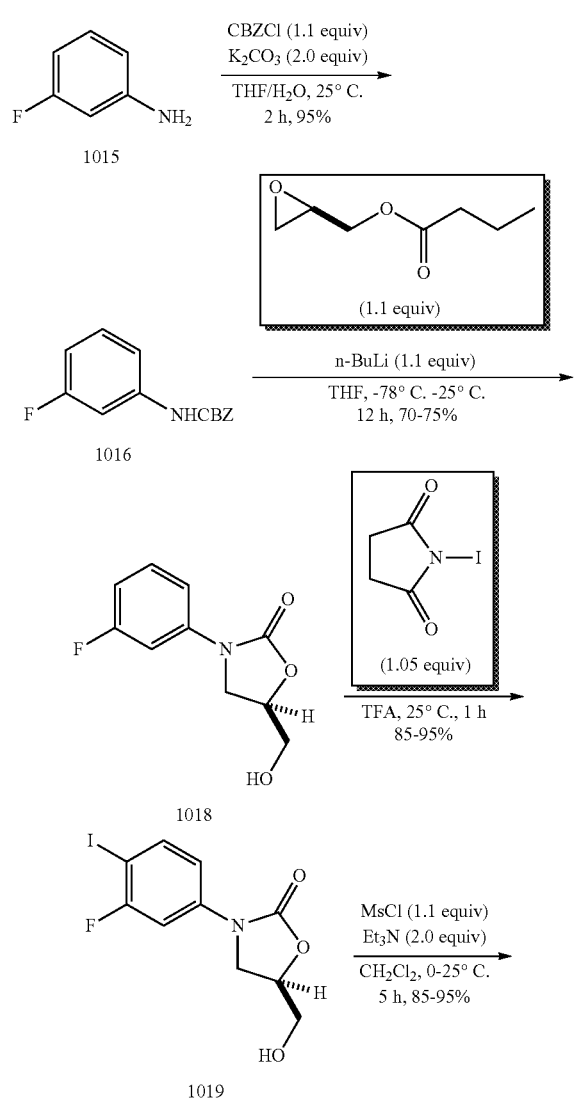

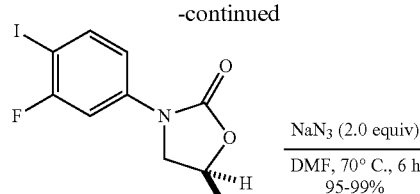

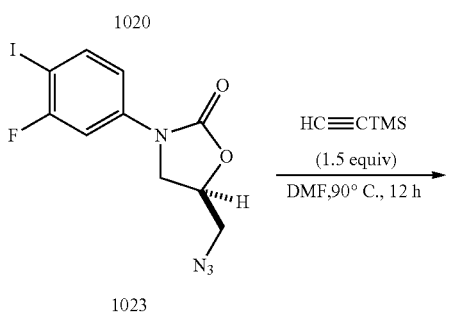

(3-Fluoro-phenyl)-carbamic acid benzyl ester (1016)

A solution of the 3-fluoro-phenylamine (1015, 18.7 g, 168.3 mmol) in tetrahydrofuran (THF, 150 mL) was treated with potassium carbonate (K$_2$CO$_3$, 46.45 g, 336.6 mmol, 2.0 equiv) and H$_2$O (150 mL) before a solution of benzyl chloroformate (CBZCl, 31.58 g, 185.1 mmol, 26.1 mL, 1.1 equiv) in THF (50 mL) was dropwise added into the reaction mixture at room temperature under N$_2$. The resulting reaction mixture was stirred at room temperature for 2 h. When TLC showed that the reaction was complete, the reaction mixture was treated with H$_2$O (100 mL) and ethyl acetate (EtOAc, 100 mL). The two layers were separated, and the aqueous layer was extracted with EtOAc (2×100 mL). The combined organic extracts were washed with H$_2$O (2×100 mL) and saturated NaCl aqueous solution (100 mL), dried over MgSO$_4$, and concentrated in vacuo. The residue was further dried in vacuo to afford the crude, desired (3-fluoro-phenyl)-carbamic acid benzyl ester (1016, 39.2 g, 41.23 g theoretical, 95%) as pale-yellow oil, which was found to be essentially pure and was directly used in the subsequent reactions without further purifications. For 1016: $^1$H NMR (300 MHz, CDCl$_3$) δ 5.23 (s, 2H, OCH$_2$Ph), 6.75-6.82 (m, 2H), 7.05 (dd, 1H, J=1.4, 8.2 Hz), 7.22-7.45 (m, 6H); $C_{14}H_{12}FNO_2$, LCMS (EI) m/e 246 (M$^+$+H).

(5R)-3-(3-Fluoro-phenyl)-5-hydroxymethyl-oxazolidin-2-one (1018)

A solution of (3-fluoro-phenyl)-carbamic acid benzyl ester (1016, 39.2 g, 160.0 mmol) in anhydrous tetrahydrofuran (THF, 300 mL) was cooled down to 78° C. in a dry-ice-acetone bath before a solution of n-butyl lithium (n-BuLi, 2.5 M solution in hexane, 70.4 mL, 176 mmol, 1.1 equiv) in hexane was dropwise added at 78° C. under $N_2$. The resulting reaction mixture was subsequently stirred at 78° C. for 1 h before a solution of (R)-(−)-glycidyl butyrate (25.37 g, 24.6 mL, 176 mmol, 1.1 equiv) in anhydrous THF (100 mL) was dropwise added into the reaction mixture at −78° C. under $N_2$. The resulting reaction mixture was stirred at −78° C. for 30 min before being gradually warmed up to room temperature for 12 h under $N_2$. When TLC and HPLC/MS showed that the reaction was complete, the reaction mixture was quenched with $H_2O$ (200 mL), and the resulting mixture was stirred at room temperature for 1 h before ethyl acetate (EtOAc, 200 mL) was added. The two layers were separated, and the aqueous layer was extracted with EtOAc (2×100 mL). The combined organic extracts were washed with $H_2O$ (2×100 mL) and saturated NaCl aqueous solution (100 mL), dried over $MgSO_4$, and concentrated in vacuo. The white crystals were precipitated out from the concentrated solution when most of the solvents were evaporated. The residue was then treated with 20% EtOAc-hexane (100 mL) and the resulting slurry was further stirred at room temperature for 30 min. The solids were then collected by filtration and washed with 20% EtOAc-hexane (2×50 mL) to afford the crude, desired (5R)-(3-(3-fluoro-phenyl)-5-hydroxymethyl-oxazolidin-2-one (1018, 24.4 g, 33.76 g theoretical, 72.3%) as white crystals, which were found to be essentially pure and was directly used in the subsequent reactions without further purifications. For 1018: $^1H$ NMR (300 MHz, DMSO-$d_6$) δ; $C_{10}H_{10}FNO_3$, LCMS (EI) m/e 212 (M$^+$+H).

(5R)-3-(3-Fluoro-4-iodo-phenyl)-5-hydroxymethyl-oxazolidin-2-one (1019)

A solution of (5R)-3-(3-fluoro-phenyl)-5-hydroxymethyl-oxazolidin-2-one (1018, 10.74 g, 50.9 mmol) in trifluoroacetic acid (TFA, 50 mL) was treated with N-iodosuccinimide (NIS, 12.03 g, 53.45 mmol, 1.05 equiv) at 25° C., and the resulting reaction mixture was stirred at 25° C. for 2 h. When TLC and HPLC/MS showed that the reaction was complete, the reaction mixture was concentrated in vacuo. The residue was then treated with $H_2O$ (100 mL) and 20% EtOAc-hexane (100 mL) at 25° C., and the resulting mixture was stirred at 25° C. for 30 min before being cooled down to 0-5° C. for 2 h. The white solids were collected by filtration, washed with $H_2O$ (2×25 mL) and 20% EtOAc-hexane (2×25 mL), and dried in vacuo to afford the crude, desired (5R)-3-(3-fluoro-4-iodo-phenyl)-5-hydroxymethyl-oxazolidin-2-one (1019, 15.1 g, 17.15 g theoretical, 88%) as off-white powders, which were found to be essentially pure and was directly used in the subsequent reactions without further purifications. For 1019: $^1H$ NMR (300 MHz, DMSO-$d_6$) δ 3.58 (dd, 1H, J=4.2, 12.6 Hz), 3.67 (dd, 1H, J=3.0, 12.6 Hz), 3.67 (dd, 1H, J=6.3, 9.0 Hz), 4.07 (t, 1H, J=9.0 Hz), 4.72 (m, 1H), 5.21 (br. s, 1H, OH), 7.22 (dd, 1H, J=2.4, 8.4 Hz), 7.58 (dd, 1H, J=2.4, 11.1 Hz), 7.81 (dd, 1H, J=7.8, 8.7 Hz); $C_{10}H_9FINO_3$, LCMS (EI) m/e 338 (M$^+$+H).

(5R)-Methanesulfonic acid 3-(3-fluoro-4-iodophenyl)-2-oxo-oxazolidin-5-ylmethyl ester (1020)

A solution of (5R)-3-(3-fluoro-4-iodophenyl)-5-hydroxymethyl-oxazolidin-2-one (1019, 269.6 g, 0.8 mol) in methylene chloride ($CH_2Cl_2$, 1200 mL) was treated with N,N-diisopropylethylamine (Hunig's base, DIEA, 206.8 g, 279 mL, 1.6 mol, 2.0 equiv) at 25° C., and the resulting mixture was cooled down to 0-5° C. before methanesulfonyl chloride (MsCl, 109.97 g, 74.3 mL, 0.96 mol, 1.2 equiv) was dropwise introduced into the reaction mixture at 0-5° C. under $N_2$. The resulting reaction mixture was subsequently stirred at 0-5° C. for 1 h and then gradually warmed up to room temperature for 4 h under $N_2$. When TLC and HPLC/MS showed that the reaction was complete, the reaction mixture was quenched with $H_2O$ (500 mL). The resulting mixture was then stirred at room temperature for 30 min. before being concentrated in vacuo to remove methylene chloride. When almost all of methylene chloride was removed in vacuo, the residue was then treated with $H_2O$ (1000 mL). The resulting slurry was stirred at room temperature for an additional 1 h. The solids were then collected by filtration, washed with $H_2O$ (2×500 mL), and dried in vacuo at 40° C. for 24 h to afford the crude, desired (5R)-methanesulfonic acid 3-(3-fluoro-4-iodophenyl)-2-oxo-oxazolidin-5-ylmethyl ester (1020, 290.0 g, 332.0 g theoretical, 87.3%) as off-white powders, which was found to be essentially pure and was directly used in the subsequent reactions without further purifications. For 1020: $^1H$ NMR (300 MHz, DMSO-ds) δ 3.26 (s, 3H, $OSO_2CH_3$), 3.83 (dd, 1H, J=6.4, 9.2 Hz), 4.19 (t, 1H, J=5.4 Hz), 4.44-4.54 (m, 2H), 5.01-5.06 (m, 1H), 7.22 (dd, 1H, J=2.4, 8.7 Hz), 7.56 (dd, 1H, J=2.4, 8.7 Hz), 7.84 (dd, 1H, J=7.5, 8.7 Hz); $C_{11}H_{11}FINO_5S$, LCMS (EI) m/e 416 (M$^+$+H).

(5R)-5-Azidomethyl-3-(3-fluoro-4-iodophenyl)-oxazolidin-2-one (1023)

A solution of (5R)-methanesulfonic acid 3-(3-fluoro-4-iodophenyl)-2-oxo-oxazolidin-5-ylmethyl ester (5, 290.0 g, 698.8 mmol) in anhydrous DMF (700 mL) was treated with sodium azide ($NaN_3$, 90.84 g, 1.4 mol, 2.0 equiv) at 25° C., and the resulting mixture was subsequently warmed up to 70-75° C. for 6 h. When TLC and HPLC/MS showed that the reaction was complete, the reaction mixture was cooled down to room temperature before being treated with $H_2O$ (1500 mL) and the resulting mixture was stirred at room temperature for 2 h. The solids were then collected by filtration, washed with $H_2O$ (2×500 mL), and dried in vacuo at 40° C. for 24 h to afford the crude, desired (5R)-5-azidomethyl-3-(3-fluoro-4-iodophenyl)-oxazolidin-2-one (1023, 248.0 g, 252.97 g theoretical, 98%) as white powders, which was found to be essentially pure and was directly used in the subsequent reactions without further purifications. For 1023: $^1H$ NMR. (300 MHz, DMSO-$d_6$) δ 3.67-3.81 (m, 31H), 4.14 (t, 1H, J=5.4 Hz), 4.88-4.94 (m, 1H), 7.22 (dd, 1H, J=2.4, 8.7 Hz), 7.56 (dd, 1H, J=2.4, 8.7 Hz), 7.84 (dd, 1H, J=7.5, 8.7 Hz); LCMS $C_{10}H_8FIN_4O_2$, LCMS (EI) m/e 363 (M$^+$+H).

(5R)-3-(3-Fluoro-4-iodo-phenyl)-5-(4-trimethylsilanyl-[1,2,3]triazol-1-ylmethyl)-oxazolidin-2-one (1024)

A solution of (5R)-5-azidomethyl-3-(3-fluoro-4-iodophenyl)-oxazolidin-2-one (1023, 248.0 g, 685.0 mmol) in anhydrous THF (600 mL) was treated with trimethylsilylacetylene (100.9 g, 145.2 mL, 1027.6 mmol, 1.5 equiv) at room temperature, and the resulting reaction mixture was warmed up to reflux for 12 h. When TLC and HPLC/MS showed that the cycloaddition reaction was complete, the reaction mixture was cooled down to room temperature before being concentrated in vacuo. The residue was further dried in vacuo to afford the crude, desired (5R)-3-(3-fluoro-4-iodo-phenyl)-5-(4-trimethylsilanyl-[1,2,3]triazol-1-ylmethyl)-oxazolidin-2-one (1024, 315.1 g, 315.1 g theoretical, 100%) as brown oil, which was directly used in the subsequent reaction without further purification. For 1024: $^1$H NMR (300 MHz, DMSO-$d_6$) δ 0.01 (s, 9H, SiCH$_3$), 3.67 (dd, 1H, J=6.4, 9.2 Hz), 4.01 (t, 1H, J=5.4 Hz), 4.59 (d, 2H, J=4.9 Hz), 4.91-4.94 (m, 1H), 6.88 (dd, 1H, J=2.4, 8.7 Hz), 7.22 (dd, 1H, J=2.4, 8.7 Hz), 7.58 (dd, 1H, J=7.5, 8.7 Hz), 7.73 (s, 1H, triazole-H); $C_{15}H_{18}FIN_4O_2Si$, LCMS (EI) m/e 461 (M$^+$+H).
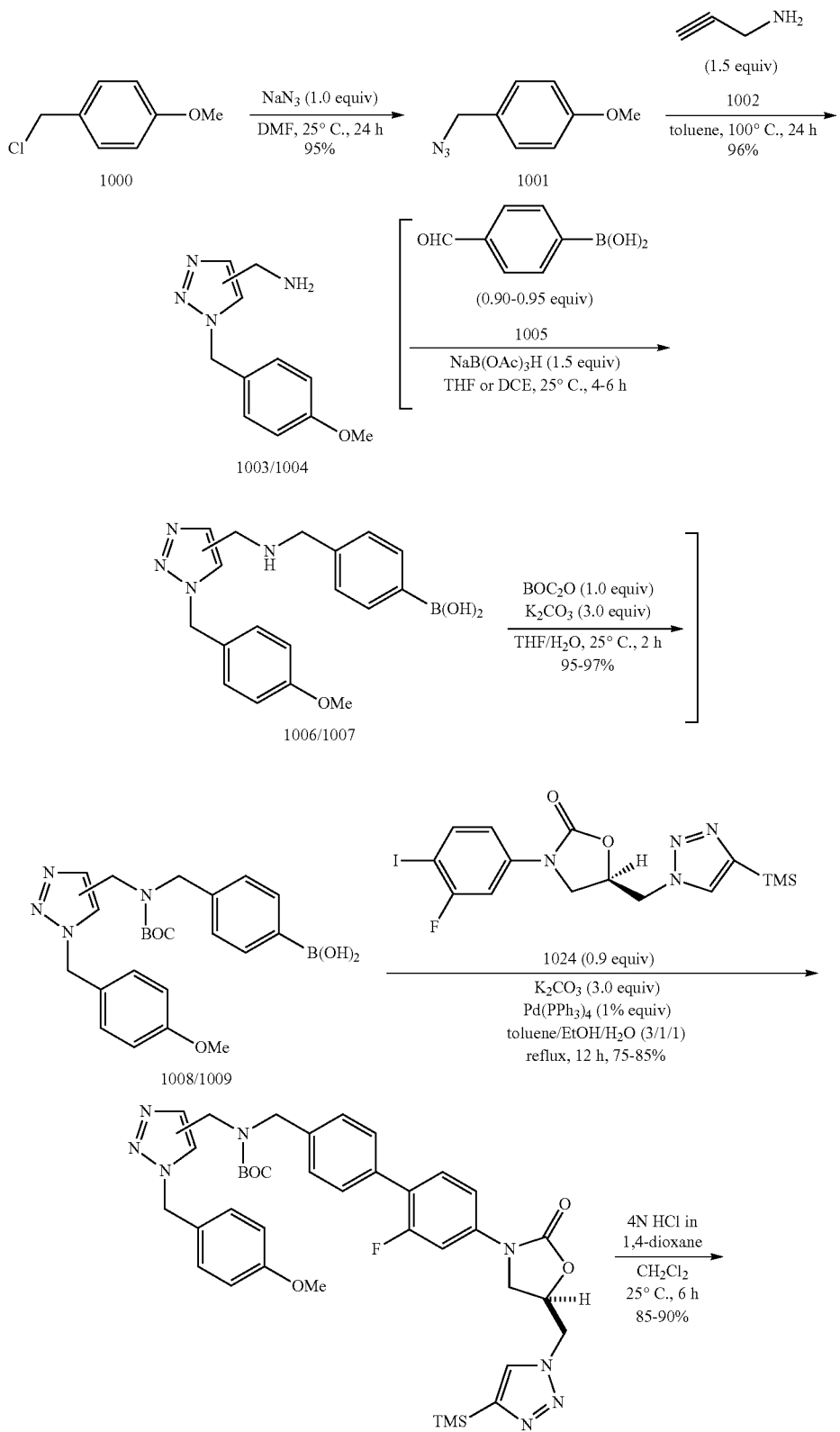

-continued
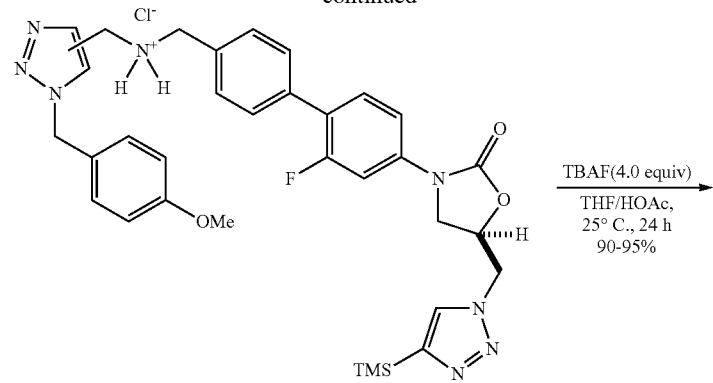
SC-167-63-2
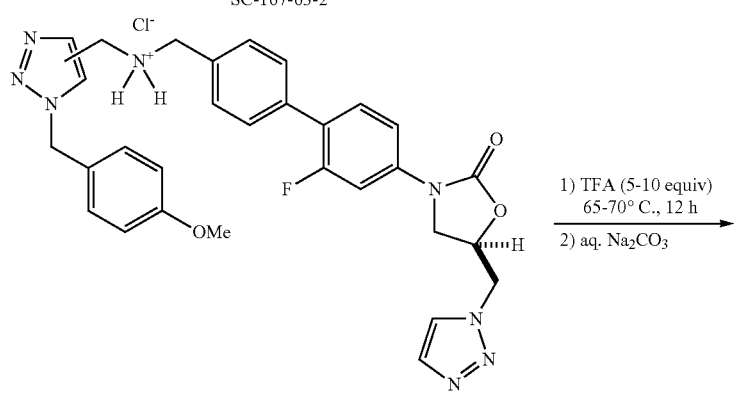
SC-167-71
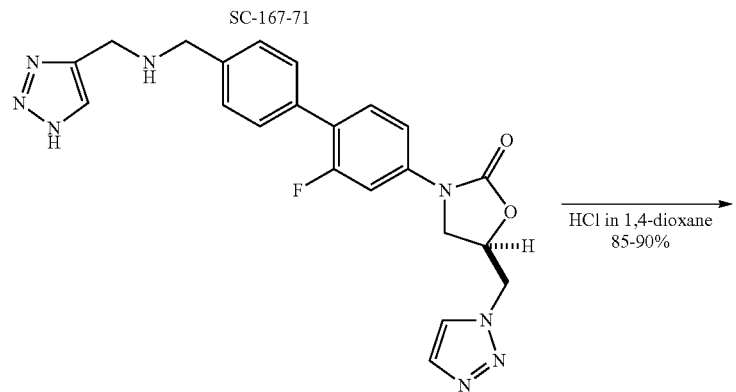
Compound 2
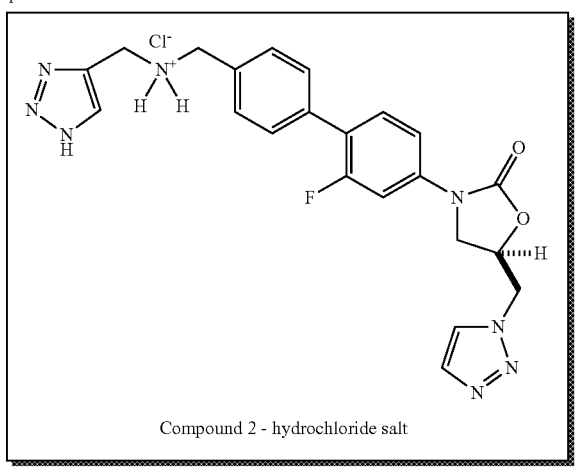
Compound 2 - hydrochloride salt

4-Methoxybenzyl Azide 1001

A solution of 4-methoxybenzyl chloride 1000 (51.8 g, 331.0 mmol) in anhydrous DMF (200 mL) was treated with solid sodium azide (21.5 g, 331.0 mmol, 1.0 equiv) at 25° C., and the resulting mixture was stirred at 25° C. for 24 h. When TLC and HPLC/MS showed that the reaction was complete, the reaction mixture was quenched with $H_2O$ (400 mL) and ethyl acetate (EtOAc, 400 mL) at room temperature. The two layers were separated, and the aqueous layer was extracted with EtOAc (200 mL). The combined organic extracts were washed with $H_2O$ (2×200 mL) and saturated NaCl aqueous solution (100 mL), dried over $MgSO_4$, and concentrated in vacuo. The crude 4-methoxybenzyl azide (51.2 g, 53.95 g theoretical, 94.9% yield) was obtained as colorless oil, which by HPLC and NMR was found to be essentially pure and was directly used in the subsequent reaction without further purifications. For 4-methoxybenzyl azide 1001: $^1$H NMR. (300 MHz, CDCl$_3$) δ 3.84 (s, 3H, ArOCH$_3$), 4.29 (s, 2H, Ar—CH$_2$), 6.96 (d, 2H, J=8.7 Hz), 7.28 (d, 2H, J=7.8 Hz).

C-[1-(4-Methoxy-benzyl)-1H-[1,2,3]triazol-4-yl]-methylamine and C-[3-(4-Methoxy-benzyl)-3H-[1,2,3]triazol-4-yl]-methylamine (1003 and 1004)

A solution of 4-methoxybenzyl azide 1001 (61.2 g, 375.5 mmol) in toluene (188 mL) was treated with propargylamine 1002 (commercially available, 30.97 g, 38.6 mL, 563.0 mmol, 1.5 equiv) at 25° C., and the resulting reaction mixture was warmed up to gentle reflux at 100-110° C. for 21 h. When TLC and HPLC/MS showed that the reaction was complete, the reaction mixture was cooled down to room temperature before being concentrated in vacuo to remove the excess amount of propargylamine and solvent. The oily residue was then treated with 30% ethyl acetate-hexane (v/v, 260 mL), and the resulting mixture was warmed up to reflux and stirred at reflux for 30 min before being cooled down to room temperature for 1 h. The pale-yellow solids were then collected by filtration, washed with 30% ethyl acetate-hexane (v/v, 2×100 mL), and dried in vacuo at 40° C. for overnight to afford the crude, cycloaddition product (78.8 g, 81.75 g theoretical, 96.4%) as a mixture of two regioisomers, C-[1-(4-methoxy-benzyl)-1H-[1,2,3]triazol-4-yl]-methylamine and C-[3-(4-methoxy-benzyl)-3H-[1,2,3]triazol-4-yl]-methylamine (1003 and 1004), in a ratio of 1.2 to 1 by $^1$H NMR The crude cycloaddition product was found to be essentially pure and the two regioisomers were not separated before being used directly in the subsequent reaction without further purification. For 1003 and 1004: $^1$H NMR (300 MHz, DMSO-d$_6$) δ 1.82 (br. s, 2H, NH$_2$), 3.72 and 3.73 (two s, 3H, Ar—OCH$_3$), 5.47 and 5.53 (two s, 2H, ArCH$_2$), 6.89 and 6.94 (two d, 2H, J=8.7 Hz, Ar—H), 7.17 and 7.29 (two d, 2H, J=8.7 Hz, Ar—H), 7.58 and 7.87 (two br. s, 1H, triazole-CH); $C_{11}H_{14}N_4O$, LCMS (EI) m/e 219 (M$^+$+H) and 241 (M$^+$+Na).

4-({tert-Butoxycarbonyl-[1-(4-methoxy-benzyl)-1H-[1,2,3]triazol-4-ylmethyl]-amino}-methyl)-phenyl-boronic acid and 4-({tert-Butoxycarbonyl-[3-(4-methoxy-benzyl)-3H-[1,2,3]triazol-4-ylmethyl]-amino}-methyl)-phenylboronic acid (1008 and 1009)

Method A. A solution of the regioisomeric C-[1-(4-methoxy-benzyl)-1H-[1,2,3]triazol-4-yl]-methylamine and C-[3-(4-methoxy-benzyl)-3H-[1,2,3]triazol-4-yl]-methylamine (1003 and 1004, 20.0 g, 91.74 mmol) in 1,2-dichloroethane (DCE, 280 mL) was treated with 4-formylphenylboronic acid 1005 (commercially available, 12.39 g, 82.57 mmol, 0.9 equiv) at room temperature, and the resulting reaction mixture was stirred at room temperature for 10 min. Sodium triacetoxyborohydride (NaB(OAc)$_3$H, 29.2 g, 137.6 mmol, 1.5 equiv) was then added to the reaction mixture in three portions over the period of 1.5 h at room temperature, and the resulting reaction mixture was stirred at room temperature for an additional 3.5 h. When TLC and HPLC/MS showed that the reductive amination reaction was complete, the reaction mixture was concentrated in vacuo. The residue, which contained a regioisomeric mixture of 4-({[1-(4-methoxy-benzyl)-1H-[1,2,3]triazol-4-ylmethyl]-amino}-methyl)-phenylboronic acid and 4-({[3-(4-methoxy-benzyl)-3H-[1,2,3]triazol-4-ylmethyl]-amino}-methyl)-phenylboronic acid as the reductive amination products (1006 and 1007), was then treated with tetrahydrofuran (THF, 100 mL) and water (H$_2$O, 100 mL). The resulting solution was subsequently treated with solid potassium carbonate (K$_2$CO$_3$, 37.98 g, 275.2 mmol, 3.0 equiv) and di-tert-butyl dicarbonate (BOC$_2$O, 20.02 g, 91.74 mmol, 1.0 equiv) at room temperature and the reaction mixture was stirred at room temperature for 2 h. When TLC and HPLC/MS showed that the N-BOC protection reaction was complete, the reaction mixture was treated with ethyl acetate (EtOAc, 150 mL) and water (1120, 100 mL). The two layers were separated, and the aqueous layer was extracted with ethyl acetate (50 mL). The combined organic extracts were washed with H$_2$O (50 mL), 1.5 N aqueous HCl solution (2×100 mL), H$_2$O (100 mL), and saturated aqueous NaCl solution (100 mL), dried over MgSO$_4$, and concentrated in vacuo. The crude, regioisomeric 4-({tert-butoxycarbonyl-[1-(4-methoxy-benzyl)-1H-[1,2,3]triazol-4-ylmethyl]-amino}-methyl)-phenylboronic acid and 4-({tert-butoxycarbonyl-[3-(4-methoxy-benzyl)-3H-[1,2,3]triazol-4-ylmethyl]-amino}-methyl)-phenylboronic acid (1008 and 1009, 35.98 g, 37.32 g, 96.4%) was obtained as a pale-yellow oil, which solidified upon standing at room temperature in vacuo. This crude material was directly used in the subsequent reaction without further purification. For 1008 and 1009: $^1$H NMR (300 MHz, DMSO-d$_6$) δ 1.32 and 1.37 (two br. s, 9H, COOC(CH$_3$)$_3$), 3.70, 3.73 and 3.74 (three s, 3H, Ar—OCH$_3$), 4.07-4.39 (m, 4H), 5.49 and 5.52 (two s, 2H), 6.70-8.04 (m, 9H, Ar—H and triazole-CH); $C_{23}H_{29}BN_4O_5$, LCMS (EI) m/e 453 (M$^+$+H) and 475 (M$^+$+Na).

Method B. A solution of the regioisomeric C-[1-(4-methoxy-benzyl)-1H-[1,2,3]triazol-4-yl]-methylamine and C-[3-(4-methoxy-benzyl)-3H-[1,2,3]triazol-4-yl]-methylamine (1003 and 1004, 20.06 g, 92.0 mmol) in tetrahydrofuran (THF, 300 mL) was treated with 4-formylphenylboronic acid (13.11 g, 87.4 mmol, 0.95 equiv) at room temperature, and the resulting reaction mixture was stirred at room temperature for 10 min. Sodium triacetoxyborohydride (NaB(OAc)$_3$H, 29.25 g, 138.0 mmol, 1.5 equiv) was then added to the reaction mixture in three portions over the period of 1.5 h at room temperature, and the resulting reaction mixture was stirred at room temperature for an additional 3.5 h. When TLC and HPLC/MS showed that the reductive amination reaction was complete, the reaction mixture, which contained a regioisomeric mixture of 4-({[4-methoxy-benzyl)-1H-[1,2,3]triazol-4-ylmethyl]-amino}-methyl)-phenylboronic acid and 4-({[3-(4-methoxy-benzyl)-3H-[1,2,3]triazol-4-ylmethyl]-amino}-methyl)-phenylboronic acid as the reductive amination products (1006 and 1007), was then treated with water (H$_2$O, 200 mL). The resulting aqueous solution was subsequently treated with solid potassium carbonate (K$_2$CO$_3$, 38.0 g, 276 mmol, 3.0 equiv) and di-tort-butyl dicarbonate (BOC$_2$C$_2$O, 20.08 g, 92 mmol, 1.0 equiv) at room temperature and the reaction mixture was stirred at room temperature for 2 b. When TLC and HPLC/MS showed that the N-BOC protection reaction was complete, the reaction mixture was treated with ethyl acetate (EtOAc, 150 mL) and water (H₂O, 100 mL). The two layers were separated, and the aqueous layer was extracted with ethyl acetate (50 mL). The combined organic extracts were washed with H₂O (50 mL), 1.5 N aqueous HCl solution (2×100 mL), H₂O (100 mL), and saturated aqueous NaCl solution (100 mL), dried over MgSO₄, and concentrated in vacuo. The crude, 4-({tert-butoxycarbonyl-[1-(4-methoxy-benzyl)-1H-[1,2,3]triazol-4-ylmethyl]-amino}-methyl)-phenylboronic acid and 4-({tert-butoxycarbonyl-[3-(4-methoxy-benzyl)-3H-[1,2,3]triazol-4-ylmethyl]-amino}-methyl)-phenylboronic acid (1008 and 1009, 38.45 g, 39.50 g, 97.3%) was obtained as a pale-yellow oil, which solidified upon standing at room temperature in vacuo. This crude material was found to be essentially identical in every comparable aspect as the material obtained from Method A and was directly used in the subsequent reaction without further purification.

{2'-Fluoro-4'-[2-oxo-5-(4-trimethylsilanyl-[1,2,3]triazol-1-ylmethyl)-oxazolidin-3-yl]-biphenyl-4-ylmethyl}-[1-(4-methoxy-benzyl)-1H-[1,2,3]triazol-4-ylmethyl]-carbamic acid tert-butyl ester (SC-167-63-1)

A suspension of the crude regioisomeric mixture of 4-({tert-butoxycarbonyl-[1-(4-methoxy-benzyl)-1H-[1,2,3]triazol-4-ylmethyl]-amino}-methyl)-phenylboronic acid and 4-({tert-butoxycarbonyl-[3-(4-methoxy-benzyl)-3H-[1,2,3]triazol-4-ylmethyl]-amino}-methyl)-phenylboronic acid (1008 and 1009, 0.40 g, 0.89 mmol) and N-[3-(3-fluoro-4-iodo-phenyl)-2-oxo-oxazolidin-5-ylmethyl]-acetamide (1024, 0.37 g, 0.80 mmol, 0.90 equiv) in toluene (3 mL) was treated with powder K₂CO₃ (0.365 g, 5.31 mol, 3.0 equiv), EtOH (1 mL), and H₂O (1 mL) at 25° C., and the resulting mixture was degassed three times under a steady stream of Argon at 25° C. Pd(PPh₃)₄ (51 mg, 0.09 mmol, 0.05 equiv) was subsequently added to the reaction mixture, and the resulting reaction mixture was degassed three times again under a stead stream of Argon at 25° C. before being warmed up to gentle reflux for 18 h. When TLC and HPLC/MS showed the coupling reaction was complete, the reaction mixture was cooled down to room temperature before being treated with H₂O (20 mL) and ethyl acetate (20 mL). The two layers were then separated, and the aqueous layer was extracted with EtOAc (2×20 mL). The combined organic extracts were washed with H₂O (20 mL), 1.5 N aqueous HCl solution (2×20 mL), H₂O (20 mL), and the saturated aqueous NaCl solution (20 mL), dried over MgSO₄, and concentrated in vacuo. The residual oil was solidified upon standing at room temperature in vacuo to afford the crude {2'-Fluoro-4'-[2-oxo-5-(4-trimethylsilanyl-[1,2,3]triazol-1-ylmethyl)-oxazolidin-3-yl)-biphenyl-4-ylmethyl}-[1-(4-methoxy-benzyl)-1H-[1,2,3]triazol-4-ylmethyl]-carbamic acid tert-butyl ester (SC-167-63-1) as a regioisomeric mixture. This crude product (0.484 g, 0.592 g theoretical, 82%) was used directly in the subsequent reaction without further purification. For SC-167-63-1: ¹H NMR (300 MHz, CDCl₃) δ 0.299 and 0.31 (two s, 9H, Si(CH₃)₃), 1.44 and 1.48 (two br. s, 911, N-BOC), 3.76 and 3.80 (two s, 3H, Ar—OCH₃), 3.98-4.01 (dd, 1H, J=3.6, 1.8 Hz), 4.18-4.24 (t, 1H, J=9.0 Hz), 4.27-4.50 (m, 4H), 4.79-4.81 (m, 2H), 5.07-5.1 (br. s, 1H), 5.30 and 5.42 (two s, 2H), 6.81 and 6.89 (dd, 2H), 7.13-7.54 (m, 10H, aromatic H), 7.74 (s, 1H, triazole-CH); C₃₈H₄₅FN₈O₅Si, LCMS (EI) m/e 741 (M⁺+H) and 763 (M⁺+Na).

(5R)-3-[2-Fluoro-4'-({[1-(4-methoxy-benzyl)-1H-[1,2,3]triazol-4-ylmethyl]-amino}-methyl)-biphenyl-4-yl]-5-(4-trimethylsilanyl-[1,2,3]triazol-1-ylmethyl)-oxazolidin-2-one Hydrochloride (SC-167-63-2)

A solution of a regioisomeric mixture of {2'-Fluoro-4'-[2-oxo-5-(4-trimethylsilanyl-[1,2,3]triazol-1-ylmethyl)-oxazolidin-3-yl]-biphenyl-4-ylmethyl}-[1-(4-methoxy-benzyl)-1H-[1,2,3]triazol-4-ylmethyl]-carbamic acid tert-butyl ester SC-167-63-1, 0.18 g, 0.24 mmol) in dichloromethane (CH₂Cl₂, 10, mL) and was treated with a solution of 4 N hydrogen chloride in 1,4-dioxane (0.5 mL, 1.9 mmol, 8.0 equiv) at room temperature, and the resulting reaction mixture was stirred at room temperature for 6 h. When TLC and HPLC/MS showed that the N-BOC deprotection reaction was complete, the solvents were removed in vacuo. The residue was then suspended in 20 mL of 5% methanol (MeOH) in acetonitrile (CH₃CN), and the resulting slurry was stirred at room temperature for 1 h. The solids were then collected by filtration, washed with toluene (2×20 mL) and 5% methanol in acetonitrile (2×20 mL), and dried in vacuo to afford a regioisomeric mixture of the crude, (5R)-3-[2-Fluoro-4'-({[1-(4-methoxy-benzyl)-1H-[1,2,3]triazol-4-ylmethyl]-amino}-methyl)-biphenyl-4-yl]-5-(4-trimethylsilanyl-[1,2,3]triazol-1-ylmethyl)-oxazolidin-2-one hydrochloride (SC-167-63-2, 0.14 g, 0154 g theoretical, 90.9% yield) as off-white crystals. This material was found by ¹H NMR and HPLC/MS to be essentially pure and was directly used in the subsequent reactions without further purification. For SC-167-63-2: ¹H NMR (300 MHz, DMSO-d₆) δ 0.24-0.29 (Two, br. s, 9H, Si(CH₃)₃), 3.18 (S, 3H, Ar—OCH₃), 3.46-3.53 (br. s, 1H), 3.97 (br. t, 1H), 4.27-4.32 (m, 4H), 4.85-4.86 (two, m, 2H), 5.21 (m, 1H), 5.38 (two br. s, 2H, ArCH₂N⁺H₂), 5.66 and 5.70 (two s, 2H), 6.89 and 6.96 (two d, 2H), 7.16 and 7.24 (two d, 2H), 7.32-7.38 (dd, 1H), 7.49-7.88 (m, 6H, aromatic H), 8.22 (s, 1H, triazole-CH), 8.30 (s, 1H, triazole-CH); C₃₃H₃₇FN₈O₃Si, LCMS (EI) m/e 641 (M⁺+H) and 663 (M⁺+Na).

(5R)-3-[2-Fluoro-4'-({[1-(4-methoxy-benzyl)-1H-[1,2,3]triazol-4-ylmethyl]-amino}-methyl)-biphenyl-4-yl]-5-[1,2,3]triazol-1-ylmethyl-oxazolidin-2-one A solution of 3-[2-Fluoro-4'-({[1-(4-methoxy-benzyl)-1H-[1,2,3]triazol-4-ylmethyl]-amino}-methyl)-biphenyl-4-yl]-5-(4-trimethylsilanyl-[1,2,3]triazol-1-ylmethyl)-oxazolidin-2-one hydrochloride (SC-167-63-2, 0.22 g, 0.343 mmol) in an 1 M solution of tetrabutylammonium fluoride in THF (TBAF, 1.4 mL, 1.4 mmol, 4.0 equiv) was treated with acetic acid (HOAc, 5.0 mL) at room temperature, and the resulting reaction mixture was stirred at room temperature for 24 h. When TLC and HPLC/MS showed that the reaction was complete, the solvents were removed in vacuo. The residue was treated with H₂O (30 mL) at room temperature and the resulting mixture was stirred at room temperature for 1 h. The solids were collected by filtration, washed with H₂O (2×10 mL) and 20% EtOAc/hexane (2×20 mL), dried in vacuo. The crude, desired (5R)-3-[2-Fluoro-4'-({[1-(4-methoxy-benzyl)-1H-[1,2,3]triazol-4-ylmethyl]-amino}-methyl)-biphenyl-4-yl]-5-[1,2,3]triazol-1-ylmethyl-oxazolidin-2-one (SC-167-71, 0.17 g, 0.195 g theoretical, 87%) was obtained as off-white powders, which by HPLC/MS and ¹H NMR was found to be essentially pure and was directly used in the subsequent reactions without further purification. For SC-167-71: ¹H NMR (300 MHz, DMSO-d₆) 3.73 and 3.75 (two, s, 4H), 3.94-3.97 (m, 1H, 4.29 (t, 1H), 4.85 and 4.87 (dd, 2H), 5.15-5.20 (m, 1H, 5.48 (s, 1H), 6.91 and 6.94 (d, 2H), 7.28-7.58 (m, 10H, aromatic-H), 7.78 (s, 1H, triazole-H), 7.98 (s, 1H, triazole-H), 8.19 (s, 1H, triazole-H); C$_{30}$H$_{29}$FN$_8$O$_3$, LCMS (EI) m/e 568 (M$^+$+H).

(5R)-3-(2-Fluoro-4'-{[(1H-[1,2,3]triazol-4-ylmethyl)-amino]-methyl}-biphenyl-4-yl)-5-[1,2,3]triazol-1-ylmethyl-oxazolidin-2-one hydrochloride (Compound 2 hydrochloride salt)

A solution of the crude regioisomeric mixture of (5R)-3-[2-Fluoro-4'-({[1-(4-methoxy-benzyl)-1H-[1,2,3]triazol-4-ylmethyl]-amino}-methyl)-biphenyl-4-yl)-5-(1,2,3]triazol-1-ylmethyl-oxazolidin-2-one (SC-167-71, 0.30 g, 0.528 mmol) in trifluoroacetic acid (TFA, 10 mL) was warmed up to 65-70° C., and the resulting reaction mixture was stirred at 65-70° C. for 12 h. When TLC and HPLC/MS showed that the deprotection reaction was complete, the solvents were removed in vacuo. The residual solids were then treated with ethyl acetate (EtOAc, 10 mL) and H$_2$O (15 mL) before being treated with a saturated aqueous solution of sodium carbonate (30 mL) at room temperature. The resulting mixture was then stirred at room temperature for 1 h before the solids were collected by filtration, washed with EtOAc (2×20 mL) and H$_2$O (2×20 mL), and dried in vacuo at 40-45° C. to afford the crude, (5R)-3-(2-Fluoro-4'-{[(1H-[1,2,3]triazol-4-ylmethyl)-amino]-methyl}-biphenyl-4-yl)-5-[1,2,3]triazol-1-ylmethyl-oxazolidin-2-one (Compound 2 as the free base, 0.18 g, 0.24 g theoretical, 75%) as off-white powders, which by HPLC/MS and $^1$H NMR was found to be one pure regioisomer. For Compound 2 as the free base: $^1$H NMR (300 MHz, DMSO-d$_6$) δ 3.71-3.77 (two br. s, 4H, Ar$_1$CH$_2$NHCH$_2$Ar$_2$), 3.93-3.98 (m, 1H), 4.26-4.32 (t, 1H), 4.86 and 4.87 (d, 2H), 5.14-5.22 (m, 1H), 7.35-7.59 (m, 7H, aromatic-H), 7.74 and 7.78 (s, 2H, triazole-CH), 8.19 (s, 1H, triazole-CH); C$_{22}$H$_{21}$FN$_8$O$_2$, LCMS (EI) m/e 449 (M$^+$+H) and 471 (M$^+$+Na).

A suspension of Compound 2 free base (0.18 g, 0.40 mmol) in ethyl acetate (EtOAc, 80 mL), and methanol (MeOH, 20 mL) was treated with a solution of 4.0 N hydrogen chloride in 1,4-dioxane at room temperature, and the resulting mixture was stirred at room temperature for 8 h. The solvents were then removed in vacuo, and the residue was further dried in vacuo before being treated with a mixture of 10% methanol in acetonitrile (20 mL). The solids were collected by filtration, washed with 10% MeOH/acetonitrile (2×10 mL), and dried in vacuo to afford Compound 2 hydrochloride salt (0.19 g, 0.194 g theoretical, 98% yield) as off-white crystals.

The crude Compound 2 hydrochloride salt can be recrystallized from acetonitrile and water, if necessary, according to the following procedure: A suspension of the crude 1 hydrochloride salt (2.0 g) in acetonitrile (150 mL) was warmed up to reflux before the distilled water (H$_2$O, 10 mL) was gradually introduced to the mixture. The resulting clear yellow to light brown solution was then stirred at reflux for 10 min before being cooled down to 45-55° C. The solution was then filtered through a Celite bed at 45-55° C., and the filtrates were gradually cooled down to room temperature before being further cooled down to 0-5° C. in an ice bath for 1 h. The solids were then collected by filtration, washed with acetonitrile (2×50 mL), and dried in vacuo at 40° C. for 24 h to afford the recrystallized Compound 2 hydrochloride salt (1.58 g, 2.0 g theoretical, 79% recovery) as off-white crystals. For Compound 2HCl salt: $^1$H NMR (300 MHz, DMSO-d$_6$) δ 3.94-3.99 (m, 1H), 4.22-4.33 (m, 1H and 4H), 4.86 and 4.88 (d, 2H), 5.15-5.22 (m, 1H), 7.18-7.69 (m, 7H, aromatic-H), 7.78 (s, 1H, triazole-CH), 8.13 (s, 1H, triazole-CH), 8.21 (s, 1H, triazole-CE), 9.99 (br. s, 2H, ArCH$_2$N$^+$H$_2$), 12.20 (br. s, 1H, triazole NH); C$_{22}$H$_{21}$FN$_8$O$_2$—HCl, LCMS (EI) m/e 449 (M$^+$+H) and 471 (M$^+$+Na).

Example 3

Synthesis of Compound 3

Compound 3 is prepared using a reaction scheme analogous to that for compound 1, using oxazolidinone compound 1026 in place of oxazolidinone compound 1010.

Synthesis of Oxazolidinone Compound 1026

Oxazolidinone compound 1026 is prepared according to the following reaction scheme which is analogous to that used for the synthesis of oxazolidione compound 1010.

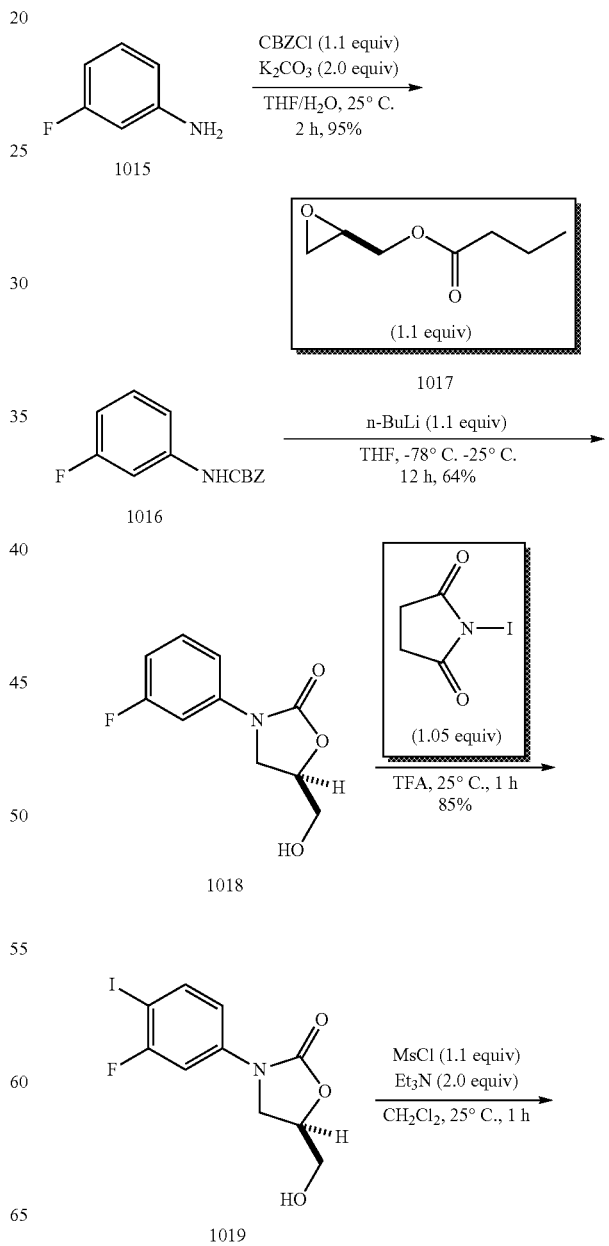

-continued

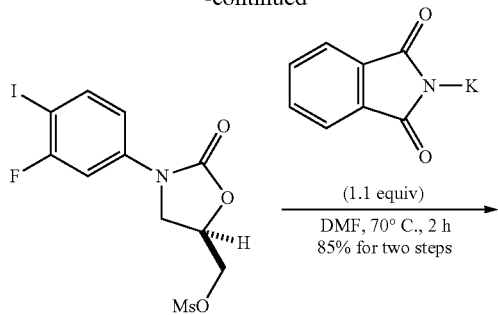

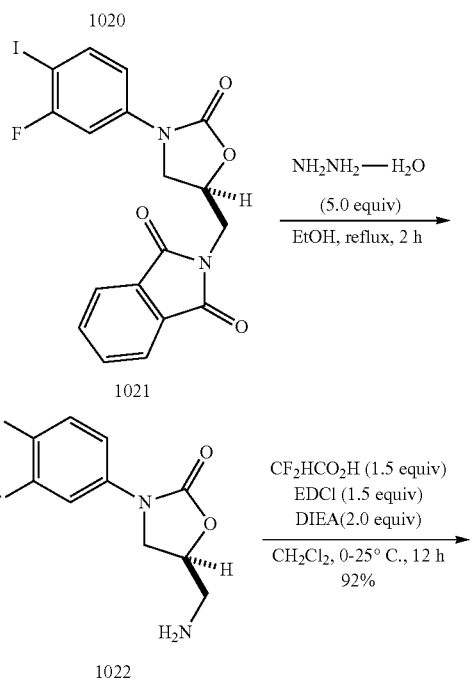

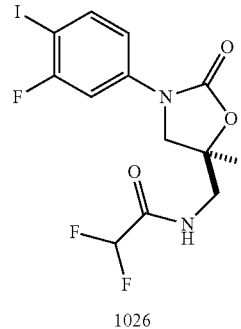

1026

(5S)-2,2-Difluoro-N-[3-(3-fluoro-4-iodo-phenyl)-2-oxo-oxazolidin-5-ylmethyl]-acetamide (1026)

A suspension of (5S)-5-Aminomethyl-3-(3-fluoro-4-iodophenyl)-oxazolidin-2-one (1022, 5.0 g, 14.88 mmol) in methylene chloride ($CH_2Cl_2$, 50 mL) was treated with difluoroacetic acid (2.14 g, 1.41 mL, 22.32 mmol, 1.5 equiv) and N,N-diisopropylethylamine (DIEA or Hunig's base, 3.85 g, 5.18 mL, 29.76 mmol, 2.0 equiv), and the resulting reaction mixture was cooled down to 0-5° C. before being treated with EDCl (4.30 g, 22.32 mmol, 1.5 equiv) at 0-5° C. The reaction mixture was subsequently stirred at 0-5° C. for 1 h before being gradually warmed up to room temperature for 12 h. When TLC and HPLC/MS showed that the reaction was complete, the reaction mixture was quenched with $H_2O$ (50 mL) and $CH_2Cl_2$ (50 mL). The two layers were then separated, and the aqueous layer was extracted with $CH_2Cl_2$ (2×50 mL). The combined organic extracts were washed $H_2O$ (50 mL) and the saturated aqueous NaCl solution (50 mL), dried over $MgSO_4$, and concentrated in vacuo to afford the crude (5 S) 2,2-difluoro-N-[3-(3-fluoro-4-iodo-phenyl)-2-oxo-oxazolidin-5-ylmethyl]-acetamide (1026, 5.64 g, 6.16 g theoretical, 91.6%) as off-white powders, which by HPLC/MS and $^1H$ NMR was found to be essentially pure and was directly used in the subsequent reactions without further purification. For 1026: $^1H$ NMR (300 MHz, DMSO-$d_6$) δ 3.54 (t, 2H, J=5.5 Hz), 3.77 (dd, 1H, J=6.3, 9.2 Hz), 4.15 (t, 1H, J=9.2 Hz), 4.77-4.86 (m, 1H), 6.25 (t, 1H, J=53.52 Hz, —CHCF$_2$), 7.18 (dd, 1H, J=2.4, 8.7 Hz), 7.55 (dd, 1H, J=2.4, 8.7 Hz), 7.84 (t, 1H, J=8.5 Hz), 9.19 (t, 1H, J=5.5 Hz, —CONH); $C_{12}H_{10}F_3IN_2O_3$, LCMS (EI) m/e 415 (M$^+$+H), 456 (M$^+$+H+$CH_3CN$).

Example 4

Synthesis of Compound 4

Compound 4 can be prepared using a reaction scheme analogous to that for compound 1, using oxazoldinone compound 1027 in place of oxazolidinone compound 1010.

Synthesis of Oxazolidionone Compound 1027

Oxazolidinone compound 1027 can be prepared using a reaction scheme analogous to that for oxazolidinone compound 1026, in which compound 1022 is reacted with dichloroacetic acid or dichloroacetic anhydride to produce oxazolidinone compound 1027.

Example 5

Synthesis of Compound 5

Compound 5 can be prepared using a reaction scheme analogous to that for compound 1, using 1-amino-4-pentyne 1028 in place of propargyl amine 1002.

Synthesis of 1028

Compound 1028 can be made using standard chemistry procedures, starting with 1-hydroxy-4-pentyne (commercially available from Aldrich), converting this hydroxyl compound to its mesylate (mesyl chloride, Hunig's base, dichloromethane), converting the mesylate to the azide (sodium azide, tetrahydrofuran/dimethylformamide), and reduction of the azide to the amine (triphenylphosphine, tetrahydrofuran).

Example 6

Synthesis of Compound 6

Compound 6 can be prepared using a reaction scheme analogous to that for compound 1, using 1-amino-3-butyne (commercially available from AB Chemicals) 1029 in place of propargyl amine 1002.

Example 7

Synthesis of Compound 7

Compound 7 can be prepared using a reaction scheme analogous to that for compound 1, using N-methyl-1-amino- 2-propyne (also known as N-methyl-propargyl amine (commercially available from Aldrich) 1030 in place of propargyl amine 1002.

Example 8

Synthesis of Compound 8

Compound 8 can be prepared using a reaction scheme analogous to that for compound 1, using 1-amino-1-methyl-2-propyne 1031 (commercially available from AB Chem Inc.) in place of propargyl amine 1002.

Example 9

Synthesis of Compound 9

Compound 9 can be prepared using a reaction scheme analogous to that for compound 1, using 4-(4,4,5,5-tetramethyl-1,3,2-dioxaborolane)-phenylacetaldehyde 1032 (which can be made by reduction of the corresponding carboxyl acid) in place of 4-formylphenylboronic acid 1005.

Example 10

Synthesis of Compound 10

Compound 10 can be prepared using a reaction scheme analogous to that for compound 1, using 1-amino-3-butyne (commercially available from AB Chemicals) 1029 in place of propargyl amine 1002 and 4-(4,4,5,5-tetramethyl-1,3,2-dioxaborolane)-phenylacetaldehyde 1032 (which can be made by reduction of the corresponding carboxyl acid) in place of 4-formylphenylboronic acid 1005.

Example 11

Synthesis of Compound 11

Compound 11 can be prepared using a reaction scheme analogous to that for compound 1, using oxazolidinone compound 1033 (synthesis described in PCT application No. WO 99/10342, to Zeneca Limited, published Mar. 4, 1999) in place of oxazolidinone compound 1010.

Example 12

Synthesis of Compound 12

Compound 12 can be prepared using a reaction scheme analogous to that for compound 1, using oxazolidinone compound 1034 in place of oxazolidinone compound 1010. Oxazoldinone compound 1034 can be prepared in an analogous manner to oxazolidinone 1025 using 3,5-difluorophenylamine in place of 3-fluorophenylamine 1015.

Example 13

Synthesis of Compound 13

Compound 13 can be prepared using a reaction scheme analogous to that for compound 1, using oxazolidinone compound 1035 in place of oxazolidinone compound 1010. Oxazoldinone compound 1035 can be prepared in an analogous manner to oxazolidinone 1026 using 3,5-difluorophenylamine in place of 3-fluorophenylamine 1015.

Example 14

Synthesis of Compound 14

Compound 14 can be prepared using a reaction scheme analogous to that for compound 1, using oxazolidinone compound 1036 in place of oxazolidinone compound 1010. Oxazoldinone compound 1036 can be prepared in an analogous manner to oxazolidinone 1027 using 3,5-difluorophenylamine in place of 3-fluorophenylamine 1015.

Example 15

Synthesis of Compound 15

Compound 15 can be prepared using a reaction scheme analogous to that for compound 1, using 1-amino-4-pentyne 1028 in place of propargyl amine 1002, and oxazolidinone compound 1033 (synthesis described in PCT application No. WO 99/10342, to Zeneca Limited, published Mar. 4, 1999) in place of oxazolidinone compound 1010.

Example 16

Synthesis of Compound 16

Compound 16 can be prepared using a reaction scheme analogous to that for compound 1, using 1-amino-3-butyne (commercially available from AB Chemicals) 1029 in place of propargyl amine 1002, and oxazolidinone compound 1033 (synthesis described in PCT application No. WO 99/10342, to Zeneca Limited, published Mar. 4, 1999) in place of oxazolidinone compound 1010.

Example 17

Synthesis of Compound 17

Compound 17 can be prepared using a reaction scheme analogous to that for compound 1, using N-methyl-1-amino-2-propyne (also known as N-methyl-propargyl amine (commercially available from Aldrich) 1030 in place of propargyl amine 1002, and oxazolidinone compound 1033 (synthesis described in PCT application No. WO 99/10342, to Zeneca Limited, published Mar. 4, 1999) in place of oxazolidinone compound 1010.

Example 18

Synthesis of Compound 18

Compound 18 can be prepared using a reaction scheme analogous to that for compound 1, using 1-amino-1-methyl-2-propyne 1031 in place of propargyl amine 1002, and oxazolidinone compound 1033 (synthesis described in PCT application No. WO 99/10342, to Zeneca Limited, published Mar. 4, 1999) in place of oxazolidinone compound 1010.

Example 19

Synthesis of Compound 19

Compound 19 can be prepared using a reaction scheme analogous to that for compound 1, using oxazolidinone compound 1033 (synthesis described in PCT application No. WO 99/10342, to Zeneca Limited, published Mar. 4, 1999) in place of oxazolidinone compound 1010, and 4-(4,4,5,5-tetramethyl-1,3,2-dioxabolrolane)-phenylacetaldehyde 1032 (which can be made by reduction of the corresponding carboxyl acid) in place of 4-formylphenylboronic acid 1005.

Example 20

Synthesis of Compound 20

Compound 20 can be prepared using a reaction scheme analogous to that for compound 1, using 1-amino-3-butyne (commercially available from AB Chemicals) 1029 in place of propargyl amine 1002, oxazolidinone compound 1033 (a synthesis which is described in PCT application No. WO 99/10342, to Zeneca Limited, published Mar. 4, 1999) in place of oxazolidinone compound 1010, and 4-(4,4,5,5-tetramethyl-1,3,2-dioxaborolane)-phenylacetaldehyde 1032 (which can be made by reduction of the corresponding carboxyl acid) in place of 4-formylphenylboronic acid 1005.

For Examples 21-30, the Suzuki coupling reaction step, i.e. step 3 of the present invention, is more typically conducted in which the "Q" and "Z" substituents are reversed from the "Q" and "Z" substituents of Examples 1-20.

Example 21

Synthesis of Compound 21

Compound 21 can be prepared using a reaction scheme analogous to that for compound 1, using the boronic ester oxazolidinone compound 1037 in place of oxazolidinone 1010 and pyridyl bromo aldehyde 1038 in place of aldehyde compound 1005. Compound 1037 can be made from compound 1010 using a procedure described in PCT application No. WO 2005012271, to Rib-X Pharmaceuticals, Inc., published Feb. 10, 2005.

Synthesis of Boronic Ester 1037

A suspension of (5S)—N-[3-(3-fluoro-4-iodo-phenyl)-2-oxo-oxazolidin-5-ylmethyl]-acetamide 1010 (20.0 g, 52.8 mmol, prepared as described in Example 1, above) in anhydrous 1,4-dioxane (130 mL) was treated with 4,4,5,5-tetramethyl-[1,3,2]dioxaborolane (10.2 g, 11.6 mL, 80.0 mmol, 1.5 equiv) and triethylamine (16.0 g, 22.4 mL, 158.4 mmol, 3.0 equiv) at room temperature. The resulting reaction mixture was degassed three times under a steady stream of argon before being treated with dichloro[1,1'-bis(diphenylphosphino)ferrocene] palladium (II) (Pd(dppf)$_2$Cl$_2$, 1.32 g, 1.6 mmol, 0.03 equiv) at room temperature. The resulting reaction mixture was degassed three times under a steady stream of argon before being warmed to reflux for 7 h. When HPLC/MS showed the reaction was complete, the reaction mixture was cooled to room temperature before being treated with water (100 mL) and ethyl acetate (100 mL). The two layers were separated, and the aqueous layer was extracted with ethyl acetate (2×50 mL). The combined organic extracts were washed with water (2×50 mL) and saturated aqueous NaCl (50 mL), dried over MgSO$_4$, and concentrated in vacuo. The residual brown oil was further dried in vacuo to afford the (5S)—N-{3-[3-fluoro-4-(4,4,5,5-tetramethyl-[1,3,2]dioxaborolan-2-yl)-phenyl]-2-oxo-oxazolidin-5-ylmethyl}acetamide 1037 (18.8 g, 94%) as brown solids. This product was directly used in subsequent reactions without further purification. $C_{13}H_{24}BFN_2O_5$, HPLC/MS (ESI) m/e 379 (M$^+$+H).

Synthesis of Compound 1038

A solution of 2,5-Dibromo-pyridine (22.2 g, 93.7 mmol, 1.0 equiv.) in toluene (1.2 L) was treated with nBuLi (70.25 ml, 112.4 mmol, 1.2 equiv.) dropwise at −78° C. The resulting solution was stirred at −78° C. for about 30 minutes, and DMF (11 ml, 141 mmol, 1.5 equiv.) was added. The reaction solution was warmed up gradually to RT and then stirred overnight. When TLC and MS showed the reaction was complete, the reaction mixture was concentrated in vacuo, and the residue was directly purified by column chromatography (SiO$_2$, 10-30% EtOAc/Hexanes gradient elution) to afford 5-Bromo-pyridine-2-carbaldehyde (1038, 5.45 g, 31% yield) as yellowish white solid. For 1038: C6H4BrNO, LCMS (EI) m/e 187 (M$^+$+H).

Example 22

Synthesis of Compound 22

Compound 22 can be prepared using a reaction scheme analogous to that for compound 1, using the boronic ester oxazolidinone compound 1039 in place of oxazolidinone 1010 and pyridyl bromo aldehyde 1038 in place of aldehyde compound 1005. Compound 1039 can be made from compound 1025 using a procedure analogous to that for making compound 1037 from compound 1010.

Example 23

Synthesis of Compound 23

Compound 23 can be prepared using a reaction scheme analogous to that for compound 1, using the boronic ester oxazolidinone compound 1040 in place of oxazolidinone 1010 and pyridyl bromo aldehyde 1038 in place of aldehyde compound 1005. Compound 1040 can be made from compound 1026 using a procedure analogous to that for making compound 1037 from compound 1010.

Example 24

Synthesis of Compound 24

Compound 24 can be prepared using a reaction scheme analogous to that for compound 1, using the boronic ester oxazolidinone compound 1041 in place of oxazolidinone 1010 and pyridyl bromo aldehyde 1038 in place of aldehyde compound 1005. Compound 1041 can be made from compound 1027 using a procedure analogous to that for making compound 1037 from compound 1010.

Example 25

Synthesis of Compound 25

Compound 25 can be prepared using a reaction scheme analogous to that for compound 1, using 1-amino-4-pentyne 1028 in place of propargyl amine 1002, using the boronic ester oxazolidinone compound 1037 in place of oxazolidinone 1010 and pyridyl bromo aldehyde 1038 in place of aldehyde compound 1005.

Example 26

Synthesis of Compound 26

Compound 26 can be prepared using a reaction scheme analogous to that for compound 1, using 1-amino-3-butyne (commercially available from AB Chemicals) 1029 in place of propargyl amine 1002, using the boronic ester oxazolidinone compound 1037 in place of oxazolidinone 1010 and pyridyl bromo aldehyde 1038 in place of aldehyde compound 1005.

Example 27

Synthesis of Compound 27

Compound 27 can be prepared using a reaction scheme analogous to that for compound 1, using N-methyl-1-amino-2-propyne (also known as N-methyl-propargyl amine (commercially available from Aldrich) 1030 in place of propargyl amine 1002, using the boronic ester oxazolidinone compound 1037 in place of oxazolidinone 1010 and pyridyl bromo aldehyde 1038 in place of aldehyde compound 1005.

Example 28

Synthesis of Compound 28

Compound 28 can be prepared using a reaction scheme analogous to that for compound 1, using 1-amino-1-methyl-2-propyne 1031 in place of propargyl amine 1002, using the boronic ester oxazolidinone compound 1037 in place of oxazolidinone 1010 and pyridyl bromo aldehyde 1042 in place of aldehyde compound 1005.

Example 29

Synthesis of Compound 29

Compound 29 can be prepared using a reaction scheme analogous to that for compound 1, using the boronic ester oxazolidinone compound 1037 in place of oxazolidinone 1010, and pyridyl bromo benzaldehyde 1042 in place of aldehyde compound 1005.

Synthesis of Compound 1042

Pyridyl bromobenzaldehyde 1042 can be prepared by reacting 2,5-dibromopyridine with 1-amino-1-methyl-2-propyne 1031, followed by reduction with DIBAL.

Example 30

Synthesis of Compound 30

Compound 30 can be prepared using a reaction scheme analogous to that for compound 1, using 1-amino-3-butyne (commercially available from AB Chemicals) 1029 in place of propargyl amine 1002, using the boronic ester oxazolidinone compound 1037 in place of oxazolidinone 1010, and pyridyl bromo benzaldehyde 1042 in place of aldehyde compound 1005.

Reverse of Components for Suzuki Coupling Reactions

The forgoing compounds of Examples 1-30 can all be prepared in which the "Q" and "Z" substituents with respect to Step 3 can be reversed, such that the Suzuki Coupling components are reversed.

INCORPORATION BY REFERENCE

The entire disclosure of each of the patent documents, including certificates of correction, patent application documents, scientific articles, governmental reports, websites, and other references referred to herein is incorporated by reference in its entirety for all purposes.

EQUIVALENTS

The invention can be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A compound corresponding to the structure

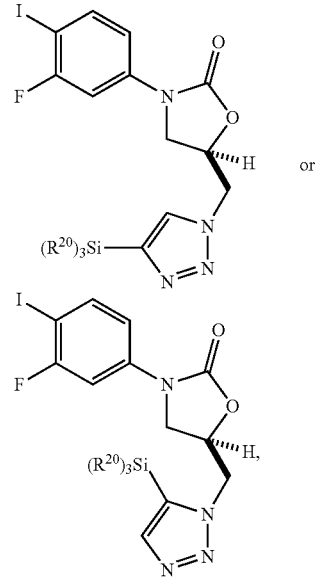

or a pharmaceutically acceptable salt thereof, wherein each $R^{20}$ is independently $C_1$-$C_6$ alkyl or —O—($C_1$-$C_6$ alkyl).

2. A compound according to claim 1, wherein each $R^{20}$ is methyl.

* * * * *